United States Patent
Johs et al.

(10) Patent No.: US 9,354,118 B2
(45) Date of Patent: May 31, 2016

(54) MULTIPLE WAVELENGTH ELLIPSOMETER SYSTEM AND RELATED METHOD

(71) Applicant: Film Sense, LLC, Lincoln, NE (US)

(72) Inventors: Blaine D. Johs, Lincoln, NE (US); Bruce A. Hadwiger, Columbus, NE (US)

(73) Assignee: Film Sense, LLC, Lincoln, NE (US)

( * ) Notice: Subject to any disclaimer, the term of this patent is extended or adjusted under 35 U.S.C. 154(b) by 176 days.

(21) Appl. No.: 14/173,994

(22) Filed: Feb. 6, 2014

(65) Prior Publication Data
US 2015/0219497 A1   Aug. 6, 2015

(51) Int. Cl.
*G01J 4/02* (2006.01)
*G01N 21/21* (2006.01)

(52) U.S. Cl.
CPC ............... *G01J 4/02* (2013.01); *G01N 21/211* (2013.01); *G01N 2021/213* (2013.01); *G01N 2021/215* (2013.01); *G01N 2021/216* (2013.01)

(58) Field of Classification Search
None
See application file for complete search history.

(56) References Cited

U.S. PATENT DOCUMENTS

| | | | |
|---|---|---|---|
| 4,681,450 A | 7/1987 | Azzam | |
| 5,081,348 A | 1/1992 | Siddiqui | |
| 5,335,066 A | 8/1994 | Yamada et al. | |
| 5,548,404 A | 8/1996 | Kupershmidt et al. | |
| 5,757,671 A | 5/1998 | Drevillon et al. | |
| 5,872,630 A | 2/1999 | Johs et al. | |
| 5,956,147 A | 9/1999 | Jellison, Jr. et al. | |
| 6,034,777 A | 3/2000 | Johs et al. | |
| 6,043,887 A | 3/2000 | Allard et al. | |
| 6,177,995 B1 | 1/2001 | Compain et al. | |
| 6,320,657 B1 | 11/2001 | Aspnes et al. | |
| 6,384,916 B1 * | 5/2002 | Furtak ................... | G01J 3/447 356/369 |
| 6,717,706 B2 | 4/2004 | Miller et al. | |
| 6,836,327 B1 | 12/2004 | Yao | |
| 7,038,776 B1 | 5/2006 | Ansley et al. | |
| 7,061,612 B2 | 6/2006 | Johnston | |
| 7,492,455 B1 | 2/2009 | Johs et al. | |
| 7,616,319 B1 | 11/2009 | Woollam et al. | |

(Continued)

FOREIGN PATENT DOCUMENTS

CA     2278981 A1 *   1/2001

OTHER PUBLICATIONS

Azzam, R.M.A., "Division-of-amplitude Photopolarimeter (DOAP) for the Simultaneous Measurement of All Four Stokes Parameters of Light", Optica Acta: International Journal of Modern Optics, 1982, 685-689, 29:5, Electrical Engineering Department, College of Engineering, University of New Orleans, Louisiana 70148, U.S.

(Continued)

*Primary Examiner* — Gordon J Stock, Jr.
(74) *Attorney, Agent, or Firm* — Suiter Swantz pc llo

(57) ABSTRACT

A multiple wavelength ellipsometer system for use in thin film characterization is disclosed. The light source for the system may include sequentially scanned multiple light emitting diodes or laser diodes. The polarization state detector may comprise no moving parts, and utilizes economical uncoated glass plates as beam splitters. The system compensates for potential measurement errors induced by misalignment of the input beam angle to the polarization state detector via a paired arrangement of the beam splitters. To provide improved accuracy in the analysis of data acquired by the system, methods herein actively compensate for the relatively large bandwidth of a preferable light emitting diode source.

20 Claims, 25 Drawing Sheets

(56) References Cited

U.S. PATENT DOCUMENTS

| | | |
|---|---|---|
| 7,800,755 B1 | 9/2010 | Poirier et al. |
| 2010/0201799 A1 | 8/2010 | Mohrholz et al. |
| 2011/0243300 A1 | 10/2011 | Kaneko et al. |

OTHER PUBLICATIONS

Azzam, R.M.A. and Ali G. Lopez, "Accurate calibration of the four-detector photopolarimeter with imperfect polarizing optical elements", J. Opt. Soc. Am. A, Oct. 1989, 1513-1521, 6:10, Department of Electrical Engineering, University of New Orleans, Lakefront, New Orleans, Louisiana 70148, U.S.

Collins, R.W., "Automatic rotating element ellipsometers: Calibration, operation, and realtime applications", Review of Scientific Instruments, Aug. 1990, 2029-2062, 61:8, AIP Publishing, The Pennsylvania State University, Materials Research Laboratory and Department of Physics, University Park, Pennsylvania 16802, U.S.

Azzam, R.M.A., "Division-of-amplitude photopolarimeter based on conical diffraction from a metallic grating", Applied Optics, Jul. 1, 1992, 3574-3576, 31:19, Optical Society of America.

Jellison, G.E. and J.W. McCamy, "Sample depolarization effects from thin films of ZnS on GaAs as measured by spectroscopic ellipsometry", Applied Physics Letters, Aug. 3, 1992, 512-514, 61:5, American Institute of Physics.

Johs, Blaine, "Regression calibration method for rotating element ellipsometers", Thin Solid Films, 1993, 395-398, 234, Elsevier Sequoia.

Joerger, R., K. Forcht, A. Gombert, M. Kohl, and W. Graf, "Influence of incoherent superposition of light on ellipsometric coefficients", Applied Optics, Jan. 1, 1997, 319-327, 36:1, Optical Society of America.

Jellison JR., Gerald E., "Windows in ellipsometry measurements", Applied Optics, Aug. 1, 1999, 4784-4789, 38:22, Optical Society of America.

Azzam, Rasheed M.A. and Faisal F. Sudradjat, "Single-layer-coated beam splitters for the division-of-amplitude photopolarimeter", Applied Optics, Jan. 10, 2005, 190-196, 44, Department of Electrical Engineering, Electrical Engineering Faculty Publications, University of New Orleans, U.S.

Larouche, Stephane and Ludvik Martinu, "OpenFilters: open-source software for the design, optimization, and synthesis of optical filters", Applied Optics, May 1, 2008, C219-C230, 47:13, Optical Society of America.

Tompkins, Harland G. and Eugene A. Irene. Handbook of Ellipsometry. 2005. William Andrew Publishing. Chapter 3: 253-296.

Loescher, D.H., et al. "Least-Squares Analysis of the Film-Substrate Problem in Ellipsometry", Journal of the Optical Society of America, 1971, vol. 61, No. 9, p. 1230.

Eichstadt, S., et al. "Comparison of the Richardson-Lucy method and a classical approach for spectrometer bandpass correction", Metrologia, 2013, vol. 50, p. 107.

\* cited by examiner

|  | Gaussian+Exponential Lineshape | | | | Gaussian-Only Lineshape | | |
|---|---|---|---|---|---|---|---|
|  | P | W | L | R | A | P | W | A |
| Blue | 464.8 | 21.5 | 6.9 | 12.5 | 6816.8 | 465.5 | 25.0 | 6451.5 |
| Green | 520.0 | 33.4 | 8.7 | 15.8 | 4973.5 | 520.9 | 36.2 | 4823.8 |
| Yellow | 592.5 | 14.6 | 8.2 | 5.6 | 2526.4 | 592.2 | 17.3 | 2377.1 |
| Red | 635.8 | 15.6 | 10.0 | 5.6 | 4787.8 | 635.3 | 18.8 | 4483.3 |

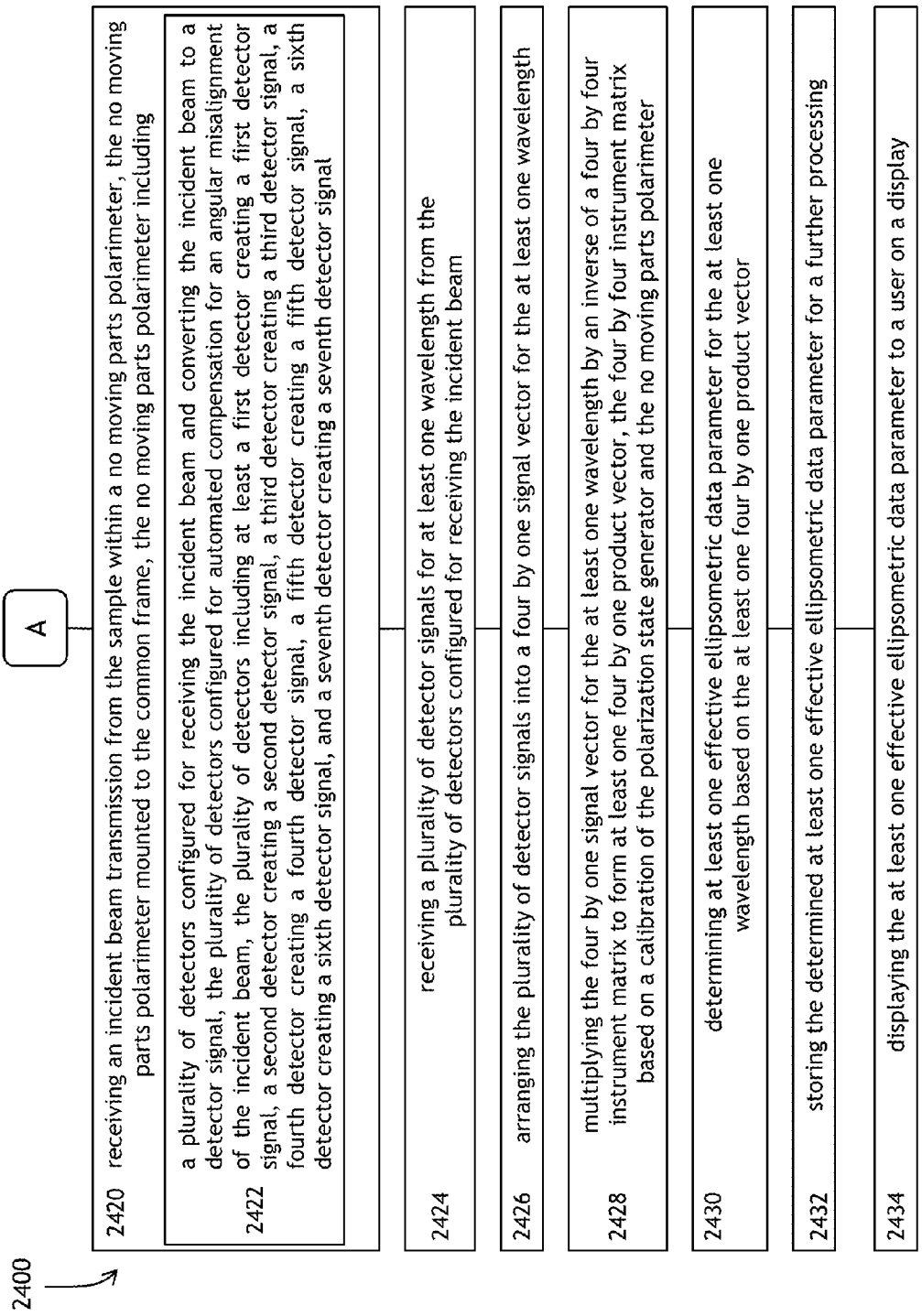

MULTIPLE WAVELENGTH ELLIPSOMETER SYSTEM AND RELATED METHOD

FIELD OF THE INVENTION

The present invention relates generally to ellipsometer and polarimeter systems. More particularly, the present invention relates to a multiple wavelength ellipsometer system for characterizing thin film samples including implementations of a multiple wavelength polarization state generator and a no moving parts polarimeter.

BACKGROUND

Ellipsometry is an optical measurement technique that is commonly used for a wide variety of thin film characterization applications. Fundamentals of ellipsometry, typical instrumentation, data analysis methods, and common applications may be best described in many excellent text books including Ellipsometry and Polarized Light, R. M. A. Azzam and N. M. Bashara, North Holland, 1988, Spectroscopic Ellipsometry and Reflectivty: A User's Guide, H. G. Tompkins and W. A. McGahan, Wiley-Interscience, 1999, Handbook of Ellipsometry, edited by H. G. Tompkins and E. A. Irene, William Andrew, 2006, and Spectroscopic Ellipsometry: Principles and Applications, H. Fujiwara, Wiley, 2007. Typical uses for the ellipsometry technique are measuring thin film thicknesses and optical constants. Monitoring and controlling thin films is critical for many modern technologies, and ellipsometer systems are routinely used for this purpose, both in RECD and for quality control.

Ellipsometry is a non-destructive optical technique that measures two quantities at each wavelength. These two quantities characterize the probing beam polarization state change caused by the sample surface reflection. The traditional ellipsometry expression is show below.

$$Rp/Rs=\tan(\Psi)\exp(i\Delta)$$

Rp and Rs are the complex reflectivities for p- and s-polarized light. The complex ratio Rp/Rs is parameterized by the ellipsometric parameters $\Psi$ and $\Delta$: the magnitude of the complex ratio is $\tan(\Psi)$, and the phase of the complex ratio is $\Delta$. The ellipsometric $\Delta$ parameter provides extreme surface sensitivity, which enables ellipsometers to measure film thickness with sub-nanometer precision. Ellipsometry is not sensitive to the absolute intensity of the measurement beam, as it measures the ratio of p- to s-polarized reflectivity. These are distinct advantages of ellipsometry over the reflectometry technique, which only measures the intensity of the light reflected from the sample. However, ellipsometers are typically complex optical instruments which require expensive polarization optics.

An ellipsometer system generally may include a Polarization State Generator (PSG), a means for supporting the sample being measured, and a Polarization State Detector (PSD). The PSG includes a source of light, which may be monochromatic, polychromatic, or spectroscopic, and may cover any range of the electromagnetic spectrum. The PSG also includes a means for controlling, setting, and/or modulating the polarization state of the light which is emitted from the PSG. The light emitted from the PSG is reflected from or transmitted through the sample being measured. The interaction of the light from the PSG with the sample alters the polarization state of the beam, which is collected by the PSD. The PSD quantifies the polarization state of the light from the sample. As used herein, the terms Polarization State Detector, PSD, and polarimeter are considered interchangeable. Using the known polarization state set by the PSG, and the polarization state of the beam after interacting with the sample as measured by the PSD, the system may calculate ellipsometric data for the sample. The ellipsometric data for the sample may be further analyzed, using well-known methods to determine sample properties of interest, such as film thicknesses, optical constants, surface morphology, etc.

Numerous ellipsometer configurations may have been described in the prior art literature. Ellipsometer configurations differ mainly in the implementations of their PSGs and PSDs. Most modern ellipsometers are photometric instruments which use a modulated signal to improve the speed, precision, and accuracy of the measurement. Rotating element ellipsometers, which incorporate a mechanically rotating optical element in their PSG and/or PSD, have been extensively reviewed in the literature by Collins "Automatic Rotating Element Ellipsometers, Calibration, Operation, and Real Time Applications", R. W. Collins, Review of Scientific Instruments Vol. 61, page 2029, 1990. Exemplary rotating compensator designs are also described in U.S. Pat. No. 5,872,630 and U.S. Pat. No. 6,320,657 B1. Phase modulated systems, which use a piezo-electric transducer to modulate the polarization state of the beam in the PSG and/or PSD, are also common, for example U.S. Pat. No. 5,757,671 and U.S. Pat. No. 5,956,147. However, these Patents prove limited in efficiency as requiring expensive moving parts prone to failure and costly maintenance.

Prior art ellipsometer configurations may be based on division of amplitudes polarimeter design (DOAP) which was first proposed by Azzam "Division-of-amplitude photopolarimeter (DOAP) for the simultaneous measurement of all four Stokes parameters of light", R. M. A. Azzam, Opt. Acta Vol. 29, page 685, 1982. Features of the DOAP design may include no moving parts and four detectors to enable measurement of all four Stokes parameters which fully characterizes the polarization state of a light beam. No moving parts may potentially result in a lower cost, more robust, and higher speed polarization state detector, which may be highly advantageous for certain applications. Given these important advantages, numerous embodiments of the DOAP approach may be found in the prior art. In a DOAP polarization state detector, the light beam is divided into multiple beams by oblique reflections from beam splitters, detectors, or other optical elements. Since the intensity of the divided beams depends on the angle of the incoming beam, prior art DOAP PSD measurement errors may result if the incoming beam angle is not accurately aligned to the polarimeter.

The "classic" DOAP design first envisioned by Azzam uses a coated beam splitter to split the incoming beam into two beams, each of the two beams being further split into two beams by two Wollaston prisms, and the four resulting beam intensities detected by four detectors. Azzam's paper "Single-layer-coated beam splitters for the division-of-amplitude photopolarimeter", R. M. A. Azzam and F. F. Sudradjat, (Applied Optics Vol. 44, No. 2, page 190, 2005) describing a method for designing an optimal coating for the beam splitter. A PSD using this design approach however, requires two expensive Wollaston prisms and an environmentally degradable custom designed and coated beam splitter. Furthermore, the coated beam splitter may be limited further by operation at a single wavelength. As the optimal beam splitter is sensitive to both the coating properties and the angle of incidence, this design is susceptible to measurement errors induced by misalignment of the incoming beam.

Azzam has proposed another method for splitting the incoming beam into multiple beams, based on diffraction from a metallic grating "Division-of-amplitude photopolarimeter based on conical diffraction from a metallic grating", R. M. A. Azzam, (Applied Optics Vol. 31, No. 19, page 3574, 1992). However, since diffraction from a grating is highly angularly dependent, this DOAP embodiment is also highly susceptible to measurement errors induced by misalignment of the incoming beam.

Another DOAP implementation, using only four photodetectors, was proposed by Azzam in U.S. Pat. No. 4,681,450. This design provides a simplistic design with no beam splitters or optical elements required as four photodetectors simultaneously function as polarization dependent beam splitters and detectors. However, optimizing this design requires careful and time consuming orientation of angles and planes of incidences of each detector with respect to the incoming beam, which in turn makes this design highly susceptible to measurement errors induced by misalignment of the incoming beam.

A Patent to Compain and Drevillon U.S. Pat. No. 6,177,995 discloses a DOAP design similar to the "classic" Azzam DOAP, except that the '995 coated beam splitter is replaced by an uncoated prism. The uncoated prism is advantageous in that it may provide optimal polarized separation of the incoming beam in a manner that is relatively independent of both wavelength and beam angle. However, this device may still be relatively expensive to manufacture, as it uses a custom prism cut with specific angles, and two Wollaston prisms. Furthermore, while this design may be optimized to minimize measurement errors due to misalignment of the incoming beam, it suffers from lack of active error compensation.

U.S. Pat. No. 6,836,327 to Yao discloses an in-line optical polarimeter. While this invention does teach the use of polarization-selective elements arranged in an in-line orientation, Yao's device suffers since a substantial portion of the beam is transmitted through the polarimeter, and the device does not provide active correction for beam misalignment.

U.S. Pat. No. 6,177,706 also discloses a polarimeter design which uses multiple polarization sensitive interfaces to split an incoming beam into multiple beams. The '706 configuration suffers from mutual dependent and expensive polarization sensitive interfaces integrally coupled with one or more retardation layers. Similarly, the '706 Patent suffers from measurement errors due to beam misalignment.

U.S. Pat. No. 6,043,887 and U.S. Pat. No. 5,335,066 describe additional embodiments of a beam splitting polarimeter designs. These designs require that the incoming beam is split into two sub-beams, and each sub-beam is further split into two sub-beams. These designs also suffer from measurement errors due to beam misalignment.

U.S. Pat. No. 5,081,348 and U.S. Pat. No. 7,038,776 describe 4 detector polarimeters, but in these designs, the wavefront of the incoming beam is spatially split by optics. This class of polarimeter may be known as a Division of Wavefront Polarimeter (DOWP), and may suffer from errors due to changes in the beam uniformity which may affect the wavefront split.

U.S. Pat. No. 7,800,755 discloses a polarimeter having a multi-wavelength source. However, this design requires Newtonian telescope optics, and the multi-wavelength source is scanned, operatively connected to a fixed waveplate, to convert one polarization state into multiple polarization states.

U.S. Pat. No. 5,548,404 describes an additional multiple wavelength ellipsometer system. In this system, the multiple wavelength light sources are simultaneously modulated, but at different frequencies. To separate the signals from the different light sources, the system employs an expensive and cumbersome synchronous demodulation scheme.

One light source for efficient ellipsometric data measurements may include a well-known light emitting diode (LED). LED's have very long operating lifetimes (>50,000 hours), such that no light source replacement would likely be required over the lifetime of the instrument. Solid state laser diodes may also be used in the PSG. The advantages of laser diodes are a much narrower bandwidth, and higher intensities. However, compared to LED's, the operating lifetime of laser diodes may be much lower (<10,000 hours), and the output beam of a laser diode may be more difficult to collect into a uniform collimated beam. Inexpensive LED's are readily available in a variety of colors in the visible spectral range, and LED's are also available in the UV and NIR spectral ranges (though at an increased cost).

One disadvantage to using LED light sources may be the relatively large spectral bandwidth, which may exceed 30 nm Full Width Half Maximum (FWHM) for some colors of LED's. This large spectral bandwidth may corrupt the data analysis for some samples, especially for thicker films.

Another disadvantage to using LED light sources may be that their emission wavelength may shift versus both ambient temperature and drive current. This behavior may be documented in the datasheets for the devices. The wavelength shift versus temperature may be relatively small (<0.1 nm/° C.), and may be ignored for most typical applications. The wavelength shift versus drive current may be much larger (>10 nm over a typical range in drive currents) and may create variable results without accurate compensation.

An additional disadvantage to using LED light sources may include beam non-uniformities due to the LED die observed in the beam path. The die geometry in the emitting region of the LED may vary for both different LED colors and manufacturers, sometimes resulting in donut-shaped or H-shaped images at certain locations in the beam path.

U.S. Pat. No. 7,061,612 emphasizes the advantages of using a light emitting diode (LED) as light sources in a polarimeter system. This application suffers from single wavelength LED application.

U.S. Pat. No. 7,492,455 discloses a discrete polarization state spectroscopic ellipsometer system. In the '455 Patent, each light source requires an expensive polarization optic associated with it, such that when the light sources are sequentially scanned, discrete polarization states are emitted from the PSG. A single analyzer element within the PSD is limited to a partial analysis of the Stokes vector of the beam.

U.S. Pat. No. 6,034,777 discloses a method for characterizing window retardance in ellipsometer and polarimeter systems. However, the '777 patent requires a spectroscopic ellipsometric data set to simultaneously determine window characterizing and sample characterizing parameters. Another method for characterizing window retardance in ellipsometer systems is discussed in "Windows in ellipsometry measurements", G. E. Jellison, Jr., Applied Optics Vol. 38, No. 22, page 4784, (1999). In this paper, the author suggests that is necessary to measure window characterizing properties with the windows removed from the chamber. However, this approach is inconvenient, and it may also be less accurate, as mounting the windows on the chamber may induce changes in the window characterizing properties.

Therefore a need remains for a system and related method for a multiple wavelength ellipsometer for characterizing thin film samples including efficient implementations of a multiple wavelength PSG and a no moving parts polarimeter.

SUMMARY

Accordingly, one embodiment of the present invention is directed to a polarization state generator, including: a plurality of solid state light sources, the polarization state generator configured to combine an output of the plurality of solid state light sources into a common beam by one of: 1) a cascading arrangement of partially reflective, partially transparent beamsplitters, 2) a diffraction grating oriented to correspond a zero order reflection of the diffraction grating to the common beam, and individual output beams of the plurality of solid state light sources are aligned with one of: a positive order and a negative order of the diffraction grating, a lens configured to collect the common beam and image the common beam on a pinhole, a light diffusing element configured to scramble the common beam, a lens configured to collimate the common beam through the pinhole, an azimuthally rotatable polarizer optic, the azimuthally rotatable polarizer optic azimuthally rotated by one of: a computer controlled motor and a manually rotatable mechanism, and an aperture to define a diameter of the common beam transmitted through the pinhole, a no moving parts polarimeter, including: a first polarimeter section configured to receive an incident beam, the first section including a focusing lens, a second polarimeter section including a first retarder component, a plurality of detectors configured for receiving an incident beam and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal, and a seventh detector D7 creating a seventh detector signal, a third polarimeter section including a first partially reflecting optic oriented to partially reflect the incident beam at a first (+A) angle with respect to the incident beam, the first partially reflecting optic configured to partially reflect the incident beam to the first detector (D1) and to transmit a first remaining incident beam, a fourth polarimeter section including a second partially reflecting optic oriented to partially reflect the first remaining incident beam at a second angle (−A) with respect to the first remaining incident beam, the second partially reflecting optic configured to partially reflect the first remaining incident beam to the second detector (D2) and transmit a second remaining incident beam, a fifth polarimeter section including a second retarder component, a sixth polarimeter section including a third partially reflecting optic oriented to partially reflect the second remaining incident beam at a third angle (+B) with respect to the second remaining incident beam, the third partially reflecting optic configured to partially reflect the second remaining incident beam to the third detector (D3) and transmit a third remaining incident beam, a seventh polarimeter section including a fourth partially reflecting optic oriented to partially reflect the third remaining incident beam at a fourth angle (−B) with respect to the third remaining incident beam, the fourth partially reflecting optic configured to partially reflect the third remaining incident beam to the fourth detector (D4) and transmit a fourth remaining incident beam, an eighth polarimeter section including a third retarder component, a ninth polarimeter section including a fifth partially reflecting optic oriented to partially reflect the fourth remaining incident beam at a fifth angle (+C) with respect to the fourth remaining incident beam, the fifth partially reflecting optic configured to partially reflect the fourth remaining incident beam to the fifth detector (D5) and transmit a fifth remaining incident beam, and a tenth polarimeter section including a sixth partially reflecting optic oriented to partially reflect the fifth remaining incident beam at a sixth angle (−C) with respect to the fifth remaining incident beam, the sixth partially reflecting optic configured to partially reflect the fifth remaining incident beam to the sixth detector (D6) and transmit a sixth remaining incident beam to the seventh detector (D7), a sample housing configured to receive and support a sample, and a common frame configured to receive and orient the polarization state generator, the sample housing, and the no moving parts polarimeter.

An additional embodiment of the present invention may include a device wherein at least one of: the first polarimeter section, the second polarimeter section, the fifth polarimeter section, and the eighth polarimeter section of the no moving parts polarimeter are optionally configured with one of: no focusing lens, no first retarder element, no second retarder element, and no third retarder element.

An additional embodiment of the present invention may include a device wherein the plurality of solid state light sources is four light sources, and the cascading arrangement of partially reflective, partially transparent beamsplitters is implemented by three beamsplitters, a first beamsplitter is configured to combine the individual output beams of a first light source and a second light source into a first common beam, a second beamsplitter is configured to combine the individual output beams from a third light source and a fourth light source into a second common beam, and a third beamsplitter is configured to combine the first common beam and the second common beam.

An additional embodiment of the present invention may include a device wherein the manually rotatable mechanism is an azimuthally rotatable polarizer plate configured to mount with the polarizer optic, the azimuthally rotatable polarizer plate configured to rotatably couple between a front plate and a back plate, said azimuthally rotatable polarizer plate rotatably coupled to the front plate via a bushing, the front plate configured with a plurality of azimuthally spatial detents, the azimuthally rotatable polarized plate further configured with a plurality of azimuthally spatial ball plungers alignable with the azimuthally spatial detents, wherein a user may manually: 1) selectably rotate the azimuthally rotatable polarized plate to cause extraction of at least one ball plunger from at least one detent, 2) selectably rotate the azimuthally rotatable polarizer plate around the bushing to align at least one ball plunger with at least one detent, and 3) selectably rotate the azimuthally rotatable polarized plate to cause insertion of at least one ball plunger into at least one detent to secure the azimuthally rotatable polarizer plate in azimuth with the front plate.

An additional embodiment of the present invention may include a device wherein the partially reflecting optics are uncoated transparent glass plates, and each of the first angle, the third angle, and the fifth angle is 90 degrees positive to each incident beam and each of the second angle, the fourth angle, and the sixth angle is 90 degrees negative from each incident beam.

An additional embodiment of the present invention may include a device wherein the seventh detector D7 is a position sensitive detector.

An additional embodiment of the present invention may include a device further comprising: a plurality of analog circuits configured to combine the detector signal from each of the detectors, wherein a first analog circuit of the plurality of analog circuits is configured to combine the first detector signal D1 and second detector signal D2 to create a first combined signal S1, a second analog circuit of the plurality of analog circuits is configured to combine the third detector signal D3 and the fourth detector signal D4 to create a second combined signal S2, and a third analog circuit of the plurality of analog circuits is configured to combine the fifth detector D5 signal and the sixth detector D6 signal to create a third combined signal S3, and a processor configured to: receive the seventh detector signal D7 and the first S1, second S2, and third S3 combined signals, digitize and store each of the received signals, and configure each of the received signals for a further processing.

An additional embodiment of the present invention may include a device the processor is further configured for control of the plurality of solid state light sources, the control including: sequentially cycling the plurality of solid state light sources through a series of states, each of the series of states including one of: at least one solid state light source illuminated and none of the solid state light source illuminated, receiving the seventh detector signal D7 and the first, second, and third combined signals, digitizing and storing each of the received signals, and configuring each of the received signals for a further processing.

An additional embodiment of the present invention may include a device wherein each partially reflecting optic is configured to mount within a common base, the common base including a plurality of mounting slots in the common base, each of the plurality of mounting slots configured to receive one of the partially reflecting optic, the mounting slots having a mounting surface configured to adhesively couple with a portion of one surface of the partially reflecting optic, the mounting slots sized greater than the partially reflecting optic allowing all surfaces of the partially reflecting optic other than the portion of one surface to remain free from contact with the common base.

An additional embodiment of the present invention may include a device wherein the common frame is further configured for orientation of the multiple wavelength ellipsometer device for a plurality of ellipsometer operations including at least one of: a straight through mode of ellipsometer operation wherein the common beam is directly pointed into the polarimeter, an off sample mode of ellipsometer operation wherein the common beam is: direct toward a sample, and one of: reflected from the sample into the polarimeter, and transmitted through the sample into the polarimeter, and the sample is adjustably mounted to the common frame, and an in situ mode of ellipsometer operation wherein the common frame includes a chamber and the sample is adjustably mounted within the chamber, the chamber having a first window for 1) receiving the common beam and 2) transmitting the received common beam to the sample and a second window for 1) receiving a reflected beam from the sample and 2) transmitting the reflected beam to the polarimeter.

An additional embodiment of the present invention may include a device configured for efficient calibration to determine at least one four by four instrument matrix for at least one wavelength, the calibration comprising the steps of: configuring the multiple wavelength ellipsometer device in the straight through mode, inserting a rotatable calibration waveplate into the common beam path between the polarization state generator and polarimeter, rotating the calibration waveplate to at least two azimuthal orientations, rotating, at each of the at least two azimuthal orientation of the calibration waveplate, the azimuthally rotatable polarizer optic to at least two azimuthal orientations, storing, at each of the at least two azimuthal orientations of the calibration waveplate, and at each of the at least two azimuthal orientations of the azimuthally rotatable polarizer optic, the output signals from the detectors, removing the rotatable calibration waveplate from the common beam path, rotating the polarizer optic in the polarization state generator to at least two azimuthal orientations, storing, at each of the at least two azimuthal orientation of the polarizer optic, the output signals from the detectors, determining, via a non-linear regression analysis and a Mueller matrix model of the device optical components, at least one four by four instrument matrix for at least one wavelength based on: the stored output signals from the detectors, the at least two azimuthal orientations of the polarizer optic, at least two azimuthal orientations of the calibration waveplate, a retardation of the calibration waveplate at each of the at least one wavelength, and at least one non-ideality factor for the polarization state generator.

An additional embodiment of the present invention is directed to a method for acquiring ellipsometric data, comprising: mounting and optionally aligning a sample on a common frame, aligning a polarizer optic within a polarization state generator to an operating azimuthal angle, the polarization state generator mounted to the common frame, the polarization state generator including: a plurality of solid state light sources, the polarization state generator configured to combine an output of the plurality of solid state light sources into a common beam by one of: 1) a cascading arrangement of partially reflective, partially transparent beamsplitters, 2) a diffraction grating oriented to correspond a zero order reflection of the diffraction grating to the common beam, and individual output beams of the plurality of solid state light sources are aligned with one of: a positive order and a negative order of the diffraction grating, a lens configured to collect the common beam and image the common beam on a pinhole, a light diffusing element configured to scramble the common beam, a lens configured to collimate the common beam through the pinhole, an azimuthally rotatable polarizer optic, the azimuthally rotatable polarizer optic azimuthally rotated by one of: a computer controlled motor and a manually rotatable mechanism, and an aperture to define a diameter of the common beam transmitted through the pinhole, directing the common beam toward the sample, the common beam having a common beam path, receiving an incident beam transmission from the sample within a no moving parts polarimeter, the no moving parts polarimeter mounted to the common frame, the no moving parts polarimeter including: a plurality of detectors configured for receiving the incident beam and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal, and a seventh detector D7 creating a seventh detector signal, receiving a plurality of detector signals for at least one wavelength from the plurality of detectors configured for receiving the incident beam, arranging the plurality of detector signals into a four by one signal vector for the at least one wavelength, multiplying the four by one signal vector for the at least one wavelength by an inverse of a four by four instrument matrix to form at least one four by one product vector, the four by four instrument matrix based on a calibration of the polarization state generator and the no moving parts polarimeter, determining at least one effective ellipsometric data parameter for the at least one wavelength based on the at least one four by one product vector, storing the determined at least one effective ellipsometric data parameter for a further processing, and displaying the at least one effective ellipsometric data parameter to a user on a display.

An additional embodiment of the present invention may include a method wherein the calibration of the polarization state generator and the no moving parts polarimeter further includes: determining at least one four by four instrument matrix over a variable range of operating conditions, the variable range of operating conditions including at least one of: a variable drive current of the plurality of solid state light sources, a variable temperature, a variable alignment of the common beam with respect to the no moving parts polarimeter, fitting an element of the four by four instrument matrix to a polynomial function of the variable range of operating conditions, determining at least one variable associated with a current operating condition, determining a four by four instrument matrix for the current operating condition based on at least one polynomial function of the element of the four by four instrument matrix and the at least one variable associated with a current operating condition, configuring the four by four instrument matrix for the current operating condition for operation in acquiring ellipsometric data.

An additional embodiment of the present invention may include a method further including a window accuracy calibration of an in situ mode of ellipsometer operation with at least one window in the common beam path, comprising: determining an optical model for a reference sample by acquiring ellipsometric data on the reference sample without the window in the common beam path, configuring the reference sample and the at least one window in the common beam path on the common frame, determining a window calibration data set by acquiring ellipsometric data on the reference sample at multiple orientations of the azimuthally rotatable polarizer optic, determining 1) at least one ellipsometric N parameter and 2) at least one window-related Mueller matrix element, for at least one wavelength based on the window calibration data set, determining an angle of incidence of the common beam with respect to the reference sample based on the at least one ellipsometric N parameter, determining at least one ellipsometric C parameter and at least one ellipsometric S parameter for the reference sample based on the optical model of the reference sample and the angle of incidence of the common beam, determining at least one window characterizing parameter based on the at least one window-related Mueller matrix element, the at least one ellipsometric N parameter, the at least one ellipsometric C parameter, and at least one ellipsometric S parameter for the reference sample, configuring the at least one window characterizing parameter for use in acquiring ellipsometric data on a subsequent sample to increase an accuracy of the ellipsometric data.

An additional embodiment of the present invention may include a method further including a sample characterization module, comprising: measuring an intensity versus wavelength for each light source of the plurality of solid state light sources, determining an intensity versus wavelength curve for each light source of the plurality of solid state light sources, determining at least one lineshape characterizing parameter for each light source of the plurality of solid state light sources by fitting a piece-wise continuous function with a central Gaussian lineshape and at least one adjacent exponential lineshape to the intensity versus wavelength curve for each light source of the plurality of solid state light sources, building an optical model for the sample, the optical model representative of a nominal structure of the sample, the optical model including a convolution with the fitted piece-wise continuous function with a central Gaussian lineshape and at least one adjacent exponential lineshape calculation, analyzing the ellipsometric data via a non-linear regression analysis with the optical model for the sample to determine at least one sample characterizing parameter, storing the determined at least one sample characterizing parameter for a further processing, and displaying the at least one sample characterizing parameter to a user on a display.

An additional embodiment of the present invention is directed to a multiple wavelength ellipsometer system, comprising: a polarization state generator, including: a plurality of solid state light sources, the polarization state generator configured to combine an output of the plurality of solid state light sources into a common beam by one of: 1) a cascading arrangement of partially reflective, partially transparent beamsplitters, 2) a diffraction grating oriented to correspond a zero order reflection of the diffraction grating to the common beam, and individual output beams of the plurality of solid state light sources are aligned with one of: a positive order and a negative order of the diffraction grating, a lens configured to collect the common beam and image the common beam on a pinhole, a light diffusing element configured to scramble the common beam, a lens configured to collimate the common beam through the pinhole, an azimuthally rotatable polarizer optic, the azimuthally rotatable polarizer optic azimuthally rotated by one of: a computer controlled motor and a manually rotatable mechanism, and an aperture to define a diameter of the common beam transmitted through the pinhole, a no moving parts polarimeter, including: a first polarimeter section configured to receive an incident beam, the first section including a focusing lens, a second polarimeter section including a first retarder component, a plurality of detectors configured for receiving an incident beam and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal, and a seventh detector D7 creating a seventh detector signal, a third polarimeter section including a first partially reflecting optic oriented to partially reflect the incident beam at a first (+A) angle with respect to the incident beam, the first partially reflecting optic configured to partially reflect the incident beam to the first detector (D1) and to transmit a first remaining incident beam, a fourth polarimeter section including a second partially reflecting optic oriented to partially reflect the first remaining incident beam at a second angle (−A) with respect to the first remaining incident beam, the second partially reflecting optic configured to partially reflect the first remaining incident beam to the second detector (D2) and transmit a second remaining incident beam, a fifth polarimeter section including a second retarder component, a sixth polarimeter section including a third partially reflecting optic oriented to partially reflect the second remaining incident beam at a third angle (+B) with respect to the second remaining incident beam, the third partially reflecting optic configured to partially reflect the second remaining incident beam to the third detector (D3) and transmit a third remaining incident beam, a seventh polarimeter section including a fourth partially reflecting optic oriented to partially reflect the third remaining incident beam at a fourth angle (−B) with respect to the third remaining incident beam, the fourth partially reflecting optic configured to partially reflect the third remaining incident beam to the fourth detector (D4) and transmit a fourth remaining incident beam, an eighth polarimeter section including a third retarder component, a ninth polarimeter section including a fifth partially reflecting optic oriented to partially reflect the fourth remaining incident beam at a fifth angle (+C) with respect to the fourth remaining incident beam, the fifth partially reflecting optic configured to partially reflect the fourth remaining incident beam to the fifth detector (D5) and transmit a fifth remaining incident beam, and a tenth polarimeter section including a sixth partially reflecting optic oriented to partially reflect the fifth remaining incident beam at a sixth angle (−C) with respect to the fifth remaining incident beam, the sixth partially reflecting optic configured to partially reflect the fifth remaining incident beam to the sixth detector (D6) and transmit a sixth remaining incident beam to the seventh detector (D7), a sample housing configured to receive and support a sample, and a common frame configured to receive and orient the polarization state generator, the sample housing, and the no moving parts polarimeter.

An additional embodiment of the present invention is directed to a method for acquiring ellipsometric data, comprising: means for generating a common beam from a plurality of solid state light sources within a polarization state generator, means for mounting and optionally aligning a sample, means for receiving an incident beam, the incident beam received from the common beam reflected from the sample, means for automatic compensation for a misalignment of the incident beam, means for measuring, within a polarization state detector, at least one ellipsometric data parameter of the sample, the measuring requiring no moving parts within the polarization state detector, means for analysis of the at least one ellipsometric data parameter, means for determining at least one ellipsometric parameter and at least one sample characterizing parameter based on the analysis means, and means for displaying the at least one ellipsometric parameter and the at least one sample characterizing parameter.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the present invention may be better understood by those skilled in the art by reference to the accompanying figures in which:

FIG. 23 is a table of lineshape characterizing parameters for the LED spectral intensity profiles associated with one embodiment of the present invention; and FIGS. 24A and 24B are a flow diagram of a method acquiring ellipsometric data exemplary of an embodiment of the present invention.

DETAILED DESCRIPTION OF THE INVENTION

One goal of the present invention may include a robust, low cost, easily manufactured multiple wavelength ellipsometer system for use in thin film characterization. This goal may be met by a novel multiple wavelength polarization state generator, which may use sequentially scanned solid state light sources, combined with a no moving parts polarization state detector. The present invention polarization state detector utilizes a paired arrangement of uncoated glass plate beam splitters, and a plurality of detectors, to detect the full polarization state of the beam, while compensating for potential measurement errors that may be induced by misalignment of the incoming beam.

Figure 1:
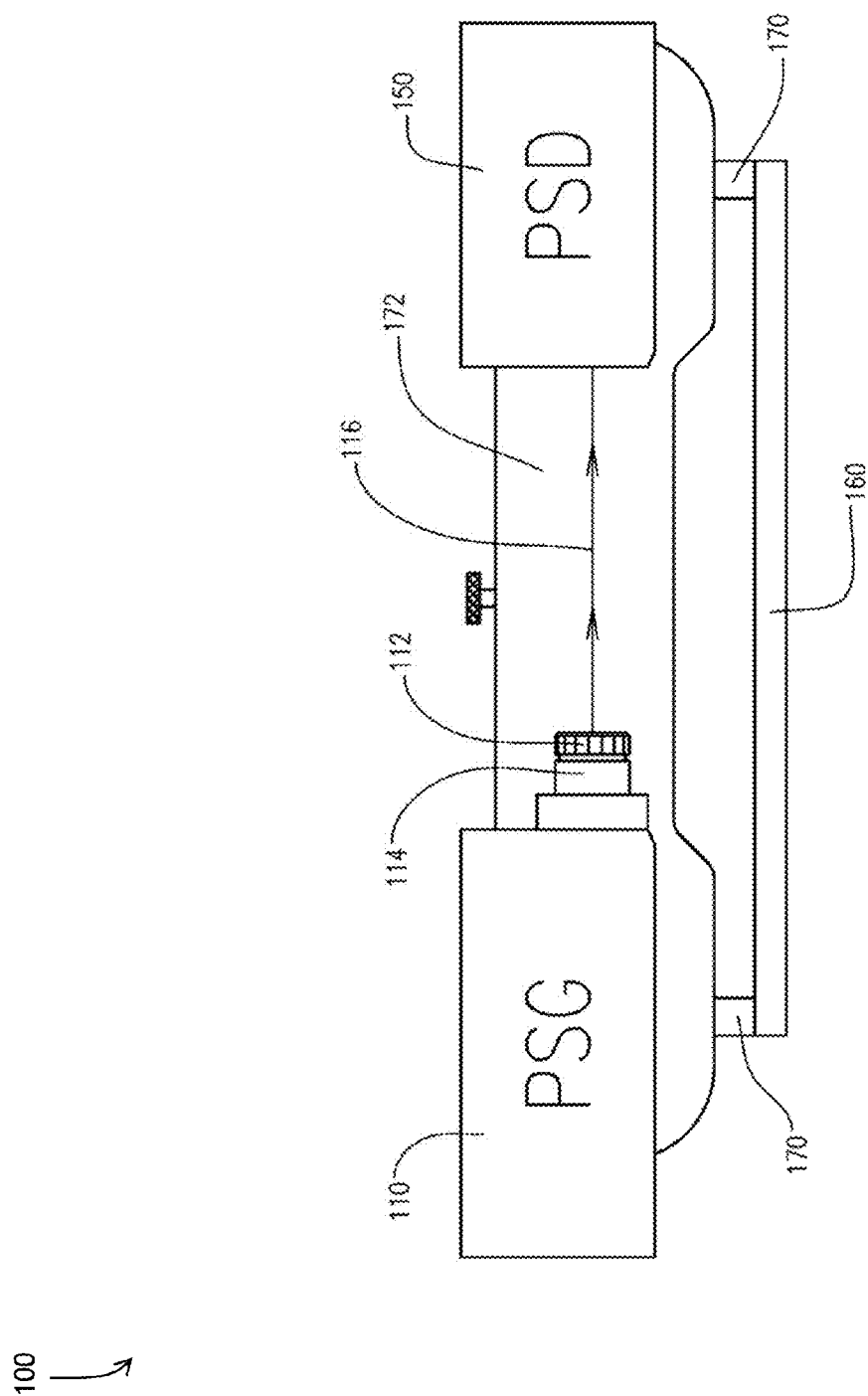
FIG. 1 is a diagram of an ellipsometer system configured in the straight through mode in accordance with an embodiment of the present invention.

The present invention multiple wavelength ellipsometer system may comprise two main components: the Polarization State Generator (PSG), and the Polarization State Detector (PSD). FIG. 1 shows the PSG 110 and PSD 150 mounted to a common frame, configured in the straight through mode of operation. In this mode, the light beam emitted from the PSG 110 (shown as a line with arrows) may be pointed directly into the PSD 150. The non-limiting embodiment in FIG. 1 shows the PSG 110 and PSD 150 fixed to a common back plate 172. PSG 110 may provide a common beam 116 for ellipsometric analysis as discussed below. The common frame may include a back plate 172 connected to a base 160 by vertical supports 170. Also shown in FIG. 1 is a Wave Plate (WP) 114 and WP Rotator 112; these elements are added to the beam path when performing calibration in the straight through mode, as discussed below.

Figure 2:
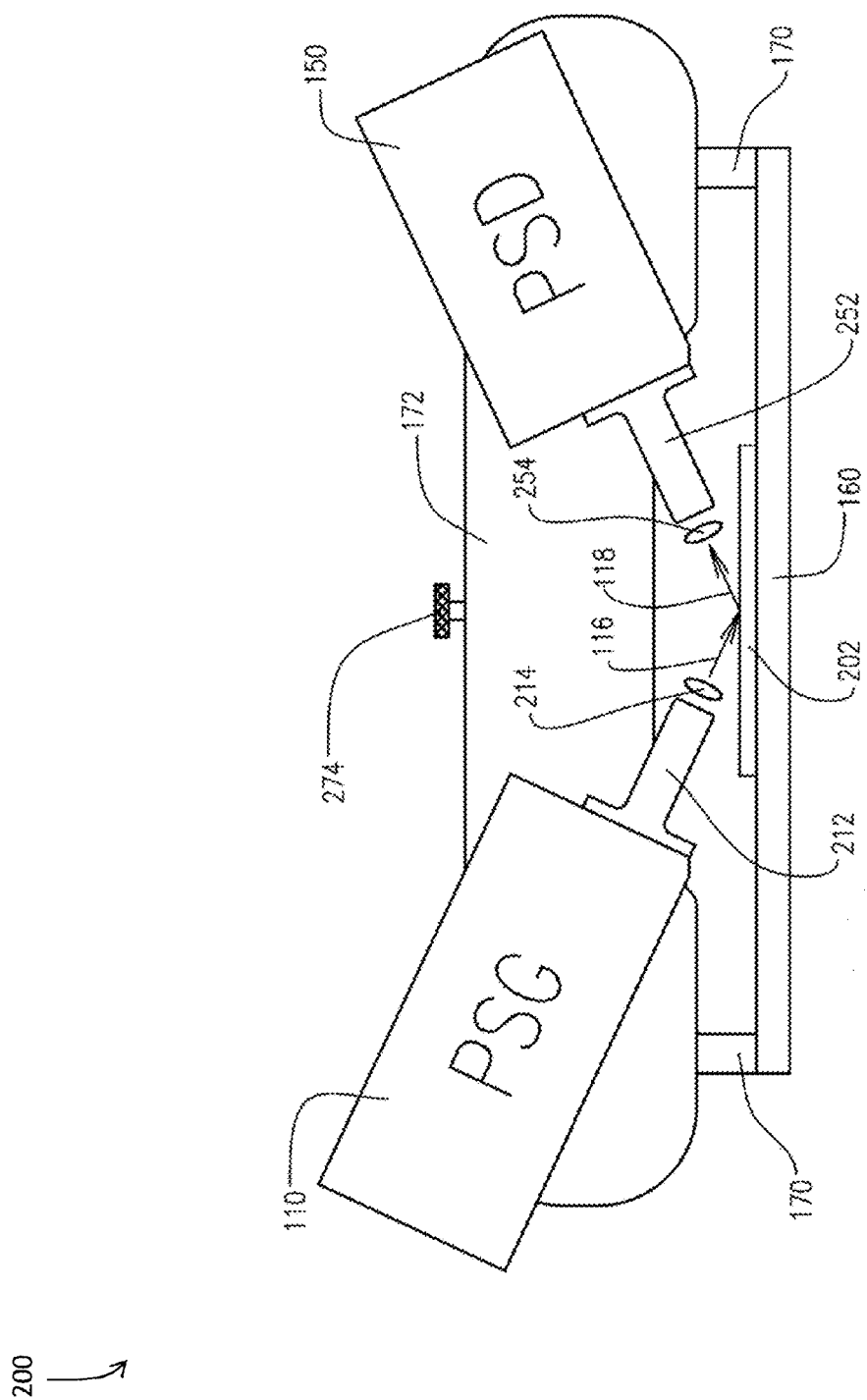
FIG. 2 is a diagram of an ellipsometer system configured in the off sample mode in accordance with an embodiment of the present invention.

FIG. 2 shows the present invention configured in the off sample mode of operation. As in the straight through mode of operation, the PSG 110 and PSD 150 are fixed to a common back plate 172. However, in this mode of operation, the system 200 PSG 110 and PSD 150 are mounted at angles such that the light beam emitted from the PSG 110 may be pointed off a sample, reflected from the sample 202, and enters the PSD 150. The sample 202 rests on a Base plate, the Base may be connected to Vertical Supports, and the Vertical Supports are connected to the back plate 172. If a sliding mechanism is introduced in between the Vertical Supports and the back plate 172, then the height adjustment knob 274 may be used to adjust the height of the PSG 110 and PSD 150 units relative to the sample 202 surface. The procedure of adjusting the height to center the beam reflected from the sample 202 onto the PSD 150 aperture may be known as "aligning the sample" or "sample alignment". The sample 202 alignment procedure may also optionally involve tilting the sample 202 to adjust the angle of the incoming beam to the PSD 150. Also shown in FIG. 2 are lens mounts 212 and 252, focusing lens 214 to focus the common beam 116, and collection lens 254 to focus incident beam 118. These optional elements may be used to reduce the size of the probing light beam on the sample 202 surface.

When the present invention ellipsometer system is operated in the off sample mode, another type of calibration may be required. In the off sample calibration procedure, the azimuthal rotation angles of the PSG 110 and PSD 150 with respect to the sample 202 plane of incidence are determined. The steps for the off sample calibration procedure are: mount and align a sample, rotate the polarizer optic in the PSG 110 to multiple azimuthal orientations, acquire and store raw data at each azimuthal orientation of the polarizer optic, and finally analyze the stored raw data, using non-linear regression analysis with the previously determined 4×4 instrument matrix for the Polarization State Detector and a Mueller Matrix model for the PSG and sample to simultaneously determine the azimuthal rotation angles of the PSG 110 and Polarization State Detector, and the ellipsometric parameters of the sample 202 at each wavelength. In one embodiment, 4 azimuthal angles are used for the polarizer optic (−90°, −45°, 0°, and 45°).

After the present invention ellipsometer system has been calibrated in the straight through and off sample modes, system 200 may acquire accurate ellipsometric data. The steps for acquiring ellipsometric data are: mount and optionally align a sample, set the azimuthal orientation of the polarizer optic in the PSG 110 to the designated orientation for data acquisition, acquire and store raw data at each wavelength, pack the raw data into 4×1 signal vectors at each wavelength, multiply the 4×1 signal vectors at each wavelength times the inverse of the 4×4 instrument matrices at each wavelength to form 4×1 product vectors at each wavelength, calculate the effective ellipsometric data parameters at each wavelength from the 4×1 product vectors at each wavelength, and store the effective ellipsometric data parameters at each wavelength for further processing and display. Note that the calculation of ellipsometric data parameters from the 4×1 product vectors at each wavelength may include other calibration factors, such as the azimuthal rotation angles for the PSG 110 and Polarization State Detector (PSD) 150, which were determined in the off sample calibration procedure. In one embodiment, the designated azimuthal orientation of the polarizer optic for data acquisition may be +45°.

Stress-induced birefringence in windows and lenses which are in the beam path of the ellipsometer system may cause inaccuracies in the measured ellipsometric data. The present invention discloses a method for accurately characterizing and correcting for the effects of windows and lenses in the beam path of the present invention ellipsometer system.

When practicing this method, a reference sample may be separately measured without a window in the beam path to determine the optical model for the reference sample, then the reference sample may be mounted, a windows calibration procedure may be performed, using the previously determined optical model for the reference sample, to determine the angle of incidence of the beam with respect to the sample 202 inside the change and the three window calibration parameters (at each wavelength in the ellipsometer system), and finally, system 200 may acquire accurate ellipsometric data using the three window calibration parameters to correct for the polarization effects of the windows present in the ellipsometer beam path.

After acquiring an ellipsometric Data Set on a sample (said Data Set comprising experimentally measured ellipsometric parameters at multiple wavelengths), system 200 may determine sample parameters of interest, such as film thickness, optical constants, surface morphology, etc., through analysis of the ellipsometric Data Set. One common method of analyzing ellipsometric Data Sets may be to perform a well-known model-based, least squares, non-linear regression analysis of the data set. The present invention overcomes traditional obstacles in the model calculation of analysis to accurately accommodate for the large spectral bandwidth of the LED light sources. This procedure may include the steps of: measuring the intensity spectra of each LED, parameterizing the intensity spectra by a piece-wise continuous functions of Gaussian+Exponential lineshapes, and evaluating the spectral bandwidth convolution integral with the LED lineshape and the incoherent intensity parameters calculated from the optical model.

Figure 3:
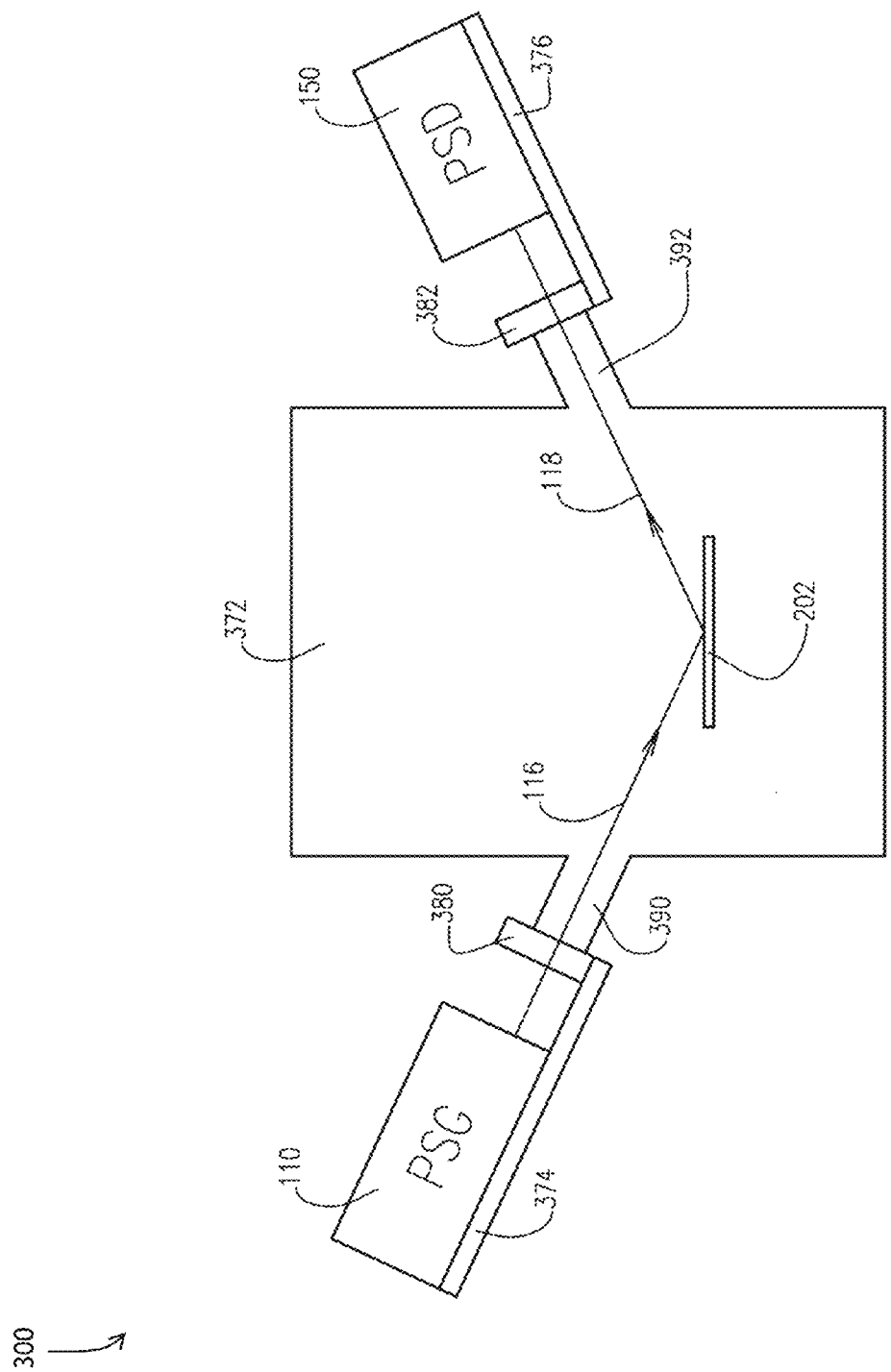
FIG. 3 is a diagram of an ellipsometer system configured in the in situ mode exemplary of an embodiment of the present invention.

FIG. 3 shows an embodiment of the present invention configured for the in situ mode of operation. Chamber 372 may be a vacuum, a liquid cell, and other type of processing chamber. Ports 390, 392 may allow optical access to a sample located inside the chamber 372. The ellipsometer beam exits the PSG 110, passes through a first window 380, passes through a first port 390, reflects off the sample 202, passes through a second port 392, passes through a second window 382, and enters the PSD 150. Mounts 374 and 376 may be used to attach the PSG 110 and PSD 150 to the chamber 372. In one embodiment, mounts 374 and 376 provide tilt adjustments such the beam from the PSG 110 may be pointed onto the sample 202 by adjusting the tilt on 374, and the tilt on 376 may be adjusted to align the PSD 150 with the angle of the incoming beam.

Figure 4:
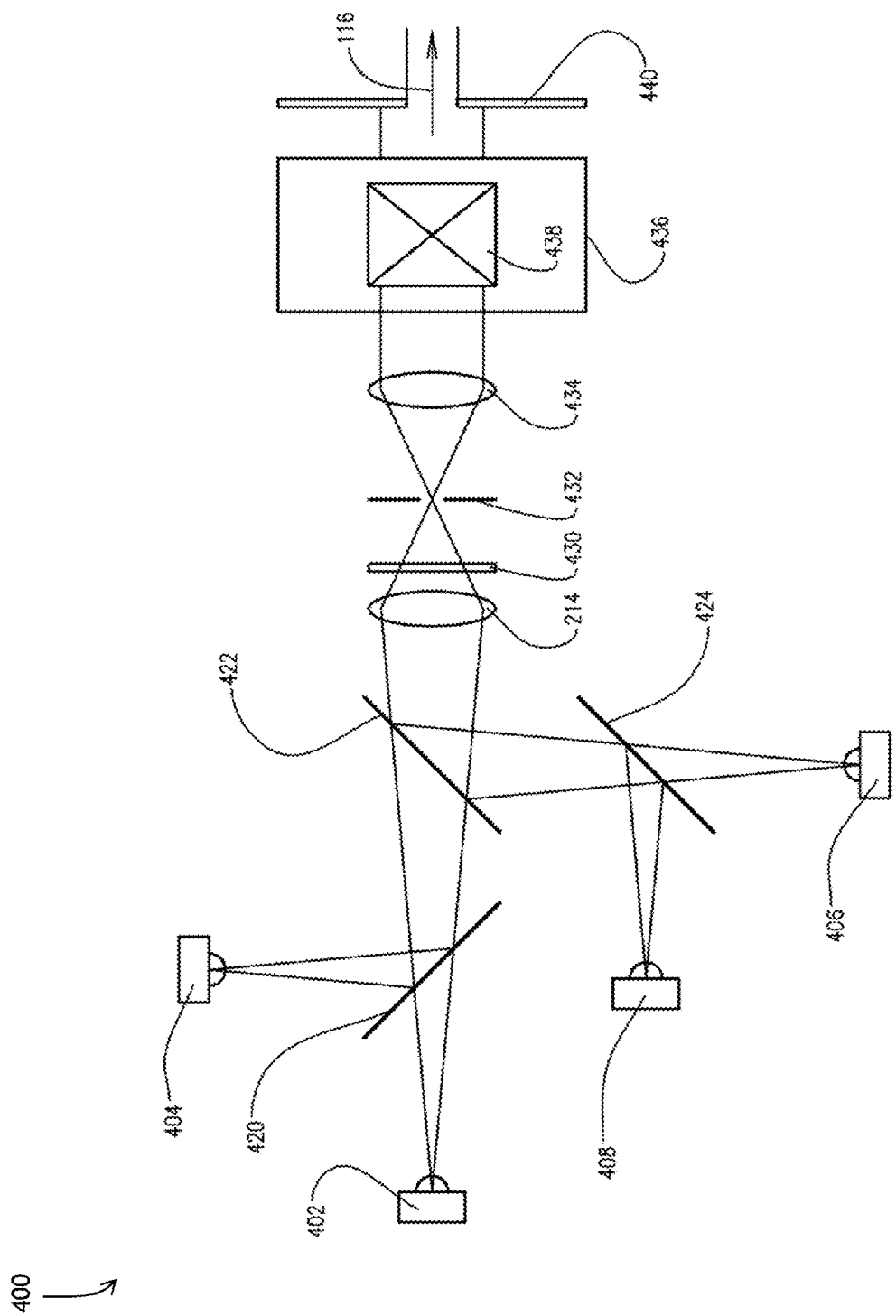
FIG. 4 is an diagram of a Polarization State Generator using beam splitters to combine light from multiple sources into a common beam geometry exemplary of one embodiment of the present invention.

FIG. 4 shows one embodiment of the present invention multiple wavelength PSG 110. This embodiment may use multiple cascading beam splitters, 420, 422, and 424, to combine the light emitted from multiple sources, 402, 404, 406, and 408, into a common beam 116. For best performance, the beam splitters should nominally reflect 50% of the incoming light, and transmit 50% of the incoming light. Well-known commercially available dielectric coated beam splitters are well suited for this task. Lens 214 may be used to image the light emitting regions of the light sources on to a pinhole 432. Light which transmits through the pinhole 432 may be collimated by lens 434. The polarization state of the collimated beam may be set by the polarizer optic 438, which may be mounted in a rotation mechanism 436. Finally, the polarized and collimated beam exits the PSG 110 through an aperture 440. The polarizer optic 438 may use a high quality, but more expensive, crystal polarizer. Sheet polarizers provide more compact and low cost options for the polarizer element. However, if sheet polarizers are used, their non-ideal polarizing properties may have to be accounted for in the instrument calibration procedure. To improve the beam uniformity of the exiting collimated beam, a diffusing film 430 may be inserted into the beam path. While diffusing film 430 may be shown after lens 214 in FIG. 4, it may also be placed before lens 214. While the present invention multiple wavelength light source may be practiced using any number of beam splitters and light sources, one embodiment utilizes 3 beam splitters and 4 light sources for example, a blue 465 nm, a green 525 nm, a yellow 580 nm, and a red 635 nm surface mount LED's.

One embodiment of the present invention may employ an exemplary four LED's for light sources: blue (465 nm), green (525 nm), yellow (580 nm), and red (633 nm). At a slightly increased cost, LED's are also available in the UV and IR spectral ranges, and may also be utilized in the present invention.

Embodiments of the present invention account for the spectral bandwidth of the LED sources in the data analysis procedure by incorporating the effects the LED bandwidth in the data analysis. This procedure may include the steps of measuring the intensity spectra of each LED, parameterizing the intensity spectra by a piece-wise continuous function of Gaussian+Exponential lineshapes, and evaluating the spectral bandwidth convolution integral with the LED lineshape and the incoherent intensity parameters calculated from the optical model.

Embodiments of the present invention may accommodate for the large LED wavelength shift versus temperature by: 1) operating the LED's with the same drive current, and 2) calibrating the PSD 150 vs. LED drive current, and using the calibration values corresponding to the operating drive current during the data acquisition procedure. In addition, embodiments of the present invention may eliminate observed beam non-uniformities by the inclusion of a diffuser element 430 in the PSG 110.

Figure 5:
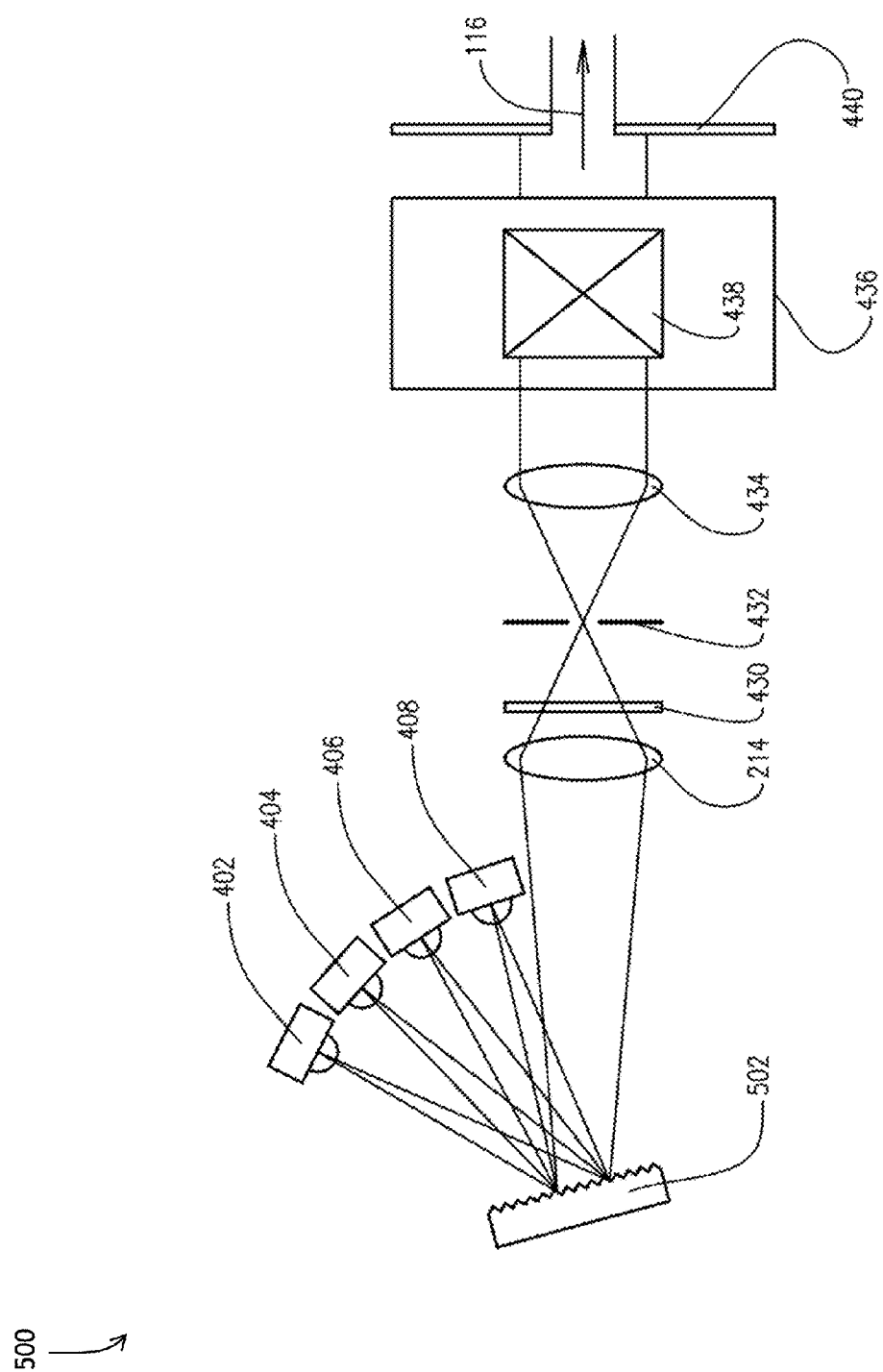
FIG. 5 is a diagram of a Polarization State Generator employing diffraction grating to combine light from multiple sources into a common beam in accordance with one embodiment of the present invention.

FIG. 5 shows an additional embodiment of the present invention multiple wavelength PSG 110. In this embodiment, a diffraction grating 502 may be used to combine the light emitted from the multiple sources 402, 404, 406, and 408 into a common beam 116. The light sources are positioned at angular locations corresponding to the positive and/or negative orders of the diffraction grating 502, while an imaging lens may be positioned to collect the zero order reflection of the diffraction grating 502, and image the light emitting region of each source on to a pinhole 432.

A diffraction grating 502 may be normally operated with incident white light, which may be diffracted into different colors. In the present invention, the diffraction grating 502 operates in reverse, combining multiple colors of light into a common beam 116 of white light. The equation which describes the operation of a diffraction grating 502 is shown below.

$$d(\sin\theta_i + \sin\theta_m) = m\lambda$$

In this equation, d is the grating constant of the grating, m is the order of the diffracted light, $\lambda$ is the wavelength of the light, $\theta_i$ is the angle of the incident light on the grating, and $\theta_m$ is the angle of the diffracted light from the grating 502. In the present invention, the diffraction grating 502 and the sources are angularly positioned such that the grating equation may be satisfied at each wavelength of each source. For example, one non-limiting embodiment may include an arrangement to set $\theta_i=0$, m=1, and d=833 (which corresponds to a 1200 groove/mm grating). Assuming light source wavelengths of 465, 525, 580, and 635 nm, the angular locations of the sources may be 33.9°, 39.1°, 44.1°, and 49.6°. The remaining elements on FIG. 5 are used in a manner identical to those shown and discussed for FIG. 4.

Figure 6:
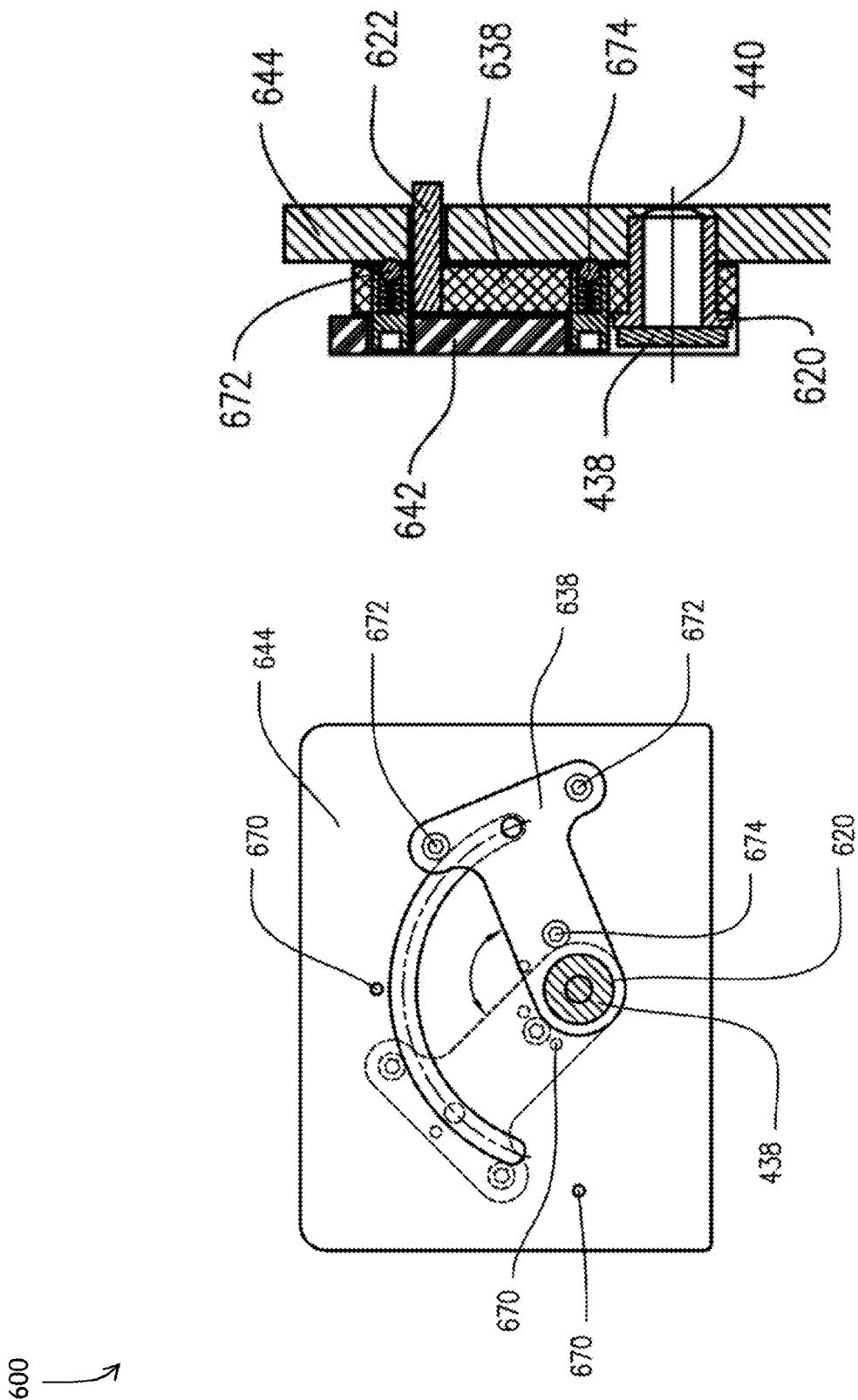
FIGS. 6A and 6B are diagrams of an exemplary manual polarizer rotation mechanism in accordance with one embodiment of the present invention.

The rotatable polarizer 438 in the PSG 110 may be fixed during normal operation of the instrument, but it may also be rotated to discrete azimuthal orientations during the instrument calibration procedure. The rotation mechanism 436 for the polarizer element 438, may be implemented by a motorized mount and controlled by a processor. A more compact and economical manual polarizer rotation mechanism is disclosed in FIGS. 6A and 6B. The manual rotation mechanism 600 for the polarizer element 438 may be implemented by a 3 plate design, as shown by the side view in FIG. 6B. The polarizer plate 638 may be supported between a rotation mechanism back plate 642 and rotation mechanism front plate 644. The polarizer element 438 may be fixed to the polarizer plate 638, as is a bushing 620. The bushing 620 may be inserted into a hole in the rotation mechanism front plate 644, which may be also concentric with the light beam exiting aperture 440. The bushing 620 allows the polarizer plate 638 to pivot about the hole, thereby azimuthally rotating the polarizer element 438.

Ball plungers 672 and 674 push the polarizer plate 638 against the rotation mechanism back plate 642. A lever 622 allows external manual adjustments of the polarizer element 438 azimuthal orientation. To provide discrete and repeatable azimuthal orientations for the polarizer plate 638, a pattern of detent holes 670 may be placed on the rotation mechanism front plate 644, and ball plungers 672 and 674 are attached to the polarizer plate 638, such that the spacing of the ball plungers 672 and 674 on the polarizer plate 638 line up with the detent holes 670 on the rotation mechanism front plate 644 only at appropriately chosen, discrete azimuthal orientations of the polarizer plate 638. This is shown schematically in FIG. 6A, which shows a back view of the polarizer rotation mechanism 600, but with the rotation mechanism back plate 642 removed for clarity. In one embodiment, detent holes are placed to provide four azimuthal orientations of the polarizer at −90°, −45°, 0°, and 45°.

Figure 7:
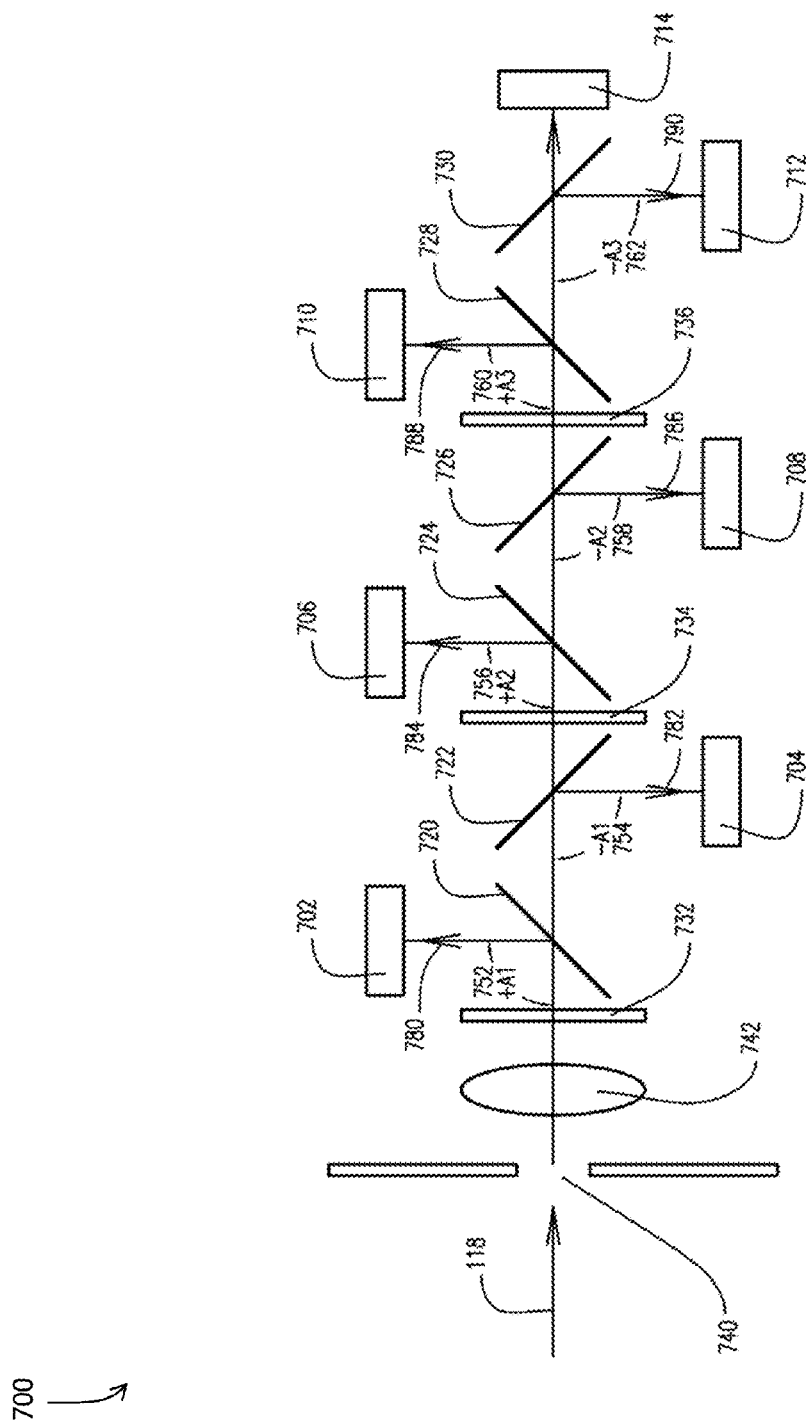
FIG. 7 a diagram of a Polarization State Detector showing paired arrangement of beam splitters and detectors associated with one embodiment of the present invention.

FIG. 7 shows a schematic representation of one embodiment of the present invention including a no moving parts PSD 150. The incident beam 118 enters the PSD 150 through an aperture 740. One design element of the present invention PSD 150 may be the paired arrangement of beam splitters and detectors. As shown in FIG. 7, incident beam 118 may be partially reflected by first beam splitter 720 into first detector 702. The angle between the incoming and reflected beams 780 is +A1 752. The remaining beam transmits through first beam splitter 720 and may be partially reflected by second beam splitter 722 into second detector 704. The angle between the incoming and reflected 782 beams for this second partial reflection is −A1 754. While the angle of incidence for the reflections from first beam splitter 720 and 722 are nominally the same, the beams are reflected in opposite directions, and hence the negative sign for the second partial reflection. Beam splitter 720 and 722 form one beam splitter pair, and their resulting partially reflected beams are collected by the detector pair of first detector 702 and second detector 704. Summing the signals from the first detector 702 and second detector 704 detector pair, by one of: an analog circuit and by digitizing the signals and summing them with a processor, results in a signal S1 that may be insensitive to angular misalignments in the incoming beam, as outlined below.

The beam transmitted through second beam splitter 722 interacts with a second beam splitter pair comprising third beam splitter 724 and fourth beam splitter 726, each of which partially reflect the beam into a pair of detectors third detector 706 and fourth detector 708. The angles between the incident beam 118 and the partially reflected beams 784, 786 entering third detector 706 and fourth detector 708 are +A2 756 and −A2 758. The signals from the second detector pair, third detector 706 and fourth detector 708, are summed into a signal S2. The beam transmitted through fourth beam splitter 726 interacts with a third beam splitter pair, comprising fifth beam splitter 728 and sixth beam splitter 730, each of which partially reflect the beam 788, 790 into a pair of detectors fifth detector 710 and sixth detector 712. The angles between the incident beam 118 and the partially reflected beams 788, 790 entering fifth detector 710 and sixth detector 712 are +A3 760 and −A3 762. The signals from the third detector pair, fifth detector 710 and sixth detector 712, are summed into a signal S3. The remaining beam which may be transmitted through sixth beam splitter 730 may be collected by seventh detector 714.

In one embodiment, seventh detector 714 may be a 2-dimensional Position Sensitive Detector. Well-known 2-dimensional Position Sensitive Detectors may have four output signals (X1, Y1, X2, Y2) which may be processed into the x,y location where the beam hits the Position Sensitive Detector. Using the distance between the aperture 740 and seventh detector 714, the x,y location from the Position Sensitive Detector may be converted into an angular measure of the incident beam 118 with respect to the Polarization State Detector by using simple trigonometry. Lens 742 may optionally be placed in the beam path after the aperture to focus the beam on the Position Sensitive Detector, which may improve the accuracy of the angular measurement of the incoming beam. The average value of the output signals from the Position Sensitive Detector, (X1+Y1+X2+Y2)/4, may be stored as a signal S4. To provide sensitivity to different polarization components of the incoming beam, one or more of the beam splitter and detector pairs may be azimuthally rotated about the beam axis. Another way to provide sensitivity to different polarization components of the incident beam 118 may be to add optical elements which introduce a relative phase shift between polarized components of light before one or more of the beam splitter and detector pairs. Such phase shifting optical elements are known as retarders, and waveplates and Fresnel rhombs are two common types of retarders. Optional waveplates 732, 734, and 736 are shown in FIG. 7. In one embodiment, a first waveplate may be present between 722 and third beam splitter 724 (corresponding to waveplate 734), and a second waveplate may be present between fourth beam splitter 726 and fifth beam splitter 728 (corresponding to waveplate 736). Optimal values for the fast axis orientations and retardances of the waveplates are discussed below.

A preferred embodiment of the present invention PSD 150 may actively compensate for misalignments of an incoming beam. This compensation may be effected by employing a paired arrangement of beam splitters and detectors. For example, the incident beam 118 hits the first beam splitter, and may be partially reflected at an angle +A (measured with respect to the incoming beam) into a first detector. The beam transmitted through the first beam splitter may be partially reflected at an angle −A (measured with respect to the incoming beam) by a second beam splitter into a second detector. The signals from the first and second detectors are added by one of: an analog circuit and by digitizing the signals and adding them in a processor. If the angle of the incident beam 118 may be increased slightly, the angle of incidence on the first beam splitter may also increase slightly, while the angle of incidence on the second beam splitter may decrease slightly. Likewise, if the angle of the incident beam 118 may be decreased slightly, the angle of incidence on the first beam splitter may also decrease slightly, while the angle of incidence on the second beam splitter may increase slightly. Since the reflection and transmission properties of the beam splitters are approximately linear over a small angle range, the sum of the signals from the detector pair may remain constant, at least to the first order, even if the angle of the incident beam 118 may be changed slightly. In this manner, misalignment of the incident beam 118 may be compensated by the paired arrangement of beam splitters and detectors in the present invention.

The PSD 150 of the present invention may exemplarily use three pairs of beam splitters and detectors, for an exemplary total of six beam splitters and six detectors. The beam splitters may utilize any type of partially reflecting, partially transmitting device, including cube beam splitters and plate beam splitters with custom coatings. Beam splitters in the present invention may preferably include uncoated glass plates, which may be fabricated using common optical materials such as BK7 glass and fused silica. Uncoated glass plates are inexpensive, more likely to be environmentally stable, and also provide relatively achromat reflection and transmission characteristics. To overcome the DOAP design challenge of poor balance in detector intensity, the present invention sums the intensities from the paired beam splitters and detectors and provides an improved balance in detector intensity.

To accurately determine the polarization state of the incoming beam, each detector pair must be sensitive to linearly independent components of the polarization state. An ideal uncoated glass plate beam splitter does not introduce any retardance into the reflected and transmitted beams, but according to the Fresnel equations, it does reflect and transmit p- and s-polarized light differently, enabling it to act as a partial polarizer. To detect a different polarization component, the plane of incidence a beam splitter pair may be azimuthally rotated about the beam. However, such azimuthal rotation may greatly complicate the mounting mechanism for the beam splitters. Inserting retardation elements in between the beam splitter pairs may be another way to produce sensitivity to different polarization components. In one embodiment of the present invention, a first waveplate may be inserted in the beam path between the first and second beam splitter pairs, and a second waveplate may be inserted in the beam path between the second and third beam splitter pairs. In another embodiment of the present invention, the first, second, and third beam splitter pairs may be all azimuthally rotated to specified orientations, and a Fresnel Rhomb may be inserted as a retardation element in between the second and third beam splitter pairs.

In the present invention PSD 150, a seventh detector may be used to collect the remaining beam which may be transmitted through all the beam splitters. The seventh detector may be preferably a position sensitive detector, the outputs of which may be used to determine the angle of the incident beam 118 with respect to the PSD 150. An optional lens may be placed after the entrance aperture of PSD 150 to focus the beam on the seventh detector, which may improve the accuracy of the position state detector, especially in the presence of non-uniformity of the incoming beam. The optional lens in the PSD 150 may also generate a range of incidence angles on the beam splitters. To overcome the DOAP challenge of a range of incidence angles, which may induce measurement errors, and such errors are further increased in the presence of beam non-uniformity, embodiments of the present invention employ the paired arrangement of beam splitters to compensate for potential errors induced by a range of incidence angles on the beam splitters as well as beam non-uniformity on the beam splitters.

In one embodiment, the angles on FIG. 7 as A1, A2, and A3 are all set to nominally 90°. The corresponding Angle of Incidence of the beam with respect to the surface normal of the beam splitters is therefore 45°. In addition to simplifying the layout of the optical elements, unwanted signals may be eliminated from possible collection by the detectors.

Figure 8:
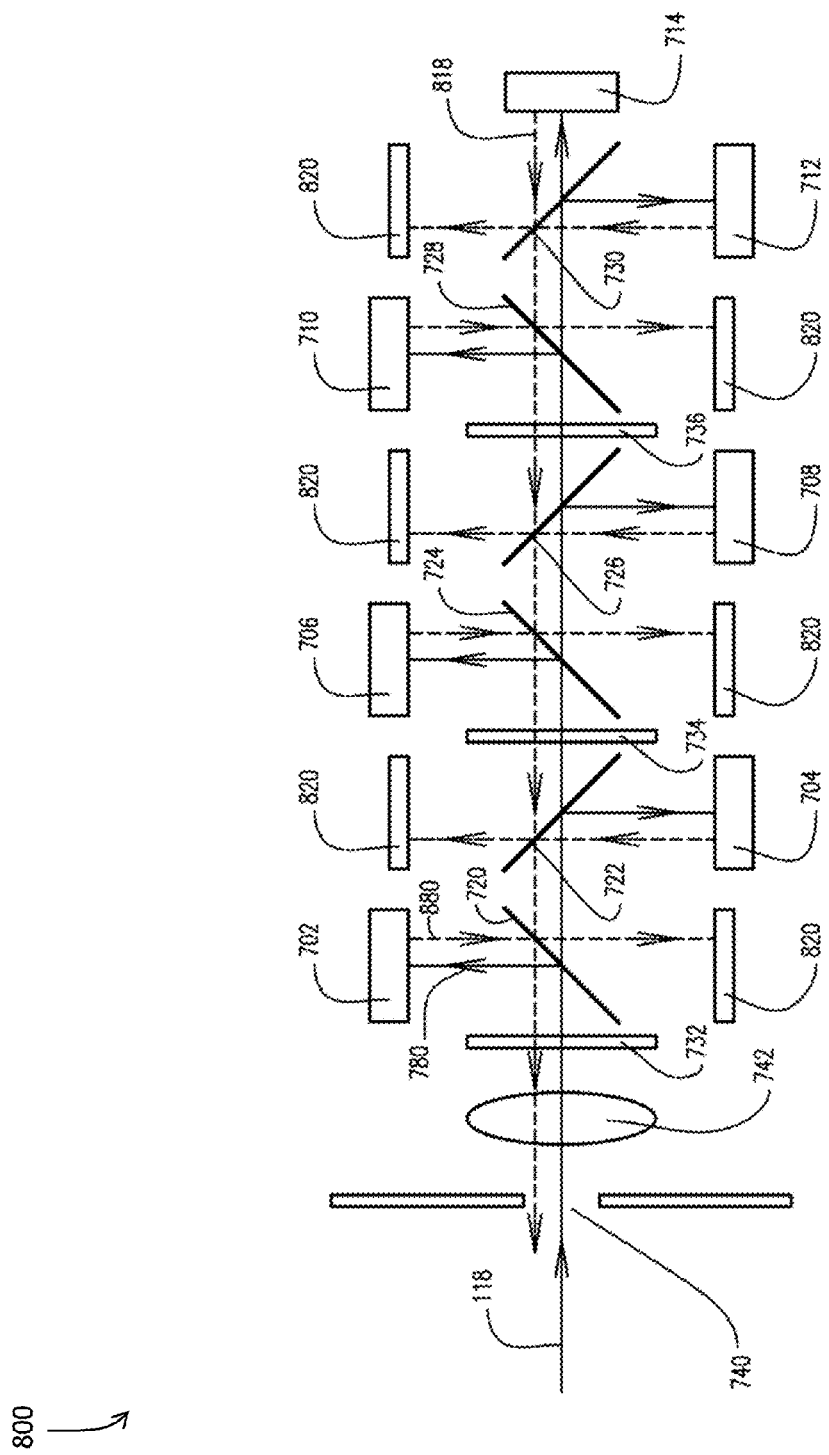
FIG. 8 is a diagram of a Polarization State Detector showing back reflected beams from the detectors and waveplates directed to beam dumps exemplary of one embodiment of the present invention.

In FIG. 8, the back reflections from the detector elements first detector 702, second detector 704, third detector 706, fourth detector 708, fifth detector 710, sixth detector 712, and seventh detector 714, and from the waveplates 732, 734, and 736, are shown as dashed lines (which are offset from the primary beam path solid lines for clarity). Due to the geometry of the layout, all the partial reflections from the beam splitters 720, 722, 724, 726, 728, and 730, of the back reflected beams 880 from the detectors first detector 702, second detector 704, third detector 706, fourth detector 708, fifth detector 710, sixth detector 712, and seventh detector 714 and waveplates 734 and 736, are directed into beam dumps 820. The back reflected beams 818, 880 do not enter any of the detectors, thereby preventing any collection of unwanted beams and signals. The beam dumps 820 may be readily implemented by black flocking paper, and any well-known light absorbing material.

While the beam splitters used in the PSD 150 may be any type of partially reflecting, partially transmitting device, including cube beam splitters and plate beam splitters with custom coatings, one embodiment beam splitters in the present invention are uncoated glass plates, which may be fabricated using common optical materials such as BK7 glass and fused silica.

Figure 9:
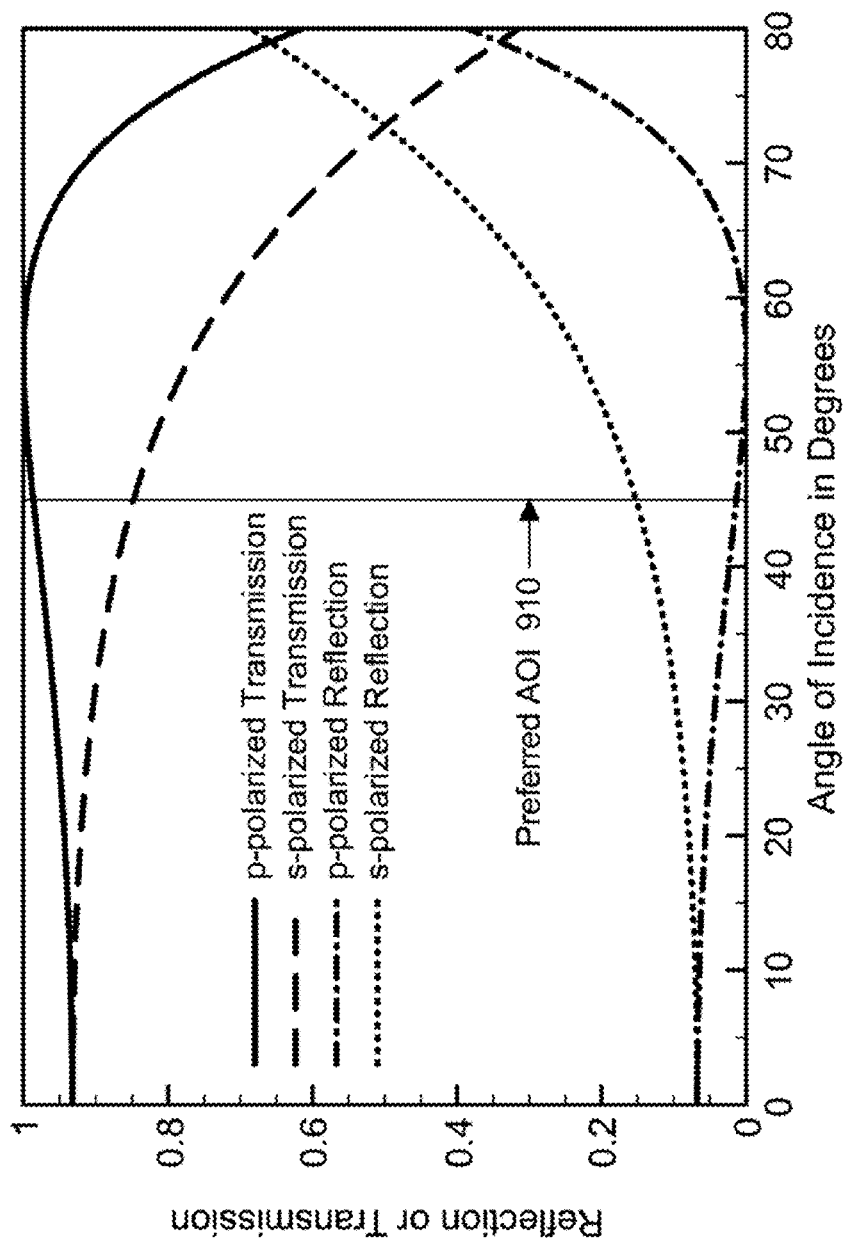
FIG. 9 is a graph of polarized reflection and transmission curves for an uncoated fused silica glass plate vs. angle of incidence exemplary of one embodiment of the present invention.

FIG. 9 shows the reflected and transmitted light from a fused silica glass plate vs. Angle of Incidence (AOI). The wavelength used for the calculation was 546 nm; for fused silica, the corresponding index of refraction is 1.46. One noteworthy feature on the graph in FIG. 9 may be that the p-polarized reflection curve goes to zero near 55 degrees Angle of Incidence. This angle of minimum reflectivity may be known as the "Brewster's Angle" (s-polarized light does not exhibit this effect). As previously stated, one Angle of Incidence (AOI) 910 for the beam splitters is 45°, which may be indicated by the vertical line in FIG. 9. At 45°, the p- and s-polarized transmission values are 0.986 and 0.847, and the p- and s-polarized reflection values are 0.014 and 0.153. The ratio between s- and p-reflectivity may be ≈11, so a fused silica beam splitter operated at 45° may not be a very effective polarizer. However, even this relatively low reflectivity contrast for polarized light may provide adequate sensitivity for the polarimeter, as derived below.

Figure 10:
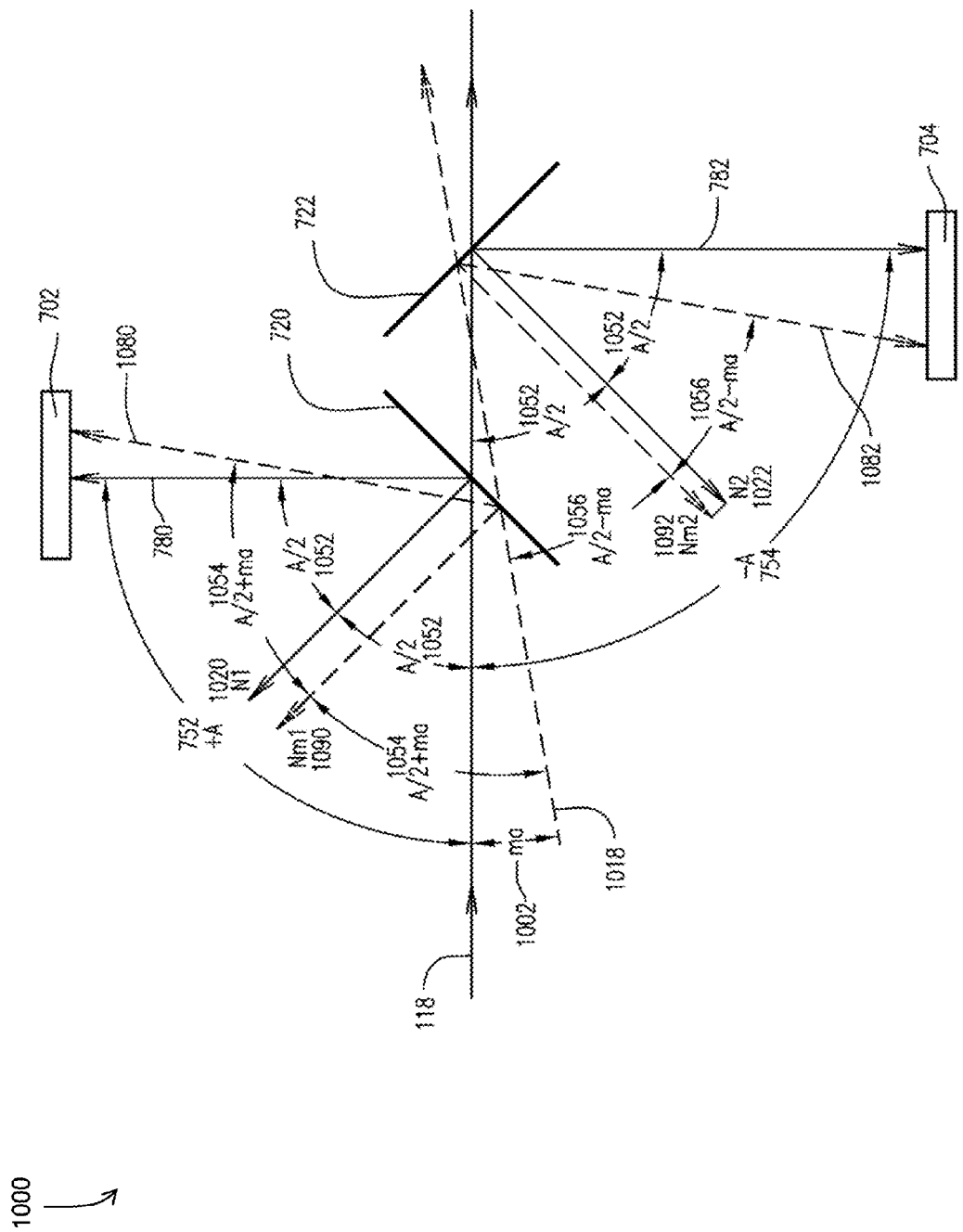
FIG. 10 is a diagram of reflection of aligned and misaligned beams associated with one embodiment of the present invention.

FIG. 10 may clarify how the system 100 paired arrangement of beam splitters may compensate for beam misalignment errors. In FIG. 10, the incident beam 118 (drawn as a solid line, with arrows) reflects from a pair of beam splitters 720 and 722. The angle between the Incident beam 118 and the beam reflected 780 from first beam splitter 720 into first detector 702 may be +A 752. The angle between the Incident beam 118 and beam reflected 782 from second beam splitter 722 into second detector 704 may be −A 754. The surface normals to the beam splitters are N1 1020 and N2 1022. The angles of incidence and the angles of reflection, which are measured with respect to the surface normals, are A/2 1052 for both first 720 and second 722 beam splitters. A misaligned beam 1018 is shown as a dashed line with arrows. The angle of the misaligned beam with respect to the ideal (aligned) Incident beam 118 is ma 1002. Note that the misalignment here has been greatly exaggerated for the purpose of clarity; in actual operation the misalignment may typically be less than 1 degree. Surface normals for the beam splitters, drawn at the intersection of the beam splitters with the misaligned beam, are Nm1 1090 and Nm2 1092. From simple geometry, it may be obvious that the angles of incidence and reflection for the misaligned beam 1080 with first beam splitter 720 are A/2+ma 1054, while the angles of incidence and reflection for the misaligned beam 1082 with second beam splitter 722 are A/2−ma 1056. The angle of incidence changes due to a change in beam alignment are opposite for the beam splitters which are paired in this geometry. As the reflection and transmission properties vs. Angle of Incidence are approximately linear for small angle changes near 45° (see FIG. 9), the total reflected and transmitted light intensities for the beam splitter pair may be approximately constant for small changes in the alignment of the incident beam 118.

To simplify the manufacturing of the present invention Polarization State Detector, FIGS. 11A-11D indicate a method of mounting the plurality of optical elements. The optical layout of the Polarization State Detector, as shown in FIGS. 7 and 8, may be implemented by mounting all of the beam splitter and waveplate optical elements into mounting slots located on a common base plate 1110. The mounting slots may be efficiently machined by a computer controlled CNC machine, which enables very accurate and precise control of their positions, angles, and depths.

In one embodiment, slots for mounting the optical elements to the common base plate are illustrated by FIGS. 11A, 11B, 11C, and 11D.

Figure 11B:
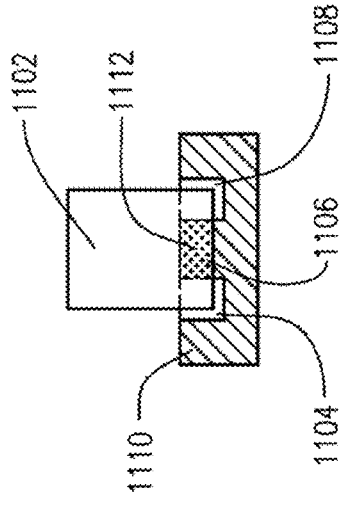
FIG. 11A-11D are diagrams of optical element and associated slot in accordance with one embodiment of the present invention.
Figure 11D:
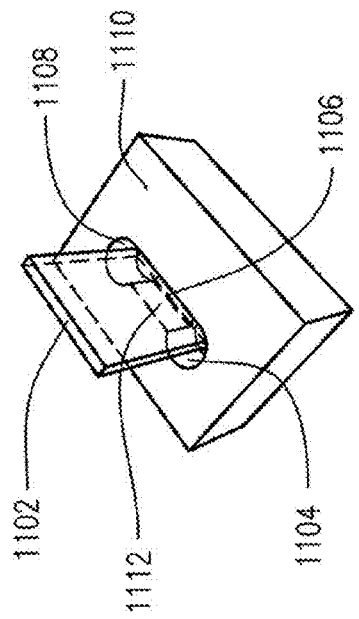
Figure 11A:
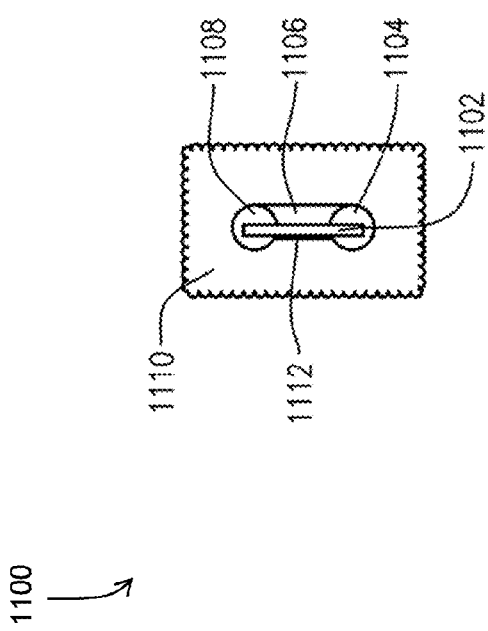
Figure 11C:
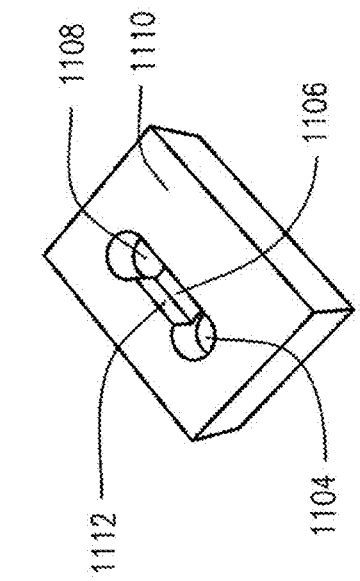

FIG. 11A shows a top view of a mounting slot. The mounting slot within common base plate 1110 may include of three pockets 1104, 1106, and 1108. Pockets 1104 and 1108 are wider than pocket 1106, such that the optical element 1102 does not contact the walls of pockets 1104 and 1108. The optical element 1102 may be glued to the wall of pocket 1106 by a glue pad 1112. FIG. 11B shows a side view of a mounting slot. Note that the depth of pockets 1104 and 1108 may be deeper than pocket 1106, which prevents the optical element 1102 from contacting the bottom of pockets 1104 and 1108. The optical element 1102 may rest on the bottom of pocket 1106, and may be adhesively attached to a side wall of pocket 1106 by a glue pad 1112. To further illustrate the geometry of one embodiment mounting slots, isometric views of a mounting slot are shown in FIG. 11C (without an optical element) and in FIG. 11D (with an optical element). The geometry of one embodiment mounting slots minimizes the surface contact area between the optical element 1102 and the common base plate 1110, which reduces any potential mounting strain on the optical element. Furthermore, the glue used for glue pad 1112 may be also chosen to minimize mounting strain on the optical element.

Figure 12:
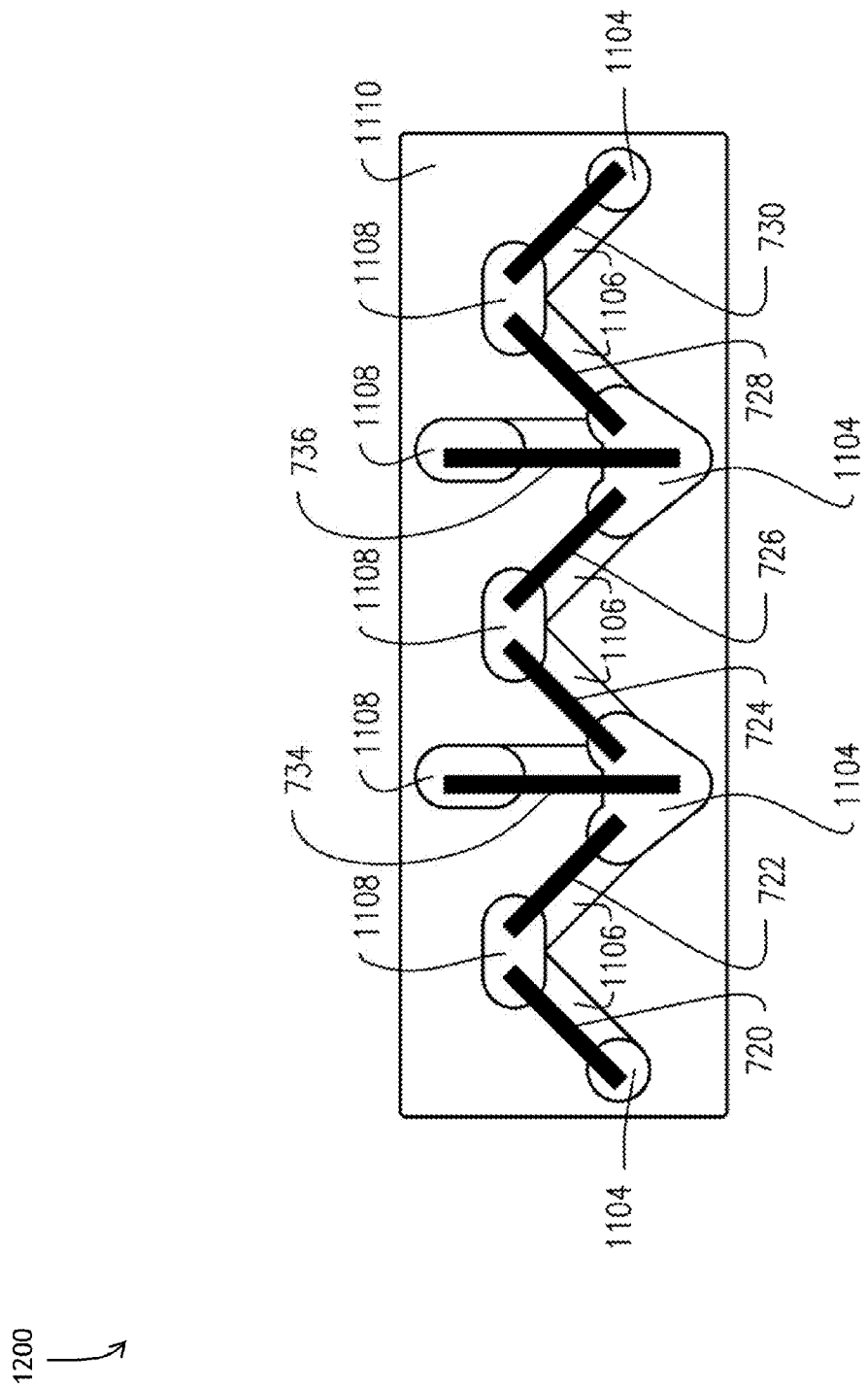
FIG. 12 is a top view of one embodiment of the present invention.
Figure 13:
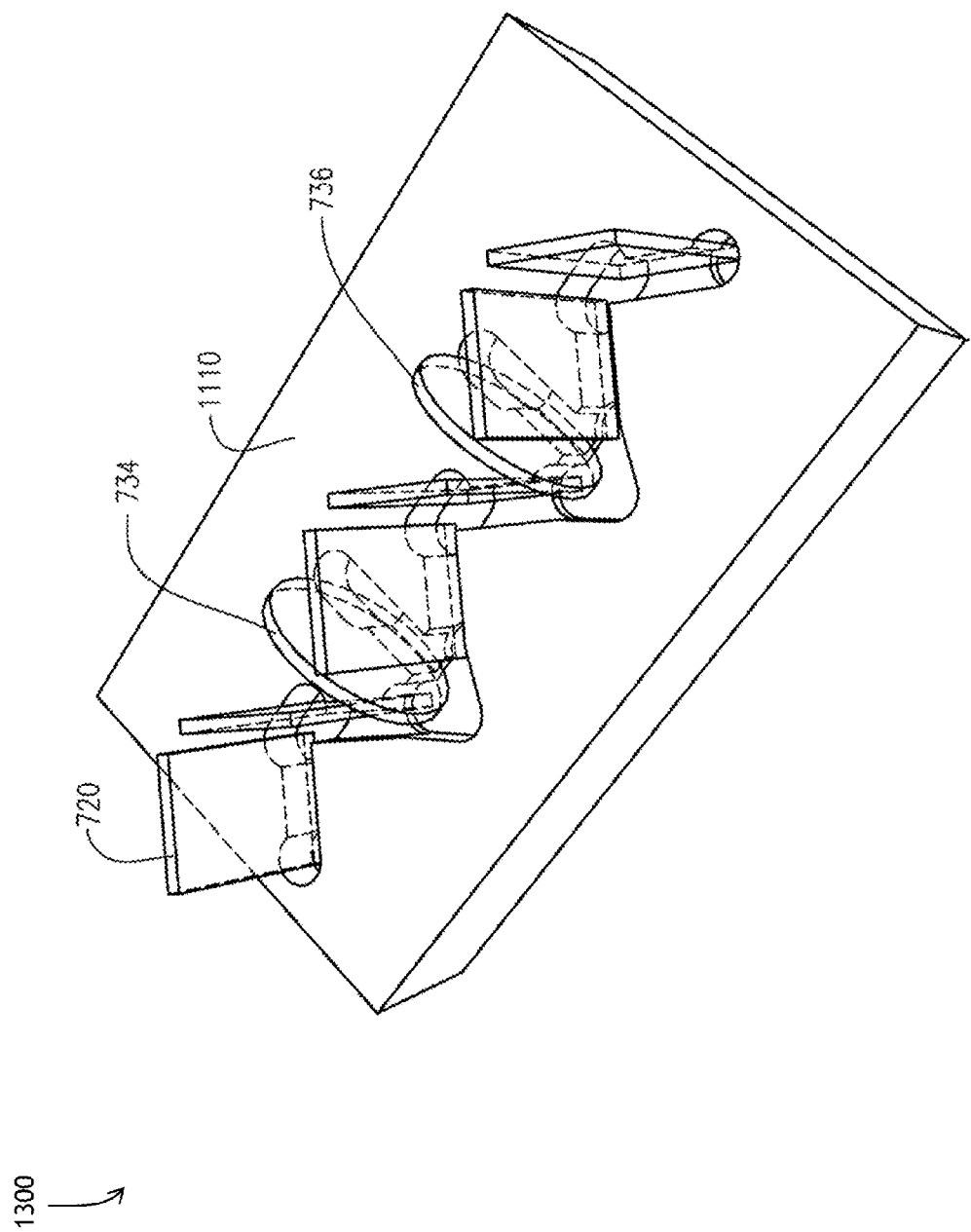
FIG. 13 is a isometric view of one embodiment of the present invention.

FIG. 12 shows a top view of all the optical elements mounted to a common base plate using one embodiment mounting slot design. Note that deeper pockets 1104 and 1108 have been merged together for adjacent optical components to enable a more compact layout. FIG. 13 shows an isometric view of the 6 beam splitters and 2 waveplates mounted on a common base 1110, using one embodiment mounting slot design.

Figure 14:
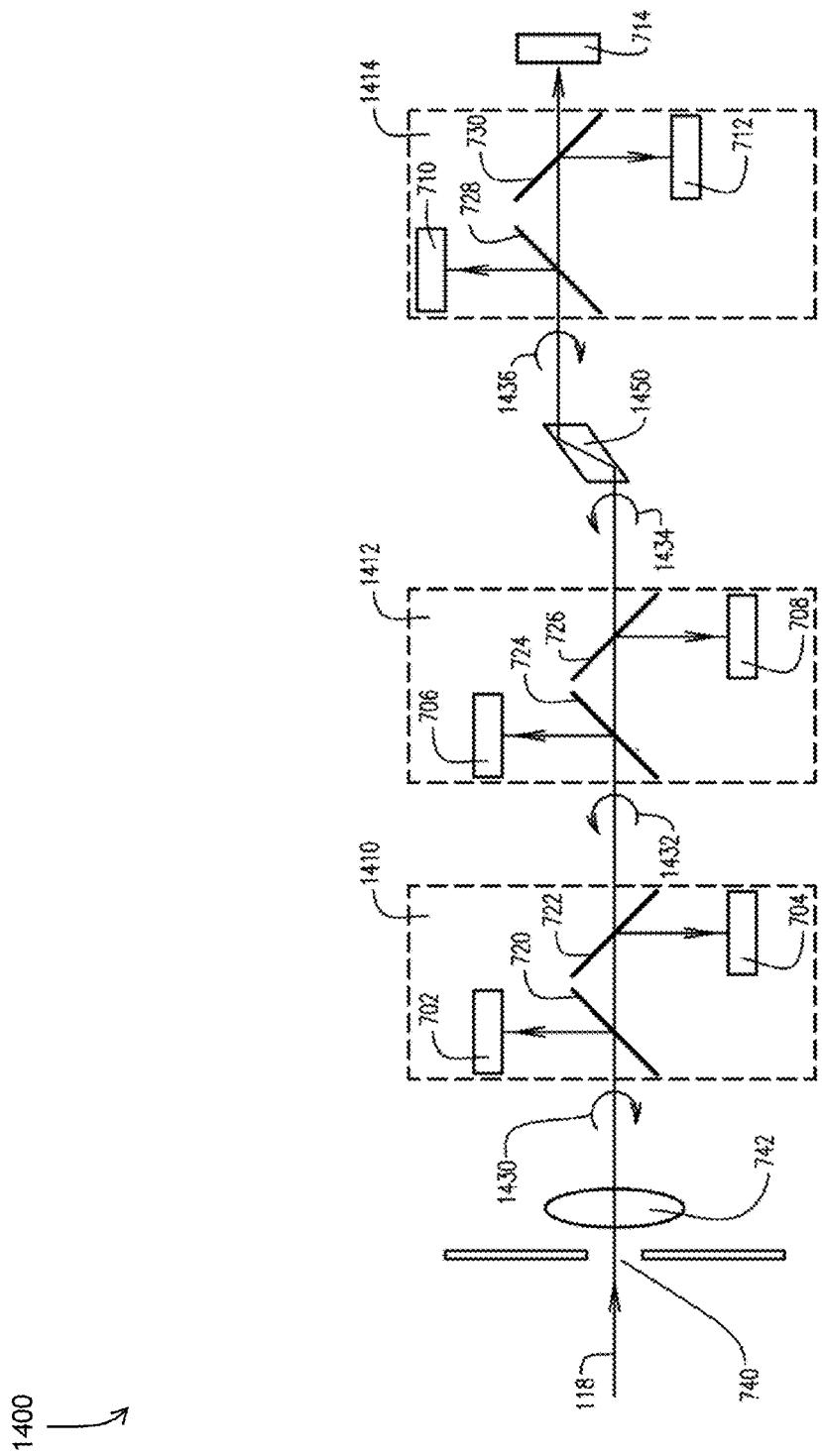
FIG. 14 is a top view showing a paired arrangement of beam splitters and detectors with a Fresnel Rhomb retardation component in accordance with one embodiment of the present invention.

An alternative embodiment of the PSD 150 may employ internal reflections from a prism to induce phase shifts in the beam and thereby provide sensitivity to different polarization components of the incident beam 118. FIG. 14 shows a configuration which incorporates an exemplary Fresnel Rhomb 1450 for this purpose. Fresnel Rhombs are common optical elements, and one useful advantage may be that their retardance vs. wavelength is essentially achromatic over relatively wide spectral ranges. In FIG. 14, the incident beam 118 enters the PSD 150 through an aperture 740, and transmits through an optional focusing lens 742. Again, one design element of this alternative embodiment PSD 150 may be the paired arrangement of beam splitters and detectors. The incident beam 118 may be transmitted through and partially reflected from beam splitters 720 and 722, and into first detector 702 and second detector 704, which together form a first pair 1410. This first pair 1410 may be azimuthally rotated 1430 about the axis of the incident beam 118.

As before, the signals from first detector 702 and second detector 704 are summed into a signal S1. The beam transmitted through the first pair 1410 interacts with a second pair 1412, comprising beam splitters third beam splitter 724 and fourth beam splitter 726, and detectors third detector 706 and fourth detector 708. This second pair 1412 may also be azimuthally rotated 1432 about the axis of the incident beam 118. The signals from third detector 706 and fourth detector 708 are summed into a signal S2. The beam transmits through Fresnel Rhomb 1450, which may also be azimuthally rotated 1434 about the axis of the incident beam 118. Next the beam interacts with a third pair 1414, comprising fifth beam splitter 728 and sixth beam splitter 730, and fifth detector 710 and sixth detector 712. This third pair 1414 may also be azimuthally rotated 1436 about the axis of the incident beam 118. The signals from fifth detector 710 and sixth detector 712 are summed into a signal S3. The remaining beam which may be transmitted through sixth beam splitter 730 may be collected by detector seventh detector 714, which in one embodiment may be a 2-dimensional Position Sensitive Detector with four outputs X1, Y1, X2, Y2. The average value of the output signals from the Position Sensitive Detector, (X1+Y1+X2+Y2)/4, may be stored as a signal S4. Optimal values for the azimuthal orientations of the beam splitter/detector pairs and the Fresnel Rhomb are discussed below.

To acquire raw data in the present invention multiple wavelength ellipsometer system, the light sources are sequentially cycled through a series of states, with each state comprising one of: one of the light sources turned on, and none of the light sources turned on. During each state, the output signals from the detectors, summed signals S1, S2, S3, and S4, are digitized and stored by a processor for further processing. To compensate for ambient background light and electronic signal offsets, the signal intensities acquired with none of the light sources turned on are subtracted from the signal intensities acquired with one of the light sources on. The "background corrected" Raw Data, which may include four signal intensity values at each wavelength, may be subsequently used to calibrate the ellipsometer system, and to acquire ellipsometric data.

Embodiments of the present invention may employ a mathematical description of the Polarization State Detector (PSD 150). The interaction of polarized light with optics may be commonly modeled using Mueller Matrix and Stokes Vector formalism. A Stokes vector X which represents the polarization state of the incident beam 118 to the PSD 150:

$$X = \begin{pmatrix} x_0 \\ x_1 \\ x_2 \\ x_3 \end{pmatrix}$$

The incident beam 118, with polarization state X, interacts with the optical elements (beam splitters and retarders) in the PSD 150, and the resulting beam intensities are measured by the Detectors. The measured detector signals may be packed in a vector M:

$$M = \begin{pmatrix} S1 \\ S2 \\ S3 \\ S4 \end{pmatrix}$$

In the present invention, the detector signals are defined as follows: S1 is the sum of the signals from the first detector pair of first detector 702 and second detector 704, S2 may be the sum of the signals from the second detector pair third detector 706 and fourth detector 708, S3 may be the sum of the signals from the third detector pair fifth detector 710 and sixth detector 712, and S4 may be the signal from seventh detector 714. In the case that seventh detector 714 may be a position sensitive detector which has four outputs signals X1, Y1, X2, and Y2, the S4 signal may be defined as the average of the 4 output signals: S4=(X1+Y1+X2+Y2)/4. As discussed by Azzam in his original paper on division of amplitude polarimeters (DOAP), systems herein may calculate the resulting measured detector signals M for a given input polarization state X if the 4×4 instrument matrix A is known:

$$M = A \cdot X$$

The instrument matrix A may be a 4×4 matrix, and the rows of A specify the sensitivity of each detector element in M to the Stokes vector elements X of the incident beam 118. If A is nonsingular, the inverse of A exists (which may be denoted by $A^{-1}$) and systems herein may determine the Stokes vector elements X of the incident beam 118 from the measured detector intensities M by the following formula:

$$X = A^{-1} \cdot M$$

The 4×4 instrument matrix A may depend on the type and order of the optical elements on the beam path inside the Polarization State Detector (PSD 150). As an example, an idealized DOAP, which splits the incoming beam into 4 beams of exactly equal intensity, each detector exhibits polarization sensitivity consistent with the fundamental definition of a Stokes vector. The first detector may be sensitive only to the intensity of the incident beam 118 (independent of its polarization), and the corresponding first row in the instrument matrix A may be (1,0,0,0). The second detector may be sensitive only to the horizontal/vertical polarization component of the incoming beam, and the corresponding second row of the instrument matrix A may be (1,1,0,0). The third detector may be sensitive only to the +45°/−45° polarization component of the incoming beam, and the corresponding third row of the instrument matrix A may be (1,0,1,0). The fourth detector may be sensitive only to the right-handed/left-handed circularly polarized component of the incoming beam, and the corresponding fourth row of the instrument matrix A may be (1,0,0,1). The resulting 4×4 instrument matrix $A_{ideal}$ for the idealized DOAP is shown below, along with its inverse $A_{ideal}^{-1}$.

$$A_{ideal} = \begin{pmatrix} 1 & 0 & 0 & 0 \\ 1 & 1 & 0 & 0 \\ 1 & 0 & 1 & 0 \\ 1 & 0 & 0 & 1 \end{pmatrix}$$

$$A_{ideal}^{-1} = \begin{pmatrix} 1 & 0 & 0 & 0 \\ -1 & 1 & 0 & 0 \\ -1 & 0 & 1 & 0 \\ -1 & 0 & 0 & 1 \end{pmatrix}$$

Given the inverse of a 4×4 instrument matrix $A^{-1}$, and a vector of measured detector signals M, how does noise in the measured detector signals M affect the noise in the determined Stokes vector elements of the incoming beam $X = A^{-1}M$? The literature ("Single-layer-coated beam splitters for the division-of-amplitude photopolarimeter", R. M. A. Azzam and F. F. Sudradjat, Applied Optics Vol. 44, No. 2, page 190, 2005) typically may use the magnitude of the determinant of A, |det A|, as a metric for characterizing the noise performance of a DOAP with an instrument matrix A. If |det A| is zero, A may be singular, and its inverse does not exist. Therefore, maximizing |det A| ensures that $A^{-1}$ may be "maximally" nonsingular, which minimizes the transfer of noise in the measured detector signals M into the determined Stokes vector elements of the incoming beam X. However, the magnitude of the determinant of A metric does not provide insight about the noise distribution on each of the individual Stokes vector elements. Systems herein may calculate noise on each of the determined Stokes vector elements X using the formulas below. The noises on each of the measured detector signals S1, S2, S3, and S4 are denoted $n_1$, $n_2$, $n_3$, and $n_4$, and the resulting noises on each of the calculated Stokes vector elements X are denoted $xn_0$, $xn_1$, $xn_2$, and $xn_3$.

$$X_{noise} = \begin{pmatrix} x_0 + xn_0 \\ x_1 + xn_1 \\ x_2 + xn_2 \\ x_3 + xn_3 \end{pmatrix}$$

$$= A^{-1} M_{noise}$$

$$= \begin{pmatrix} ai_{00} & ai_{01} & ai_{02} & ai_{03} \\ ai_{10} & ai_{11} & ai_{12} & ai_{13} \\ ai_{20} & ai_{21} & ai_{22} & ai_{23} \\ ai_{30} & ai_{31} & ai_{32} & ai_{33} \end{pmatrix} \begin{pmatrix} S1 + n_1 \\ S2 + n_2 \\ S3 + n_3 \\ S4 + n_4 \end{pmatrix}$$

$x_0 = ai_{00}S1 + ai_{01}S2 + a_{02}S3 + a_{03}S4 \quad xn_0 = ai_{00}n_1 + ai_{01}n_2 + a_{02}n_3 + a_{03}n_4$ $x_1 = ai_{10}S1 + ai_{11}S2 + a_{12}S3 + a_{13}S4 \quad xn_1 = ai_{10}n_1 + ai_{11}n_2 + a_{12}n_3 + a_{13}n_4$ $x_2 = ai_{20}S1 + ai_{21}S2 + a_{22}S3 + a_{23}S4 \quad xn_2 = ai_{20}n_1 + ai_{21}n_2 + a_{22}n_3 + a_{23}n_4$ $x_3 = ai_{30}S1 + ai_{31}S2 + a_{32}S3 + a_{33}S4 \quad xn_3 = ai_{30}n_1 + ai_{31}n_2 + a_{32}n_3 + a_{33}n_4$ Assume that the signal noises $n_1$, $n_2$, $n_3$, and $n_4$ are independent of the measured intensity, uncorrelated with each other, and of equal magnitude denoted ns (these assumptions would be valid if the dominant source of noise in the system is detector and/or electrical dark noise). Systems herein may calculate the total uncorrelated noise factors for the Stokes vector elements, denoted $xN_0$, $xN_1$, $xN_2$, and $xN_3$, by the square root of the sum of the squares of the individual noise terms:

$$ns \cdot xN_0 = \frac{\sqrt{(ai_{00}n_1)^2 + (ai_{01}n_2)^2 + (a_{02}n_3)^2 + (a_{03}n_4)^2}}{\sqrt{ai_{00}^2 + ai_{01}^2 + a_{02}^2 + a_{03}^2}} = ns$$

$$ns \cdot xN_1 = \frac{\sqrt{(ai_{10}n_1)^2 + (ai_{11}n_2)^2 + (a_{12}n_3)^2 + (a_{13}n_4)^2}}{\sqrt{ai_{10}^2 + ai_{11}^2 + a_{12}^2 + a_{13}^2}} = ns$$

$$ns \cdot xN_2 = \frac{\sqrt{(ai_{20}n_1)^2 + (ai_{21}n_2)^2 + (a_{22}n_3)^2 + (a_{23}n_4)^2}}{\sqrt{ai_{20}^2 + ai_{21}^2 + a_{22}^2 + a_{23}^2}} = ns$$

$$ns \cdot xN_3 = \frac{\sqrt{(ai_{30}n_1)^2 + (ai_{31}n_2)^2 + (a_{32}n_3)^2 + (a_{33}n_4)^2}}{\sqrt{ai_{30}^2 + ai_{31}^2 + a_{32}^2 + a_{33}^2}} = ns$$

The total uncorrelated noise on each determined Stokes vector element may be proportional to the square root of the sum of the squares of corresponding rows of the inverse instrument matrix $A^{-1}$. For the idealized DOAP, this results in total uncorrelated Noise Factors of: $xN_0 = 1$ and $xN_1 = xN_2 = xN_3 = \sqrt{2} \approx 1.41$.

Embodiments of the present invention may employ a methodology for calculating the 4×4 instrument matrix A. The Mueller matrices for glass plate beamsplitters in reflection (BSr, with p-reflectivity Rp and s-reflectivity Rs) and transmission (BSt, with p-transmissivity Tp and s-transmissivity Ts), a retarder Ret with retardance δ and a transmission factor RetT, and the standard azimuthal rotation matrix Rot(θ) are shown below. The vector for a detector which may be not polarization sensitive, Det, is also shown. Appropriate combinations of these matrices may be multiplied together to calculate the polarization dependent detector intensities for each beam in the PSD 150. To calculate the Mueller matrix for an optical element with Muller matrix M that may be azimuthally rotated by an angle θ about the beam path, pre- and post-multiply the Mueller matrix of the optical element using the following sequence of matrices: Rot(θ)·M·Rot(−θ).

$$BSr = \begin{pmatrix} \frac{1}{2}(Rp + Rs) & \frac{1}{2}(Rp - Rs) & 0 & 0 \\ \frac{1}{2}(Rp - Rs) & \frac{1}{2}(Rp + Rs) & 0 & 0 \\ 0 & 0 & \sqrt{RpRs} & 0 \\ 0 & 0 & 0 & \sqrt{RpRs} \end{pmatrix}$$

$$BSt = \begin{pmatrix} \frac{1}{2}(Tp+Ts) & \frac{1}{2}(Tp-Ts) & 0 & 0 \\ \frac{1}{2}(Tp-Ts) & \frac{1}{2}(Tp+Ts) & 0 & 0 \\ 0 & 0 & \sqrt{TpTs} & 0 \\ 0 & 0 & 0 & \sqrt{TpTs} \end{pmatrix}$$

$$Ret = RetT \cdot \begin{pmatrix} 1 & 0 & 0 & 0 \\ 0 & 1 & 0 & 0 \\ 0 & 0 & \cos(\delta) & \sin(\delta) \\ 0 & 0 & -\sin(\delta) & \cos(\delta) \end{pmatrix}$$

$$Rot(\theta) = \begin{pmatrix} 1 & 0 & 0 & 0 \\ 0 & \cos(2\theta) & -\sin(2\theta) & 0 \\ 0 & \sin(2\theta) & \cos(2\theta) & 0 \\ 0 & 0 & 0 & 1 \end{pmatrix}$$

$$Det = (1 \; 0 \; 0 \; 0)$$

In one embodiment of the present invention, PSD 150 may use uncoated fused silica plate beam splitters, with the angle of incidence set to 45°. At an operating wavelength of 546 nm, the index of fused silica may be 1.46, and the reflection and transmission coefficients are: Tp≈0.986, Ts≈0.847, Rp≈0.014, and Rs≈0.153 (see FIG. 9). With the mounting scheme illustrated in FIG. 7, the plane of incidence of all beam splitters may be rotated 90° with respect to the sample plane of incidence. From the schematic in FIG. 7, the beam entering the first detector 702 may be simply reflected from first beam splitter 720 (optional waveplate 732 may be not present in this embodiment). The polarization dependent intensity vector of the first detector (PD1) may be given by:

PD1=Det·Rot(90)·BSr·Rot(−90)≈(0.0835 0.0695 0 0)

The beam entering the second detector 704 transmits through first beam splitter 720 and reflects from BS2; the polarization dependent intensity vector PD2 of the second detector may be given by:

PD2=Det·Rot(90)·BSr·Rot(−90)·Rot(90)·BSt·
Rot(−90)≈(0.0717 0.0579 0 0)

In the present invention, the signals from the detector pair first detector 702 and second detector 704 are summed together to provide compensation for misalignments of the incoming beam. Therefore the polarization dependent intensity vectors PD1 and PD2 are also summed into a vector $S1_{PD}$, which may be the first row of the instrument matrix.

$S1_{PD}$≈(0.1552 0.1274 0 0)

After transmitting through BS2, the beam transmits through a quartz waveplate 734. In this embodiment, the retardance of waveplate 734 may be 110°, and the fast axis of waveplate 734 may be azimuthally oriented at −26°. The transmission factor RetT for a quartz waveplate may be ≈0.91, which may be due to Fresnel reflection losses. The beam reflects from third beam splitter 724 into third detector 706, and the polarization dependent intensity PD3 of the third detector may be given by:

PD3=Det·Rot(90)·BSr·Rot(−90)·Rot(−26)·Ret·Rot(+
26)·Rot(90)·BSt·Rot(−90)·Rot(90)·BSt·Rot(−90)≈
(0.0628 −0.0008 −0.0344 0.0391)

The beam entering fourth detector 708 may be similar to the beam entering third detector 706, except that it transmits through third beam splitter 724 and may be reflected by fourth beam splitter 726, resulting in the following polarization dependent intensity vector PD4 of the fourth detector:

PD4=Det·Rot(90)·BSr·Rot(−90)·Rot(90)·BSt·
Rot(−90)·Rot(−26)·Ret·Rot(+26)·Rot(90)·BSt·
Rot(−90)·Rot(90)·BSt·Rot(−90)≈
(0.0540 −0.0009 −0.0286 0.0326)

Summing the PD3 and PD4 vectors yields the polarization dependent intensity vector $S2_{PD}$ for the second detector pair, which may be the second row of the instrument matrix:

$S2_{PD}$≈(0.1168 −0.0017 −0.0630 0.0717)

After transmitting through fourth beam splitter 726, the beam passes through quartz waveplate 736, which in this embodiment also has a retardance of 110°, but with the fast axis azimuthally oriented at +26°. The beam reflects from fifth beam splitter 728 into detector fifth detector 710, and the polarization dependent intensity vector PD5 of the fifth detector may be given by:

PD5=Det·Rot(90)·BSr·Rot(−90)·Rot(26)·Ret·Rot
(−26)·Rot(90)·BSt·Rot(−90)·Rot(90)·BSt·Rot
(−90)·Rot(−26)·Ret·Rot(+26)·Rot(90)·BSt·Rot
(−90)·Rot(90)·BSt·Rot(−90)≈(0.0476 −0.0023
0.0304 0.0248)

The beam entering detector sixth detector 712 may be similar to the beam entering fifth detector 710, except that it transmits through fifth beam splitter 728 and may be reflected by sixth beam splitter 730, resulting in the following polarization dependent intensity vector PD6 of the sixth detector:

PD6=Det·Rot(90)·BSr·Rot(−90)·Rot(90)·BSt·Rot
(−90)·Rot(26)·Ret·Rot(−26)·Rot(90)·BSt·Rot
(−90)·Rot(90)·BSt·Rot(−90)·Rot(−26)·Ret·Rot(+
26)·Rot(90)·BSt·Rot(−90)·Rot(90)·BSt·Rot(−90)≈
(0.0409 −0.0022 0.0255 0.0206)

Summing the PD5 and PD6 vectors yields the polarization dependent intensity vector $S3_{PD}$ for the third detector pair, which may be the third row of the instrument matrix:

$S3_{PD}$≈(0.0885 −0.0045 0.0559 0.0454)

The remaining beam transmits through sixth beam splitter 730 and may be collected by seventh detector 714. The resulting polarization dependent intensity vector PD7, which includes the effects of the beam transmitting through all 6 beam splitters and 2 waveplates, may be given by the following equation (the factor of ¼ assumes a position sensitive detector may be used for seventh detector 714, in which case the light intensity may be split between the 4 outputs):

PD7=¼Det·Rot(90)·BSt·Rot(−90)·Rot(90)·BSt·Rot
(−90)·Rot(26)·Ret·Rot(−26)·Rot(90)·BSt·Rot
(−90)·Rot(90)·BSt·Rot(−90)·Rot(−26)·Ret·Rot
(+26)·Rot(90)·BSt·Rot(−90)·Rot(90)·BSt·Rot
(−90)≈(0.1262 −0.0249 0.0004 −0.0277)

The polarization dependent intensity vector PD7 may be the fourth row of the instrument matrix. The resulting instrument matrix, normalized such that the first element may be 1 (that is, dividing each element of the matrix by 0.1552), for one embodiment $A_{PE1}$ and its inverse $A_{PE1}^{-1}$ are shown below.

$$A_{PE1} = \begin{pmatrix} 1.0000 & 0.8209 & 0 & 0 \\ 0.7526 & -0.0110 & -0.4059 & 0.4620 \\ 0.5702 & -0.0290 & 0.3602 & 0.2925 \\ 0.8131 & -0.1604 & 0.0026 & -0.1784 \end{pmatrix}$$

$$A_{PE1}^{-1} = \begin{pmatrix} 0.1553 & 0.1709 & 0.1872 & 0.7494 \\ 1.0290 & -0.2082 & -0.2280 & -0.9129 \\ 0.0132 & -1.0592 & 1.5837 & -0.1464 \\ -0.2170 & 0.9506 & 1.0811 & -1.3711 \end{pmatrix}$$

The noise factors for one embodiment of the PSD 150, calculated as previously described by computing the square root of the sum of the squares of corresponding rows of the inverse instrument matrix $A_{PE1}^{-1}$, are: $xN_0=0.81$, $xN_1=1.41$, $xN_2=1.91$, and $xN_3=2.00$. Compared to the Idealized DOAP noise factors, $xN_0$ may be about 20% lower (0.81 vs. 1.00), $xN_1$ may be essentially the same (approximately 1.41), $xN_2$ may be about 35% higher (1.91 vs. 1.41), and $xN_3$ may be about 42% higher (2.00 vs. 1.41). While the noise performance of one embodiment PSD 150 for determining the $x_2$ and $x_3$ Stokes vectors may be degraded compared to the idealized DOAP, acceptable performance may be still obtained, especially considering that only uncoated fused silica plates are used for beam splitters.

Figure 15:
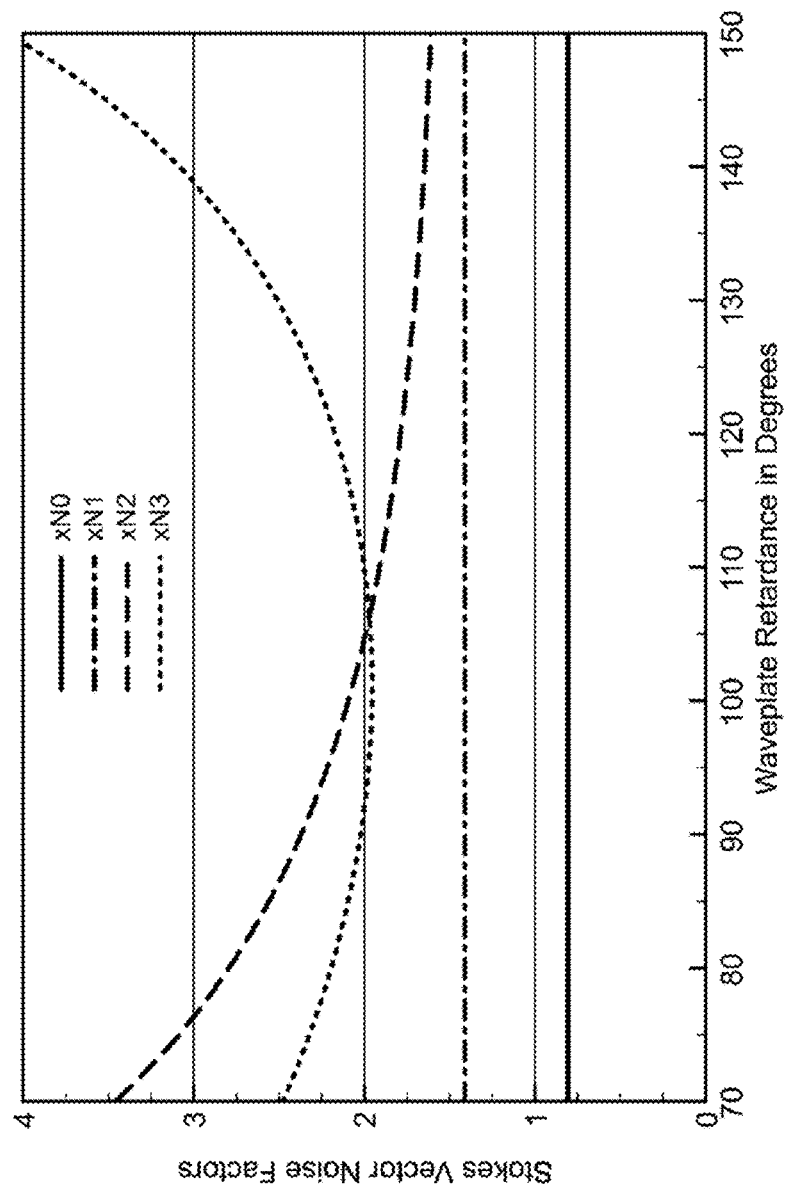
FIG. 15 is a graph of calculated Stokes vector noise factors of PSD vs. waveplate retardance associated with one embodiment of the present invention.

One embodiment of the PSD 150 may employ quartz waveplates, which are strongly chromatic optical devices, that is, their retardance varies inversely with wavelength. The Stokes Vector Noise Factors were calculated vs. waveplate retardance, and are plotted in FIG. 15. FIG. 15 shows that the Noise Factors for the $x_0$ and $x_1$ Stokes vectors are constant vs. waveplate retardance, while the Noise Factors for the $x_2$ and $x_3$ Stokes vectors vary strongly with waveplate retardance. However, if the waveplate retardance may be kept in a limited range, for example, between 90 and 120°, acceptable noise performance may be maintained. Choosing a waveplate with an exemplary ¼ wave retardance at 633 nm may provide acceptable performance with one embodiment PSG 110 which may use LED light sources at 465 nm, 520 nm, 580 nm, and 635 nm, as the corresponding retardance values at the light source wavelengths may be: 122.5°, 109.6°, 98.2°, and 89.7°.

To provide improved chromatic performance in the present invention, system 200 may employ an additional embodiment PSD 150 using an achromatic Fresnel Rhomb for the retarder element. The configuration of an additional embodiment PSD 150 is shown in FIG. 14. The derivation of the instrument matrix A for the additional embodiment proceeds in a similar manner to the derivation of the first embodiment. In the additional embodiment, the first pair of beam splitters, 720 and 722, are azimuthally rotated by +70°. The polarization dependent intensity vector of the first detector (PD1), the second detector (PD2), and the sum of the first pair of detectors (S1$_{PD}$) are shown below.

PD1=Det·Rot(70)·BSr·Rot(−70)≈
  (0.0835 0.0532 −0.0447 0)

PD2=Det·Rot(70)·BSr·Rot(−70)·Rot(70)·BSt·
  Rot(−70)≈(0.0717 0.0443 −0.0372 0)

S1$_{PD}$≈(0.1552 0.0976 −0.0819 0)

The beam may be reflected off the second pair of beam splitters, third beam splitter 724 and fourth beam splitter 726, which are azimuthally rotated by −70°. The polarization dependent intensity vector of the third detector (PD3), the fourth detector (PD4), and the sum of the second pair of detectors (S2$_{PD}$) are shown below.

PD3=Det·Rot(−70)·BSr·Rot(70)·Rot(70)·BSt·Rot
  (−70)·Rot(70)·BSt·Rot(−70)≈(0.0690 0.0364
  0.0441 0)

PD4=Det·Rot(−70)·BSr·Rot(70)·Rot(−70)·BSt·
  Rot(70)·Rot(70)·BSt·Rot(−70)·Rot(70)·BSt·
  Rot(−70)≈(0.0593 0.0301 0.0369 0)

S2$_{PD}$≈(0.1283 0.0665 0.0810 0)

Next, the beam passes through a Fresnel Rhomb retarder 1450, which has a nominal retardance of 90°, and may be azimuthally rotated by −70°. If the Fresnel Rhomb may be constructed from fused silica, the transmission factor RetT for the retarder may be ≈0.93. The beam may be reflected off the third pair of beam splitters, fifth beam splitter 728 and sixth beam splitter 730, which are azimuthally rotated by +70°. The polarization dependent intensity vector of the fifth detector (PD5), the sixth detector (PD6), and the sum of the third pair of detectors (S3$_{PD}$) are shown below.

PD5=Det·Rot(70)·BSr·Rot(−70)·Rot(−70)·Ret·
  Rot(70)·Rot(−70)·BSt·Rot(70)·Rot(−70)·BSt·Rot
  (70)·Rot(70)·BSt·Rot(−70)·Rot(70)·BSt·Rot(−70)≈
  (0.0542 −0.0065 0.0050 0.0444)

PD6=Det·Rot(70)·BSr·Rot(−70)·Rot(70)·BSt·
  Rot(−70)·Rot(−70)·Ret·Rot(70)·Rot(70)·BSt·Rot
  (70)·Rot(−70)·BSt·Rot(70)·Rot(70)·BSt·
  Rot(−70)·Rot(70)·BSt·Rot(−70)≈(0.0466 −0.0058
  0.0042 0.0370)

S3$_{PD}$≈(0.1008 −0.0123 0.0092 0.0814)

The remaining beam transmits through sixth beam splitter 730 and may be collected by seventh detector 714. The resulting polarization dependent intensity vector PD7, which includes the effects of the beam transmitting through all 6 beam splitters and the Fresnel Rhomb, may be given by the following equation (the factor of ¼ assumes a position sensitive detector may be used for seventh detector 714, in which case the light intensity may be split between the 4 outputs):

PD7=¼Det·Rot(70)·BSt·Rot(−70)·Rot(70)·BSt·
  Rot(−70)·Rot(−70)·Ret·Rot(70)·Rot(−70)·BSt·Rot
  (70)·Rot(−70)·BSt·Rot(70)·Rot(70)·BSt·
  Rot(−70)·Rot(70)·BSt·Rot(−70)≈
  (0.1414 −0.0351 −0.0021 −0.0203)

The polarization dependent intensity vector PD7 may be the fourth row of the instrument matrix. The resulting instrument matrix, normalized such that the first element may be 1 (that is, dividing each element of the matrix by 0.1552), for the additional embodiment $A_{PE2}$ and its inverse $A_{PE2}^{-1}$ are shown below.

$$A_{PE2} = \begin{pmatrix} 1.0000 & 0.6288 & -0.5276 & 0 \\ 0.8266 & 0.4286 & 0.5216 & 0 \\ 0.6496 & -0.0792 & 0.0595 & 0.5243 \\ 0.9110 & -0.2261 & -0.0135 & -0.1311 \end{pmatrix}$$

$$A_{PE2}^{-1} = \begin{pmatrix} 0.1552 & 0.1552 & 0.1669 & 0.6675 \\ 0.6731 & 0.6839 & -0.2284 & -1.1537 \\ -0.7990 & 1.1092 & -0.0275 & -0.1098 \\ 0 & -0.2148 & 1.6600 & -0.9888 \end{pmatrix}$$

The noise factors for the additional embodiment of the PSD 150, calculated as previously described by computing the square root of the sum of the squares of corresponding rows of the inverse instrument matrix $A_{PE2}^{-1}$, are: $xN_0=0.72$, $xN_1=1.53$, $xN_2=1.37$, and $xN_3=1.94$. Compared to one embodiment noise factors, $xN_0$ may be about 11% lower (0.72 vs. 0.81), $xN_1$ may be about 9% higher (1.53 vs. 1.41), $xN_2$ may be about 28% lower (1.37 vs. 1.91), and $xN_3$ may be about 3% lower (1.94 vs. 2.00). The overall noise factor performance may be slightly better for the additional embodiment compared to one embodiment. But, the additional embodiment has the significant advantage of using an achromatic Fresnel Rhomb retarder element, which enables the additional embodiment to be operated over a very wide spectral range without degradation in noise performance. It may be emphasized that uncoated fused silica glass plate beam splitters employed in PSD 150 embodiments are also achromatic elements, and may be operated over a very wide spectral range.

The use of uncoated glass plates for beam splitters does result in a less than optimal intensity balance between the four summed detector signals S1, S2, S3, and S4. The detector intensity balance may be observed by comparing the elements in the first column of the Instrument Matrix. System 200 may overcome the challenge of optimizing intensity balance through specially designed custom coatings for the beam splitters. In the present invention, the intensity balance may be affected by simply changing the gain in the electrical readout circuit for specifically chosen detector pairs.

Figure 16:
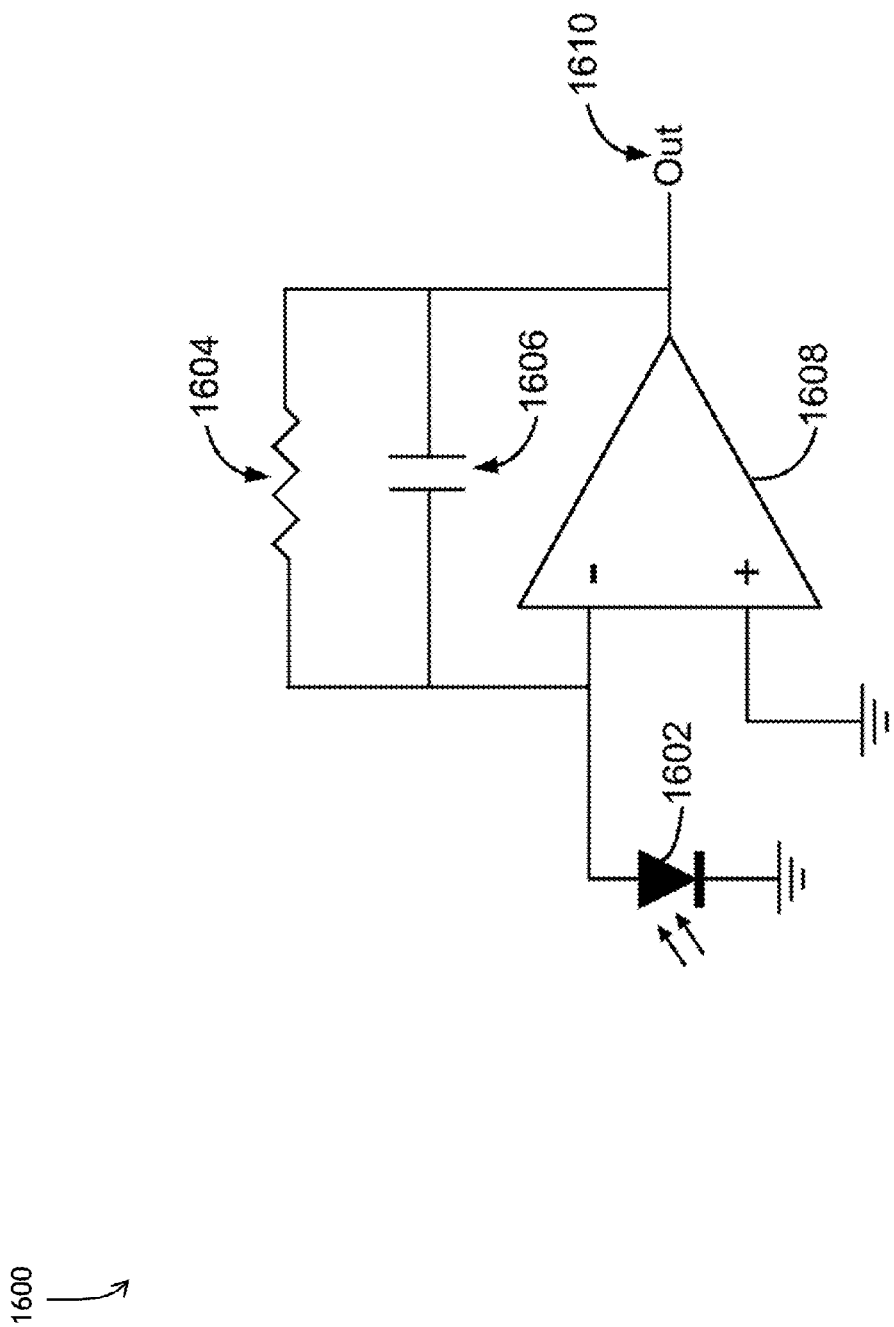
FIG. 16 is an electronic readout circuit for photodiode detectors associated with one embodiment of the present invention.

In embodiments PSD 150, each detector may be operationally coupled to a photodiode detector readout circuit, using the unbiased trans-impedance configuration as shown in FIG. 16. Light may be collected by photodiode detector 1602, generates a current, and the current may be converted to an output voltage 1610 by feedback resistor 1604 and operational amplifier 1608. The non-inverting terminal '+' of operational amplifier 1608 may be connected to Ground, and the inverting terminal '−' of operational amplifier 1608 may be connected to the anode of photodiode detector 1602. The output voltage 1610 may be directly proportional to the value of feedback resistor 1604, which may be connected between the inverting terminal '−' of the operational amplifier operational amplifier 1608 and the output 1610. The capacitor 1606 may be typically added in parallel with resistor 1604 to reject high frequency noise, improve stability, and reduce gain peaking.

In theory, it may be possible to choose specific values of resistor 1604 for the detector readout circuit of each detector in the PSD 150, such that all the first column elements in the instrument matrix are one. In practice this may be difficult, as resistors are only available in discrete values. However, resistors are readily available in larger discrete increments. For example, it may be possible to find resistor values which are a factor of two different in resistance. It may be also possible to double the effective resistance by simply connecting two identical resistors in series. Since the values of S2 and S3 are less than S1 and S4, an inventive component that may be employed by PSD 150 embodiments herein may include doubling the feedback resistor 1604 in the readout circuit for detectors third detector 706, fourth detector 708, fifth detector 710, and sixth detector 712. This may effectively increase by a factor of 2 the signals S2 and S3, as S2=D3+D4 and S3=D5+D6. The resulting instrument matrices for the exemplary embodiments with gain doubling, $A_{PE1gd}$ and $A_{PE2gd}$, and their inverse matrices, $A_{PE1gd}^{-1}$ and $A_{PE2gd}^{-1}$, are shown below.

$$A_{PE1gd} = \begin{pmatrix} 1.0000 & 0.8209 & 0 & 0 \\ 2\cdot 0.7526 & 2\cdot -0.0110 & 2\cdot -0.4059 & 2\cdot 0.4620 \\ 2\cdot 0.5702 & 2\cdot -0.0290 & 2\cdot 0.3602 & 2\cdot 0.2925 \\ 0.8131 & -0.1604 & 0.0026 & -0.1784 \end{pmatrix}$$

$$A_{PE1gd}^{-1} = \begin{pmatrix} 0.1552 & 0.0853 & 0.0937 & 0.7497 \\ 1.0292 & -0.1039 & -0.1142 & -0.9133 \\ 0.0136 & -0.5296 & 0.7917 & -0.1459 \\ -0.2171 & 0.4753 & 0.5407 & -1.3714 \end{pmatrix}$$

$$A_{PE2gd} = \begin{pmatrix} 1.0000 & 0.6288 & -0.5276 & 0 \\ 2\cdot 0.8266 & 2\cdot 0.4286 & 2\cdot 0.5216 & 0 \\ 2\cdot 0.6496 & 2\cdot -0.0792 & 2\cdot 0.0595 & 2\cdot 0.5243 \\ 0.9110 & -0.2261 & -0.0135 & -0.1311 \end{pmatrix}$$

$$A_{PE2gd}^{-1} = \begin{pmatrix} 0.1552 & 0.0776 & 0.0834 & 0.6675 \\ 0.6731 & 0.3419 & -0.1442 & -1.1537 \\ -0.7990 & 0.5546 & -0.0137 & -0.1098 \\ 0 & -.1074 & 0.8300 & -0.9888 \end{pmatrix}$$

The noise factors for one embodiment of the PSD 150 with gain doubling, calculated as previously described by computing the square root of the sum of the squares of corresponding rows of the inverse instrument matrix $A_{PE1gd}^{-1}$, are: $xN_0 = 0.78$, $xN_1 = 1.38$, $xN_2 = 0.96$, and $xN_3 = 1.56$. The noise factors for the additional embodiment of the PSD 150, with gain doubling of signals S2 and S3, calculated as previously described by computing the square root of the sum of the squares of corresponding rows of the inverse instrument matrix $A_{PE2gd}^{-1}$, are: $xN_0 = 0.69$, $xN_1 = 1.39$, $xN_2 = 0.98$, and $xN_3 = 1.30$. Each embodiment PSD 150's may show a significant improvement in their noise factors when implementing gain doubling of detectors third detector 706, fourth detector 708, fifth detector 710, and sixth detector 712 in the detector readout circuits. However, if the dominant source of noise in the system is detector dark noise, gain doubling may not improve the noise performance of the PSD 150, as the gain doubling may also double the detector dark noise. If other noise sources are dominant, such as analog-to-digital converter (ADC) noise, and noise in the operational amplifier, the gain doubling approach may be more effective.

Accurate operation of a division of amplitudes polarimeter (DOAP) requires an accurate calibration of the instrument matrix A. Calibration of the instrument matrix A may be typically done with a PSG 110 which includes a rotatable polarizer 438 and a quarter-wave retarder ("Accurate calibration of the four-detector photopolarimeter with imperfect polarizing optical elements", R. M. A. Azzam and Ali G. Lopez, J. Opt. Soc. Am. A Vol. 6, No. 10, page 1513, 1989). The present invention utilizes a similar approach, but it has been modified and extended to accommodate non-idealities which may exist in the present invention hardware. The PSG 110 hardware for the present invention was described previously, and includes a rotatable polarizer 436 mechanism. First the Mueller matrix of a non-ideal polarizer PolNI, which exhibits incomplete extinction of light.

$$PolNI = \begin{pmatrix} \frac{1}{2}(Tp + Ts) & \frac{1}{2}(Tp - Ts) & 0 & 0 \\ \frac{1}{2}(Tp - Ts) & \frac{1}{2}(Tp + Ts) & 0 & 0 \\ 0 & 0 & \sqrt{TpTs} & 0 \\ 0 & 0 & 0 & \sqrt{TpTs} \end{pmatrix}$$

For the non-ideal polarizer PolNI, the transmission factor for p-polarized light may be Tp, and the transmission factor for s-polarized light may be Ts. Note that this form of a Mueller matrix for the non-ideal polarizer may be identical to the Mueller matrix used for a beam splitter in transmission mode. For an ideal polarizer which may completely extinguish linearly polarized light, Ts may be equal to zero. For the non-ideal polarizer model utilized in the present invention, assume that Tp=1 and Ts=q², where q is a small but non-zero value. The non-ideal polarizer matrix PolNI for the present invention may be approximated as:

$$PolNI = \begin{pmatrix} \frac{1}{2}(1+q^2) & \frac{1}{2}(1-q^2) & 0 & 0 \\ \frac{1}{2}(1-q^2) & \frac{1}{2}(1+q^2) & 0 & 0 \\ 0 & 0 & q & 0 \\ 0 & 0 & 0 & q \end{pmatrix}$$

$$\approx \begin{pmatrix} \frac{1}{2} & \frac{1}{2} & 0 & 0 \\ \frac{1}{2} & \frac{1}{2} & 0 & 0 \\ 0 & 0 & q & 0 \\ 0 & 0 & 0 & q \end{pmatrix}$$

The Mueller-Stokes model for the present invention PSG 110, which includes the non-ideal polarizer PolNI, rotation matrices to describe azimuthal rotation θ of the polarizer, and a general Stokes vector with elements $s_0$, $s_1$, $s_2$, and $s_3$ to represent the light from the LED sources LS, is shown below.

$$PSG_{SV}(\theta, s_0, s_1, s_2, s_3, q) =$$

$$Rot(\theta) \cdot PolNI \cdot Rot(-\theta) \cdot LS = Rot(\theta) \cdot \begin{pmatrix} \frac{1}{2} & \frac{1}{2} & 0 & 0 \\ \frac{1}{2} & \frac{1}{2} & 0 & 0 \\ 0 & 0 & q & 0 \\ 0 & 0 & 0 & q \end{pmatrix} \cdot Rot(-\theta) \cdot \begin{pmatrix} s_0 \\ s_1 \\ s_2 \\ s_3 \end{pmatrix} =$$

$$\frac{1}{2} \begin{pmatrix} s_0 + s_1 \cos(2\theta) + s_2 \sin(2\theta) \\ s_0 \cos(2\theta) + s_1 (\cos(2\theta)^2 + 2q \sin(2\theta)^2) + s_2 \cos(2\theta) \sin(2\theta)(1 - 2q) \\ s_0 \sin(2\theta) + s_1 \cos(2\theta) \sin(2\theta)(1 - 2q) + s_2 (\sin(2\theta)^2 + 2q \cos(2\theta)^2) \\ s_3 q \end{pmatrix}$$

The preceding equation, $PSG_{SV}(\theta, s_0, s_1, s_2, s_3, q)$, may be used to calculate the Stokes vector exiting the present invention PSG 110 as a function of the azimuthal rotation angle of the polarizer θ, the Stokes vector elements of the light from the LED sources which enters the polarizer, $s_0$, $s_1$, $s_2$, and $s_3$, and the polarizer non-ideality factor q.

For the instrument matrix calibration procedure, the present invention may be configured in the straight-through mode, which was previously described and is shown in FIG. 1. A waveplate and waveplate rotator WP may be added to the beam path for part of the instrument matrix calibration procedure (though any retardation inducing element may be used in place of the waveplate). When the waveplate may be present in the beam path, the following Mueller matrix sequence $WP_{MM}(\theta_{WP}, \delta_{WP}, RetT, rp_{WP})$ may be multiplied times the $PSG_{SV}(\theta, s_0, s_1, s_2, s_3, q)$ Stokes vector to calculate the Stokes vector of the beam which exits the waveplate and enters the PSD 150.

$$WP_{MM}(\theta_{WP}, \delta_{WP}, RetT, rp_{WP}) =$$

$$Rot(rp_{WP}) \cdot RetT \cdot Rot(\theta_{WP}) \cdot Ret \cdot Rot(-\theta_{WP}) =$$

$$Rot(rp_{WP}) \cdot RetT \cdot Rot(\theta_{WP}) \cdot \begin{pmatrix} 1 & 0 & 0 & 0 \\ 0 & 1 & 0 & 0 \\ 0 & 0 & \cos(\delta_{WP}) & \sin(\delta_{WP}) \\ 0 & 0 & -\sin(\delta_{WP}) & \cos(\delta_{WP}) \end{pmatrix} \cdot Rot(-\delta_{WP})$$

The $WP_{MM}(\theta_{WP}, \delta_{WP}, RetT, rp_{WP})$ Mueller matrix function models the polarization properties of a waveplate which may be azimuthally oriented at $\theta_{WP}$, with a retardance value of $\delta_{WP}$, a transmission factor of RetT, and a rotary power of $rp_{WP}$. Given the Stokes vector output from the PSG 110, the Mueller matrix function for the waveplate, and the 4×4 instrument matrix A (with elements $a_{00}$, $a_{01}$, $a_{02}$, $a_{03}$, $a_{10}$, $a_{11}$, $a_{12}$, $a_{13}$, $a_{20}$, $a_{21}$, $a_{22}$, $a_{23}$, $a_{30}$, $a_{31}$, $a_{32}$, and $a_{33}$) which characterizes the polarization properties the PSD 150, systems herein may calculate signal values SC1, SC2, SC3, and SC4 via the formula below.

$$\begin{pmatrix} SC1 \\ SC2 \\ SC3 \\ SC4 \end{pmatrix} = \begin{matrix} A \cdot WP_{MM}(\theta_{WP}, \delta_{WP}, RetT, rp_{WP}) \cdot \\ PSG_{SV}(\theta, s_0, s_1, s_2, s_3, q) \end{matrix}$$

$$= \begin{pmatrix} a_{00} & a_{01} & a_{02} & a_{03} \\ a_{10} & a_{11} & a_{12} & a_{13} \\ a_{20} & a_{21} & a_{22} & a_{23} \\ a_{30} & a_{31} & a_{32} & a_{33} \end{pmatrix} \cdot WP_{MM}(\theta_{WP}, \delta_{WP}, RetT, rp_{WP}) \cdot$$

$$PSG_{SV}(\theta, s_0, s_1, s_2, s_3, q)$$

Thus completes the "forward calculation" of the signal values SC1, SC2, SC3, and SC4, which may be performed at any specified values of θ, $s_0$, $s_1$, $s_2$, $s_3$, q, $\theta_{WP}$, $\delta_{WP}$, RetT, $rp_{WP}$ and instrument matrix A elements $a_{00}$, $a_{01}$, $a_{02}$, $a_{03}$, $a_{10}$, $a_{11}$, $a_{12}$, $a_{13}$, $a_{20}$, $a_{21}$, $a_{22}$, $a_{23}$, $a_{30}$, $a_{31}$, $a_{32}$, and $a_{33}$.

To calibrate the 4×4 instrument matrix A of the present invention, the system may be first placed in a straight through mode, which was previously described and is shown in FIG. 1. The waveplate and waveplate rotator may be inserted into the beam path between the PSG 110 and PSD 150. The calibration waveplate may be azimuthally rotated to multiple orientations. At each calibration waveplate orientation, the polarizer optic in the PSG 110 may be azimuthally rotated to multiple orientations. At each combination of polarizer and waveplate azimuths, system 200 may acquire and store raw data at each wavelength, as previously described.

The calibration waveplate may be removed from the beam path. System 200 may azimuthally rotate the polarizer optic again to multiple orientations, and acquire and store the raw data (comprising signals S1, S2, S3, and S4, as previously defined) at each azimuthal orientation. In one embodiment, 4 azimuthal angles are used for the calibration waveplate (−67.5°, −22.5°, 22.5°, and 67.5°), and 4 azimuthal angles are used for the polarizer optic (−90°, −45°, 0°, and 45°). This results in a Calibration Data Set with (4+1)·4=20 raw data points acquired at each wavelength, and each raw data point contains 4 signals, for a total of 4·20=80 data values at each wavelength. The Calibration Data Sets are denoted $S1_i$, $S2_i$, $S3_i$, and $S4_i$, where i ranges from 1 to 20, and separate Calibration Data Sets are acquired and stored at each wavelength of the PSG 110.

To determine the calibration values of interest (most importantly, the 16 elements of the 4×4 instrument matrix A) given the acquired Calibration Data Set, the present invention utilizes model-based, least squares, non-linear regression analysis of the data set. This may be the same conceptual approach that is typically used to analyze ellipsometric data, and it has also been applied to the calibration of rotating element ellipsometer systems further described in "Regression calibration method for rotating element ellipsometers", B. Johs, Thin Solid Films Vol. 234, page 395, (1993), and U.S. Pat. No. 5,872,630 to Johs, et al., both of which are incorporated by reference herein in their entirety. This analysis approach may acquire a data set, construct a parameterized model which may calculate data corresponding to the acquired data, define a least squares metric to quantify the difference between the acquired data and the model calculated data, and a regression algorithm may be employed to iteratively adjust (or "fit") the model parameters to minimize the least squares metric. For the present invention, the least squares metric $x^2$ may be written as:

$$\chi^2 = \sum_{i=1}^{20} [(S1_i - SC1_i)^2 + (S2_i - SC2_i)^2 + (S3_i - SC3_i)^2 + (S4_i - SC4_i)^2]$$

The acquisition of Calibration Data set $S1_i$, $S2_i$, $S3_i$, and $S4_i$ was previously described, as was the model used to calculate data $SC1_i$, $SC2_i$, $SC3_i$, and $SC4_i$ (with the subscript i indexing the values of $\theta$ and $\theta_{WP}$ used in the calculation which correspond to the azimuthal orientations of the PSG 110 Polarizer and Calibration Waveplate for the i'th data point). A well-known non-linear regression algorithm for minimizing the least squares metric $x^2$ may be the Levenberg-Marquardt algorithm. Public domain code implementations of the Levenberg-Marquardt algorithm are also available, for example: http://apps.jcns.fz-juelich.de/doku/sc/lmfit. In the present invention, the Levenberg-Marquardt algorithm may be used to simultaneously determine (or "fit") the model parameters by a non-linear regression fit of the 80 point Calibration Data Set.

The determinable model parameters are: $\theta 1$, $\theta 2$, $\theta 3$, and $\theta 4$ (azimuthal angles of the four orientations of the polarizer mechanism in the PSG 110), $s_0$, $s_1$, $s_2$, and $s_3$ (Stokes vector intensities for the light entering the polarizer in the PSG 110), q (the non-ideality factor of the polarizer in the PSG 110), $\theta 1_{WP}$, $\theta 2_{WP}$, $\theta 3_{WP}$, and $\theta 4_{WP}$ (the azimuthal angles of the calibration waveplate in the waveplate rotator), $\delta_{WP}$ (the retardance of the calibration waveplate), RetT (the transmission factor of the calibration waveplate), $rp_{WP}$ (the rotary power of the calibration waveplate) and 4×4 instrument matrix A elements $a_{00}$, $a_{01}$, $a_{02}$, $a_{03}$, $a_{10}$, $a_{11}$, $a_{12}$, $a_{13}$, $a_{20}$, $a_{21}$, $a_{22}$, $a_{23}$, $a_{30}$, $a_{31}$, $a_{32}$, and $a_{33}$.

The number of fit parameters may be reduced by fixing $s_0=1$ (and normalizing the acquired Calibration Data Set and the corresponding Calculated Data Sets by their average values), fixing $a_{00}=1$ (to normalize the instrument matrix A), and fixing $\theta 4_{WP}=45$ (to specify a reference for the coordinate system), resulting in 29 adjustable model fit parameters at each wavelength. The large 80 point Calibration Data Set, which includes many combinations of PSG 110 Polarizer and calibration waveplate azimuthal angles, which in turn generates a range of polarization states in the beam which enters the PSD 150, overdetermines the 29 parameter calculation model, which enables the simultaneous determination of the 16 instrument matrix A elements, along with all the characterizing parameters for the PSG 110 and calibration waveplate.

Since the azimuthal angles are determined in the regression fit, the polarizer and waveplate azimuthal rotation mechanisms do not have to be accurate, though they do still need to be reproducible. Fitting for the polarizer non-ideality factor q enables the use of low cost plastic polarizers. Likewise, the retardance, rotary power, and transmission factor of the calibration waveplate do not need to be accurately known, as they are determined as part of the instrument matrix calibration procedure. In the present invention, the regression fit may be performed using Calibration Data Sets acquired at each wavelength, and all the resulting parameters from the calibration at each wavelength are stored for use in subsequent calibrations and ellipsometric data acquisition.

Ideally, the 4×4 instrument matrix A determined in the preceding calibration procedure may be constant under any condition. In reality, there a number of factors which may affect the instrument matrix A elements. One example may be a shift in the wavelength of the light source. While one embodiment glass plate beamsplitters are essentially achromatic, the waveplates utilized in one embodiment PSD 150 are chromatic.

Figure 17:
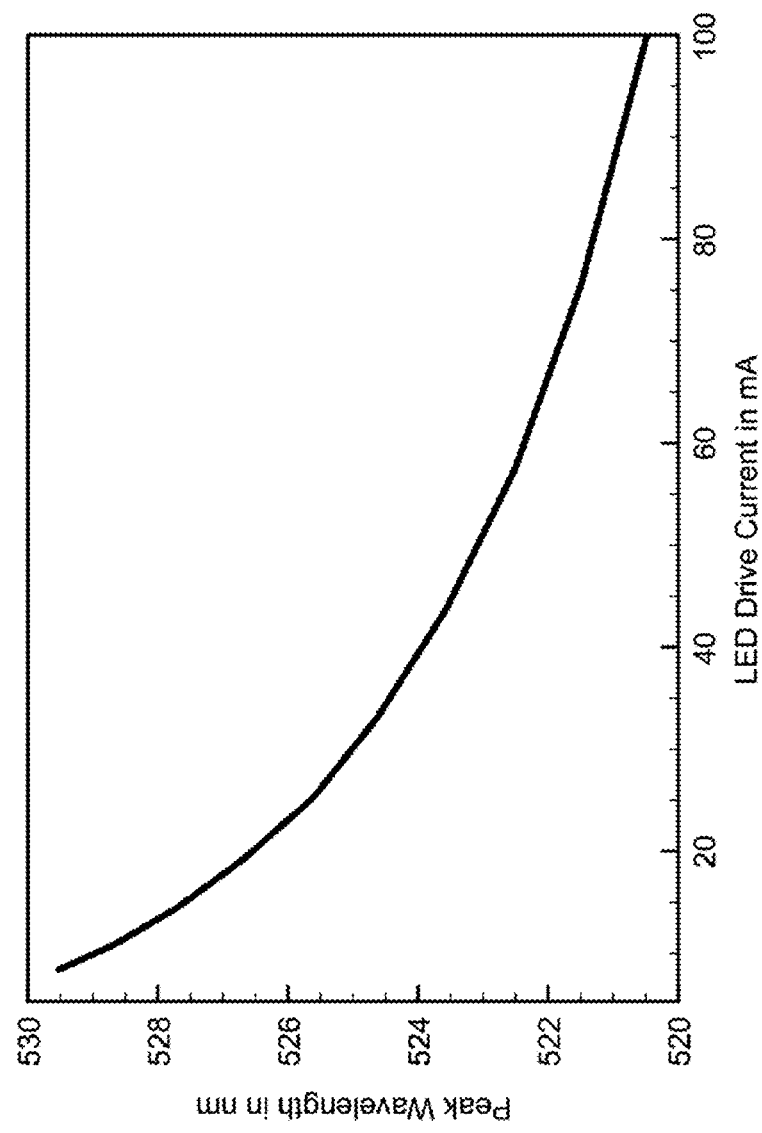
FIG. 17 is a graph of shift in peak wavelength vs. drive current for an exemplary green LED source associated with one embodiment of the present invention.

The wavelength of LED light sources is known to shift vs. drive current, as shown in FIG. 17. The data in FIG. 17 was acquired with a typical green LED, and the peak wavelength may be observed to shift almost 10 nm over a 90 mA range in drive current. One strategy to minimize affects due to current induced wavelength shifts may be to operate the LED's in the system with the same drive currents. However, there may be dynamic range benefits to adjusting the LED current during operation of the instrument. Temperature changes may also induce shifts in the LED peak wavelength. While the temperature induced wavelength shifts are much smaller (<0.1 nm/° C.), they may still be significant. Another factor which may affect the instrument matrix A elements may be misalignment of the incident beam 118 with respect to the PSD 150. While one element of the present invention may be the paired arrangement of beam splitters and detectors to cancel errors due to the misalignment of the incident beam 118 to the PSD 150, the error cancelation provided by the paired arrangement may be only to the first order. Furthermore, any mis-matches in the responsivity of the paired detectors, and in the electronic gain of the read out circuits of the paired detectors, may also degrade the error cancelation. One embodiment arrangement of beam splitters does not cancel beam misalignment errors in the plane orthogonal to the plane of incidence of the beam splitters, nor does it cancel errors due to misalignment induced changes in waveplate retardance.

Embodiments of the present invention may employ a method of compensating for the above mentioned potential errors in the instrument matrix A. The first step may be to determine the instrument matrix A over a range of possible operating conditions. For example, this range of operating conditions might involve a sequence of LED drive currents, various temperatures, and/or a range of beam misalignment angles. At each operating condition, system 200 may acquire and store the instrument matrix A, using the previously described instrument matrix calibration procedure. The second step may be to fit a polynomial function vs. the operating conditions to each element in the instrument matrices. This fit may be performed individually for each element in the instrument matrix, and the number of data points in the fit may be equal to the number of instrument matrices acquired over the range of operating conditions. The model for the fit may be a polynomial function of the form shown below.

$$mm_{i,j} = m0_{i,j} + mC1_{i,j} \cdot C + mT1_{i,j} \cdot T + mX1_{i,j} \cdot X + mX2_{i,j} \cdot X^2 + mY1_{i,j} \cdot Y + mY2_{i,j} \cdot Y^2 + mXY1_{i,j} \cdot X \cdot Y$$

In the polynomial above, $mm_{i,j}$ represents each element in the instrument matrix A, $mC1_{i,j}$ may be the linear coefficient vs. current C, $mT1_{i,j}$ may be the linear coefficient vs. temperature T, $mX1_{i,j}$ may be the linear coefficient vs. beam misalignment in the X direction, $mX2_{i,j}$ may be the quadratic coefficient vs. beam misalignment in the X direction, $mY1_{i,j}$ may be the linear coefficient vs. beam misalignment in the Y direction, $mY2_{i,j}$ may be the quadratic coefficient vs. beam misalignment in the Y direction, and $mXY1_{i,j}$ may be the first order crossterm coefficient vs. beam misalignments in the X and Y directions. Note that higher order terms and more cross terms may be added to the polynomial function to accommodate a wider range of possible operating conditions, and terms may be eliminated if the instrument matrix element changes over the corresponding operating condition range may be found to be minimal. The final step in compensating for errors in the instrument matrix A due to operating conditions may be to calculate "corrected" values for each element in the instrument matrix A at the current operating conditions, using the above polynomial function with the coefficients fixed at the values determined in step two.

Figure 18:
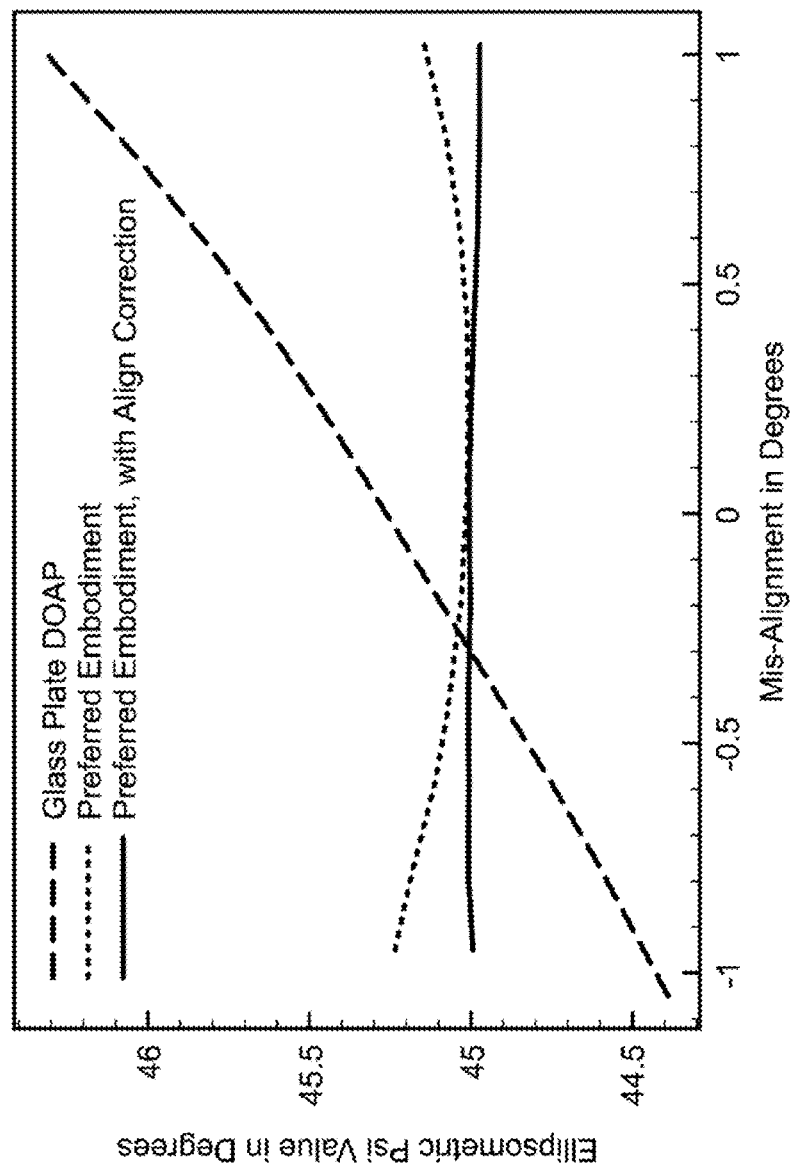
FIG. 18 is a graph of change in measured ellipsometric Psi value vs. misalignment, for various PSD configurations associated with embodiments of the present invention.

As an example of the effectiveness of the instrument matrix correction method, the experimental data in FIG. 18 shows ellipsometric Psi data vs. beam misalignment (in the "X" direction, which corresponds to beam tilts in the plane of incidence on the beam splitters). For a Glass Plate DOAP (dashed curve) which does not use a paired arrangement of beam splitters, the ellipsometric Psi data changes almost 2° over the ±1° beam misalignment range. Data acquired with one embodiment PSD 150 is shown as a dotted curve; the paired arrangement of beam splitters cancels out most of the misalignment errors, down to the few tenths of a degree level. The solid curve in FIG. 18 shows one embodiment PSD 150 data acquired with the just described correction method; the resulting data may be now corrected down to the hundredths of a degree level for data acquired over a beam misalignment range of ±1°.

System 200 may employ an off sample calibration before the system 200 may acquire ellipsometric data from a sample. The off sample calibration determines the azimuthal offsets of the PSG 110 and PSD 150 units with respect to the sample plane of incidence. In the off sample calibration procedure, the system may be first configured in the off sample mode, as previously described and shown in FIG. 2. Next, a sample 202 may be mounted and optionally aligned, as was previously described. System 200 may acquire an off sample calibration data set by acquiring raw data at multiple azimuthal orientations of the polarizer in the PSG 110, which in one embodiment includes four angles (−90°, −45°, 0°, and 45°). To analyze the off sample calibration data set, a Levenberg-Marquardt non-linear regression analysis of the off sample calibration data set may be performed, using the calculation model shown below.

$$\begin{pmatrix} SC1 \\ SC2 \\ SC3 \\ SC4 \end{pmatrix} = \begin{matrix} A \cdot Rot(rot_{PSD}) \cdot Sample \cdot Rot(rot_{PSG}) \cdot \\ PSG_{SV}(\theta, s_0, s_1, s_2, s_3, q) \end{matrix}$$

-continued
$$= A \cdot Rot(rot_{PSD}) \cdot \begin{pmatrix} 1 & -N & 0 & 0 \\ -N & 1 & 0 & 0 \\ 0 & 0 & C & S \\ 0 & 0 & -S & C \end{pmatrix} \cdot$$
$$Rot(rot_{PSG}) \cdot PSG_{SV}(\theta, s_0, s_1, s_2, s_3, q)$$

In the off sample regression analysis, all the parameters in the 4×4 instrument matrix A and PSG 110 Stokes vector $PSG_{SV}$ are fixed at the values determined in the instrument matrix calibration procedure. For the off sample calibration analysis, the model fit parameters are: $rot_{PSG}$ (the azimuthal offset of the PSG 110 unit), $rot_{PSD}$ (the azimuthal offset of the PSD 150 unit), and the sample 202 ellipsometric parameters N, C, and S, which are defined in terms of the traditional ellipsometric parameters ψ and Δ by N=cos(2ψ)), C=sin(2ψ)cos(Δ), and S=sin(2ψ)sin(Δ). Since the values for $rot_{PSG}$ and $rot_{PSD}$ should be independent of wavelength, the regression analysis simultaneously includes the calibration data sets from all the wavelengths. In one embodiment, the total number of data points in the analysis may be 64 (raw data acquired at 4 orientations of the polarizer, times 4 signals in each raw data point, times 4 wavelengths). The total number of fit parameters may be 14 (2 azimuthal rotation angles for the PSG 110 and PSD 150, plus 3 ellipsometric parameters N, C, and S at 4 wavelengths). Therefore, the fit may be overdetermined (that is, there are more data points than fit parameters), and the 2 off sample calibration parameters, $rot_{PSG}$ and $rot_{PSD}$, may be simultaneously and accurately determined along with the sample 202 ellipsometric parameters N, C, and S at all wavelengths. To exclude the effects of light source intensity and sample 202 reflectivity from the analysis, the acquired off sample Calibration Data Set and the corresponding Calculated Data Sets may be normalized by their average values in the analysis. The off sample calibration parameters $rot_{PSG}$ and $rot_{PSD}$ are stored for subsequent use in ellipsometric data acquisition.

To acquire ellipsometric data with the present invention, the following steps are performed. First the system may be configured in the off sample mode, as previously described and shown in FIG. 2. Next, a sample 202 may be mounted and optionally aligned, as described above. The polarizer mechanism in the PSG 110 may be adjusted to orient the polarizer in the data acquisition position, which in one embodiment may be +45°.

System 200 may acquire raw data, comprising signals S1, S2, S3, and S4, at each wavelength. System 200 may determine ellipsometric parameters from the raw data signals, using the equations below. The Mueller matrix expression below calculates the signals S1, S2, S3, and S4, using the Stokes vector of the light generated by the PSG 110, the azimuthal rotation angle of the PSG 110, the unnormalized ellipsometric parameters of the sample 202 (indicated by the parameters primed), the azimuthal rotation angle of the PSD 150, and the instrument matrix A. In this expression, the only unknown parameters are I (which may be related to the intensity of the light reflected from the sample 202), and the unnormalized ellipsometric parameters N', C', and S'. The signals S1, S2, S3, and S4 are measured, and the other parameters were previously determined in the instrument and off sample calibration.

$$\begin{pmatrix} S1 \\ S2 \\ S3 \\ S4 \end{pmatrix} = A \cdot Rot(rot_{PSD}) \cdot \begin{pmatrix} I & -N' & 0 & 0 \\ -N' & I & 0 & 0 \\ 0 & 0 & C' & S' \\ 0 & 0 & -S' & C' \end{pmatrix} \cdot$$

$$Rot(rot_{PSG}) \cdot PSG_{SV}(\theta, s_0, s_1, s_2, s_3, q)$$

Systems herein may calculate the Stokes vector elements of the light incidence on the sample 202, IS, using the expression below.

$$IS = \begin{pmatrix} is_0 \\ is_1 \\ is_2 \\ is_3 \end{pmatrix} = Rot(rot_{PSG}) \cdot PSG_{SV}(\theta, s_0, s_1, s_2, s_3, q)$$

The Stokes vector of the light entering the PSD 150, X, may be written as in the expression below.

$$X = \begin{pmatrix} x_0 \\ x_1 \\ x_2 \\ x_3 \end{pmatrix}$$

$$= Rot(rot_{PSD}) \cdot \begin{pmatrix} I & -N' & 0 & 0 \\ -N' & I & 0 & 0 \\ 0 & 0 & C' & S' \\ 0 & 0 & -S' & C' \end{pmatrix} \cdot IS$$

$$= \begin{pmatrix} I & -N' & 0 & 0 \\ -N' \cdot C_{rotPSD} & I \cdot C_{rotPSD} & -C' \cdot S_{rotPSD} & -S' \cdot S_{rotPSD} \\ -N' \cdot S_{rotPSD} & I \cdot S_{rotPSD} & C' \cdot C_{rotPSD} & S' \cdot C_{rotPSD} \\ 0 & 0 & -S' & C' \end{pmatrix} \cdot IS$$

with $C_{rotPSD} = \cos(rot_{PSD})$ and $S_{rotPSD} = \sin(rot_{PSD})$

Systems herein may calculate the values of the elements of X, $x_0$, $x_1$, $x_2$, and $x_3$, using the measured signal values S1, S2, S3, and S4, and the inverse of the instrument matrix $A^{-1}$ (this may be the fundamental equation of a DOAP, as was previously described).

$$X = \begin{pmatrix} x_0 \\ x_1 \\ x_2 \\ x_3 \end{pmatrix} = A^{-1} \cdot \begin{pmatrix} S1 \\ S2 \\ S3 \\ S4 \end{pmatrix}$$

Since the elements of X and IS are now known, the unnormalized ellipsometric parameters may be solved from the system of equations relating X and IS, resulting in the following expressions:

$$I = \frac{x_0 \cdot is_0 - (x_1 \cdot C_{rotPSD} + x_2 \cdot S_{rotPSD}) \cdot is_1}{is_0^2 - is_1^2}$$

$$N' = \frac{x_0 \cdot is_1 - (x_1 \cdot C_{rotPSD} + x_2 \cdot S_{rotPSD}) \cdot is_0}{is_0^2 - is_1^2}$$

$$C' = \frac{x_3 \cdot is_3 + (x_2 \cdot C_{rotPSD} - x_1 \cdot S_{rotPSD}) \cdot is_2}{is_2^2 + is_3^2}$$

$$S' = \frac{-x_3 \cdot is_2 + (x_2 \cdot C_{rotPSD} - x_1 \cdot S_{rotPSD}) \cdot is_3}{is_2^2 + is_3^2}$$

Systems herein may calculate ellipsometric parameters by the following expressions, wherein the a tan 2( ) function is the commonly used programming function which takes two arguments and returns angle in the correct quadrant, and P stands for degree of polarization, which is equal to 1 if the sample 202 does not depolarize the beam, and may be less than 1 if the sample 202 does depolarize the beam.

$$N = \frac{N'}{I}$$

$$C = \frac{C'}{I}$$

$$S = \frac{S'}{I}$$

$$\Psi = \frac{1}{2} a\tan\left(\frac{\sqrt{C^2 + S^2}}{N}\right)$$

$$\Delta = a\tan2(S, C)$$

$$P = \sqrt{N^2 + C^2 + S^2}$$

In the present invention, the preceding formulas are applied to the raw data signals acquired at each wavelength, and the calculated ellipsometric parameters are displayed and/or stored for further processing.

It is well-known that windows and lenses which are in the beam path of an ellipsometer system may affect the accuracy of the ellipsometric data acquired by the system. As discussed in "Windows in ellipsometry measurements", G. E. Jellison, Jr., Applied Optics Vol. 38, No. 22, page 4784, (1999), which is incorporated by reference herein in its entirety, windows or lenses which are in the beam path of an ellipsometer system can affect the accuracy of the ellipsometric data acquired by the system. Any small stress on glass components, which is often due to the mounting mechanism of the component, can induce birefringence in the component, which in turn can modify the polarization state of a beam which transmits through the component. Windows are used to provide optical access for the ellipsometer beam to allow measurements on a sample 202 inside a chamber 372, as drawn and previously discussed in FIG. 3. Lenses may be added to the beam path to reduce the spot size of the beam on the sample 202, as drawn and previously discussed in FIG. 2.

In the following discussion, the term "windows" may be used, but it may be understood that the same comments may be equivalently applied to "lenses" as well. It is well-known that three parameters are desired to accurately characterize the effects of two windows in the ellipsometer beam path (one window between the PSG 110 and sample 202, and the second window between the sample 202 and PSD 150). However, it is also well-known that even with an ellipsometer system that may measure the full Mueller matrix of a sample 202; it may be not possible to independently determine all three window parameters. In attempts to overcome this limitation, Jellison suggests the windows need to be measured separately, before the windows are installed on the chamber. This approach is not only inconvenient, but it may also limit the accuracy of the window characterization, as the process of mounting the windows on the chamber may induce or change the stress on the window, resulting in polarization properties which are different from those measured before the installation of the window To overcome this limitation in the present invention, system 200 may: 1) separately measure a reference sample 202 outside the chamber 372 without windows in the beam path to determine the optical model for the reference sample 202, 2) mount the reference sample 202 inside the chamber 372, 3) perform a windows calibration procedure, using the previously determined optical model for the reference sample 202, to determine the angle of incidence of the beam with respect to the sample 202 inside the change and the three window calibration parameters (at each wavelength in the ellipsometer system), and finally, 4) acquire accurate ellipsometric data using the three window calibration parameters to correct for the polarization effects of the windows present in the ellipsometer beam path. The following derivation of the present invention window correction procedure may use the below well-known notation. The Mueller matrix $M_W$, derived to the first order, for a window with a small retardation $\delta$ which may be oriented at an angle $\theta$, is shown below.

$$M_W = \begin{pmatrix} 1 & 0 & 0 & 0 \\ 0 & 1 & 0 & -S_W \\ 0 & 0 & 1 & C_W \\ 0 & S_W & -C_W & 1 \end{pmatrix}$$

$$C_W = \delta\cos(\theta)$$

$$S_W = \delta\sin(\theta)$$

If windows are placed before and after the sample 202 in the beam path, the resulting Mueller matrix expression $M_{SampWin}$ is:

$$M_{SampWin} = M_{W1} \cdot Samp \cdot M_{W0}$$

$$= \begin{pmatrix} 1 & 0 & 0 & 0 \\ 0 & 1 & 0 & -S_1 \\ 0 & 0 & 1 & C_1 \\ 0 & S_1 & -C_1 & 1 \end{pmatrix} \cdot \begin{pmatrix} 1 & -N & 0 & 0 \\ -N & 1 & 0 & 0 \\ 0 & 0 & C & S \\ 0 & 0 & -S & C \end{pmatrix} \cdot$$

$$\begin{pmatrix} 1 & 0 & 0 & 0 \\ 0 & 1 & 0 & -S_0 \\ 0 & 0 & 1 & C_0 \\ 0 & S_0 & -C_0 & 1 \end{pmatrix}$$

$$= \begin{pmatrix} 1 & -N & 0 & S_0 \cdot N \\ -N & 1 & S_1 \cdot S & -S_0 - S_1 \cdot C \\ 0 & S_0 \cdot S & C - W \cdot S & S + W \cdot C \\ -S_1 \cdot N & S_1 + S_0 \cdot C & -(S + W \cdot C) & C - W \cdot S \end{pmatrix}$$

$$S_0 = \delta_0 \sin(\theta_0)$$

$$S_1 = \delta_1 \sin(\theta_1)$$

$$W = \delta_o \cos(\theta_0) + \delta_1 \cos(\theta_1)$$

In the above expression for $M_{SampWin}$, note that the sample ellipsometric parameter N is not affected by the windows (at least to the first order), while the W window parameter, which may be a sum of components from the windows, combines indistinguishably with the sample's C and S ellipsometric parameters.

A first step in the present invention window correction procedure may be to ellipsometrically measure and analyze a reference sample 202, without windows in the beam path. The result of the analysis may be an optical model which represents the sample 202, and with the optical model, systems herein may calculate ellipsometric parameters N, C, and S for any angle of incidence.

A second step of the present invention window correction procedure may be to determine elements of the $M_{SampWin}$ matrix. This may be done by mounting the previously measured and analyzed reference sample 202 in the chamber 372, with the windows in the beam path. System 200 may acquire a windows calibration data set, using multiple orientations of the polarizer in the PSG 110. In one embodiment, system 200 may acquire and store raw data at polarizer azimuthal angles of $-90°$, $-45°$, $0°$, and $45°$. To analyze the window calibration data set, a Levenberg-Marquardt non-linear regression analysis of the window calibration data set may be performed, using the calculation model shown below.

$$\begin{pmatrix} SC1 \\ SC2 \\ SC3 \\ SC4 \end{pmatrix} = A \cdot Rot(rot_{PSD}) \cdot M_{SampWin} \cdot Rot(rot_{PSG}) \cdot PSG_{SV}(\theta, s_0, s_1, s_2, s_3, q)$$

$$= A \cdot Rot(rot_{PSD}) \cdot \begin{pmatrix} 1 & a & 0 & 0 \\ a & 1 & b & 0 \\ 0 & c & d & e \\ f & g & -e & d \end{pmatrix} \cdot Rot(rot_{PSG}) \cdot$$

$$PSG_{SV}(\theta, s_0, s_1, s_2, s_3, q)$$

In the calculation model above, elements in the $M_{SampWin}$ matrix have been replaced with parameters a, b, c, d, e, f, and g. In the window calibration regression analysis, all the parameters in the 4×4 instrument matrix A and PSG 110 Stokes vector $PSG_{SV}$ are fixed at the values determined in the instrument matrix calibration procedure. For the window calibration analysis, the model fit parameters are: $rot_{PSG}$ (the azimuthal offset of the PSG 110 unit), $rot_{PSD}$ (the azimuthal offset of the PSD 150 unit), and the Mueller matrix elements of the $M_{SampWin}$ matrix a, b, c, d, e, f, and g. Since the values for $rot_{PSG}$ and $rot_{PSD}$ should be independent of wavelength, the regression analysis simultaneously includes the calibration data sets from all the wavelengths. In one embodiment, the total number of data points in the analysis may be 64 (raw data acquired at 4 orientations of the polarizer, times 4 signals in each raw data point, times 4 wavelengths). The total number of fit parameters may be 30 (2 azimuthal rotation angles for the PSG 110 and PSD 150, plus 7 $M_{SampWin}$ matrix elements at 4 wavelengths). Therefore, the fit may be overdetermined, and the 2 off sample calibration parameters, $rot_{PSG}$ and $rot_{PSD}$, may be simultaneously and accurately determined along with the $M_{SampWin}$ matrix elements at all wavelengths. To exclude the effects of light source intensity and sample 202 reflectivity from the analysis, the acquired Window Calibration Data Set and the corresponding Calculated Data Sets are normalized by their average values in the analysis.

A third step in the present invention window correction procedure may be to determine the angle of incidence of the beam with respect to the reference sample. From the Window Calibration analysis, the ellipsometric parameter N may be now known at each wavelength, as $N=-a$. The N values at each wavelength now serve as an Angle Determination Data Set. The optical model for the reference sample 202, determined in the first step of the Window Correction Procedure, may be used to calculate values of N vs. angle of incidence. The angle of incidence may be the only fit parameter in the Angle Determination analysis. Systems herein may determine the angle of incidence via a well-known Levenberg-Marquardt non-linear regression analysis of the Angle Determination Data Set using the optical model for the reference sample 202 which was determined in step one. Once system 200 determines the angle of incidence, system 200 may calculate the ellipsometric parameters for the reference sample 202 N, C, and S at each wavelength, and these values will be used in the next step of the window correction procedure.

A fourth step in the present invention window correction procedure may be to determine the window correction parameters, which may be also done using non-linear regression analysis. The data sets for this analysis are the Mueller matrix elements determined in the Window Calibration analysis. The calculation model may be specified by the original definition of the $M_{SampWin}$ matrix, as shown below. The N, C, and S parameters are fixed at values calculated from the optical model determined in the Angle Determination analysis, and the fitting parameters are the window parameters $S_0$, $S_1$, and W.

$$b = S_1 \cdot S \quad c = S_0 \cdot S \quad d = C - W \cdot S$$

$$f = -S_1 \cdot N \quad g = S_1 + S_0 \cdot C \quad e = S + W \cdot C$$

System 200 may perform a Levenberg-Marquardt non-linear regression analysis separately at each wavelength, resulting in the window parameters $S_0$, $S_1$, and W at each wavelength, which are stored and used as correction factors when acquiring subsequent ellipsometric data sets.

A additional step in the present invention window correction procedure may be to acquire accurate ellipsometric data on samples, with windows in the beam path, using the previously determined window parameters as correction factors. The window correction procedure for acquiring accurate ellipsometric data with windows in the beam path may be derived as follows. The Stokes vector IS of light incident on the sample 202, after passing through the first window, is given by:

$$IS = \begin{pmatrix} is_0 \\ is_1 \\ is_2 \\ is_3 \end{pmatrix} = Rot(rot_{PSG}) \cdot \begin{pmatrix} 1 & 0 & 0 & 0 \\ 0 & 1 & 0 & -S_0 \\ 0 & 0 & 1 & W \\ 0 & S_0 & -W & 1 \end{pmatrix} \cdot PSG_{SV}(\theta, s_0, s_1, s_2, s_3, q)$$

In the above expression, systems herein may calculate the Stokes vector from the PSG 110 using values previously determined in the instrument matrix calibration procedure, and the $rot_{PSG}$, $S_0$, and W values were previously determined in the window correction procedure. The Mueller matrix expression that may be used to calculate the intensity signals measured by the detectors S1, S2, S3, and S4 is:

$$\begin{pmatrix} S1 \\ S2 \\ S3 \\ S4 \end{pmatrix} = A \cdot M_{W1} \cdot Rot(rot_{PSD}) \cdot Samp \cdot IS$$

$$= A \cdot \begin{pmatrix} 1 & 0 & 0 & 0 \\ 0 & 1 & 0 & -S_1 \\ 0 & 0 & 1 & 0 \\ 0 & S_1 & 0 & 1 \end{pmatrix} \cdot Rot(rot_{PSD}) \cdot \begin{pmatrix} I & -N' & 0 & 0 \\ -N' & I & 0 & 0 \\ 0 & 0 & C' & S' \\ 0 & 0 & -S' & C' \end{pmatrix} \cdot IS$$

Pre-multiplying each side of the preceding expression by $Rot(rot_{PSD})^{-1} \cdot M_{W1}^{-1} \cdot A^{-1}$ yields:

$$Rot(rot_{PSD})^{-1} \cdot M_{W1}^{-1} \cdot A^{-1} \cdot \begin{pmatrix} S1 \\ S2 \\ S3 \\ S4 \end{pmatrix} = X$$

$$= \begin{pmatrix} I & -N' & 0 & 0 \\ -N' & I & 0 & 0 \\ 0 & 0 & C' & S' \\ 0 & 0 & -S' & C' \end{pmatrix} \cdot IS$$

$$X = \begin{pmatrix} x0 \\ x1 \\ x2 \\ x3 \end{pmatrix}$$

$$= Rot(-rot_{PSD}) \cdot \begin{pmatrix} 1 & 0 & 0 & 0 \\ 0 & \frac{1}{S_1^2+1} & 0 & \frac{S_1}{S_1^2+1} \\ 0 & 0 & 1 & 0 \\ 0 & -\frac{S_1}{S_1^2+1} & 0 & \frac{1}{S_1^2+1} \end{pmatrix} \cdot A^{-1}$$

The above expression calculates the Stoke vector X, which may be for the beam immediately after reflecting from the sample 202, in terms of the inverse of the instrument matrix $A^{-1}$, the inverse of the matrix for the second window $M_{W1}^{-1}$, and the inverse of the rotation matrix for the detector, using the identity $Rot(x)^{-1} = Rot(-x)$. Having computed the elements of the X and IS Stokes vectors $x_0$, $x_1$, $x_2$, $x_3$, $is_0$, $is_1$, $is_2$, and $is_3$, systems herein may calculate the unnormalized ellipsometric values for the sample 202 by:

$$I = \frac{x_0 \cdot is_0 - x_1 \cdot is_1}{is_0^2 - is_1^2}$$

$$N' = \frac{x_0 \cdot is_1 - x_1 \cdot is_0}{is_0^2 - is_1^2}$$

$$C' = \frac{x_3 \cdot is_3 + x_2 \cdot is_2}{is_2^2 + is_3^2}$$

$$S' = \frac{-x_3 \cdot is_2 + x_2 \cdot is_3}{is_2^2 + is_3^2}$$

Systems herein may calculate normalized ellipsometric parameters N, C, and S, and other related quantities as previously shown, and the resulting values may be displayed and/or stored for further processing.

Figure 19:
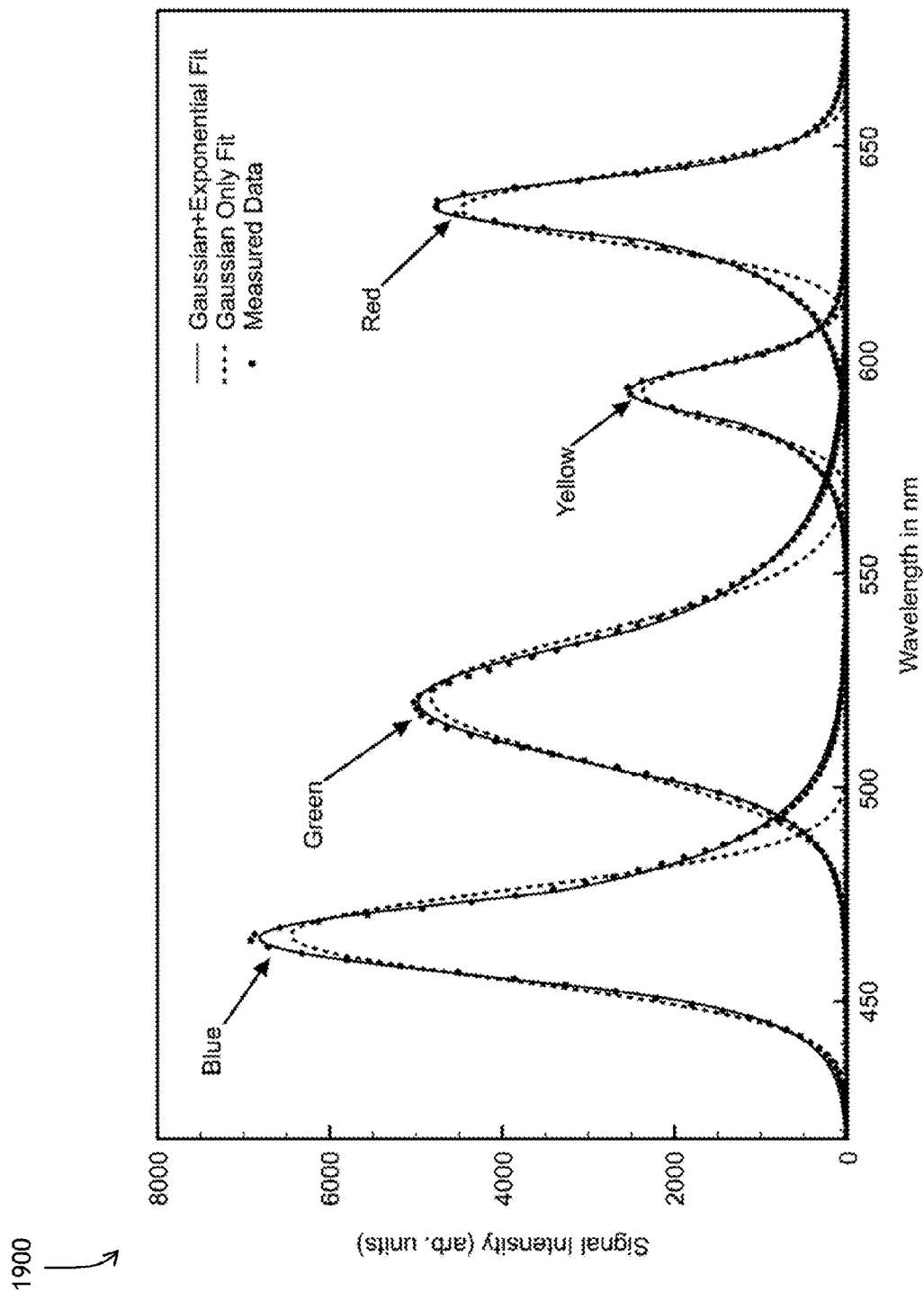
FIG. 19 is a graph of Spectral intensity profiles for visible LED light sources, with lineshape fit curves associated with one embodiment of the present invention.

Embodiments of the present invention improve the accuracy of optical model-based analysis of acquired ellipsometric data sets. As previously mentioned, one disadvantage of using light emitting diodes (LED's) for light sources may be their large bandwidth. This is illustrated by FIG. 19, which shows the measured intensity spectrum vs. wavelength for 4 LED's (blue, green, yellow, and red) as filled circle symbols. The dashed lines on the FIG. 19 are from a least squares fit to the measured data sets assuming a Gaussian lineshape, which may be a well-known method. The Gaussian lineshape does not fit the measured LED intensity vs. wavelength curves very well: the peak height and position of the dashed Gaussian curves do not match the measured data circles, and the data fit in the tail regions may be also poor, due to the asymmetrical, broad tails in the measured data. In the present invention, a significantly improved fit to the measured LED lineshape spectra may be provided by a piece-wise continuous function of Gaussian and Exponential lineshapes. The present invention Gaussian+Exponential lineshape function GE(x) is defined as:

$$\text{If } x < P - \frac{W}{2} \text{ then } GE(x) = \frac{A}{2} \cdot e^{-\left(\frac{P-\frac{W}{2}-x}{L}\right)}$$

$$\text{If } x > P + \frac{W}{2} \text{ then } GE(x) = \frac{A}{2} \cdot e^{-\left(\frac{x-P-\frac{W}{2}}{R}\right)}$$

$$\text{Otherwise } GE(x) = A \cdot e^{-\left(\frac{x-P}{W \cdot K}\right)^2}, \quad K = \frac{1}{2\sqrt{-\ln\left(\frac{1}{2}\right)}}$$

where x is in nm, A is the amplitude, P is the peak wavelength of the Gaussian in nm, W is the full width half maximum (FWHM) of the lineshape in nm, L is the decay constant for the left exponential tail, R is the decay constant for the right exponential tail, and the constant K adjusts the amplitude of the Gaussian expression to ½ at the FWHM points defined by W.

Figure 20:
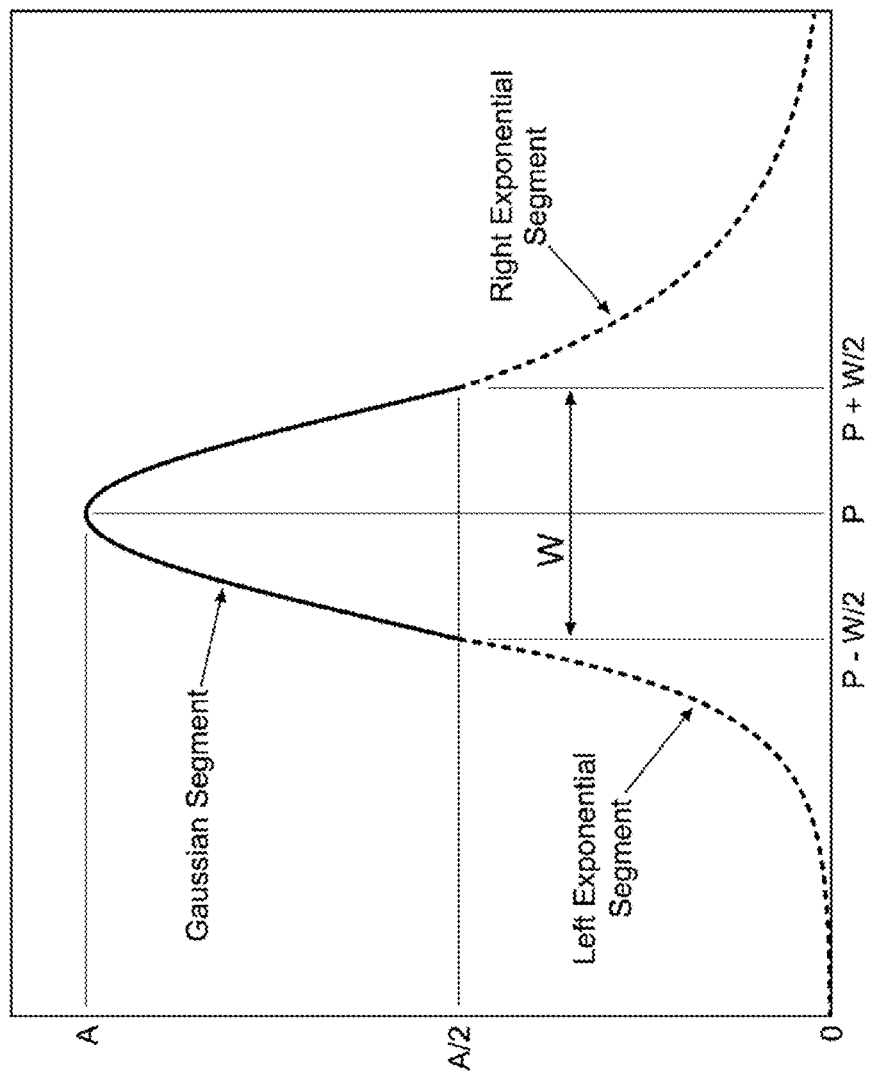
FIG. 20 is a graph of piece-wise continuous Gaussian+ Exponential lineshape fitting function associated with one embodiment of the present invention.

FIG. 20 illustrates the piece-wise continuous Gaussian+Exponential lineshape function GE(x). Note that the present invention Gaussian+Exponential lineshape function does have a discontinuity in its derivatives at the transition between the Gaussian and Exponential segments, which may limit the general applicability of this lineshape. However, in the present invention, the Gaussian+Exponential lineshape function provides excellent fits to the measured LED lineshapes, and requires only 2 additional parameters, L and R, to fit the asymmetrical tails of the measured LED lineshapes.

System 200 may take a first step in improving the data analysis accuracy including measuring the intensity spectrum of each light source in the system. Next, system 200 may fit the intensity spectrum for each light source using the Gaussian+Exponential lineshape function previously described. For the spectra shown in FIG. 19, the Gaussian+Exponential lineshape characterizing parameters, as determined by a nonlinear least-squares regression analysis of the measured spectra, are shown in FIG. 23. For comparison, FIG. 23 also lists the lineshape characterizing parameters using a Gaussian-only lineshape. The final step in improving the data analysis accuracy with the present invention may be to incorporate the measured lineshape functions into the optical model which may be used to generate calculated data in the analysis of the ellipsometric data. Well-known descriptions of ideal optical model calculation may assume illumination of the sample 202 by monochromatic light. The output of the optical model calculation are the complex $r_p$ and $r_s$ reflectivities for the model at each wavelength. If the illuminating light is not monochromatic, measured response may be a weighted sum over all the light source wavelengths which are illuminating the sample 202. Mathematically, this may be written as the well-known convolution integral:

$$M(\lambda) = \int S(\lambda') b(\lambda'-\lambda) d\lambda'$$

In the convolution integral above, S(λ) may be the ideal function and b(λ'-λ) may be the lineshape function, which are convolved together to form the measured function M(λ). Since the multiple wavelengths illuminating the sample 202 are not coherent with each other, the convolution must be done over calculated intensity values (to suppress the interference between multiple wavelengths), as opposed to calculated field amplitudes (which maintain the interference between multiple wavelengths). However, the intensity convolution must still maintain the phase information which may be measured by ellipsometry. This situation may be analogous to the films with non-uniform thickness measured by Jellison "Sample depolarization effects from thin films of ZnS on GaAs as measured by spectroscopic ellipsometry", G. E. Jellison, Jr., and J. W. McCamy, Appl. Phys. Lett. (Vol. 61, No. 5, page 512, 1992), and the incoherent substrate backside reflection studied by Joerger "Influence of incoherent superposition of light on ellipsometric coefficients", R. Joerger, et. al., (Applied Optics Vol. 36, No. 1, page 319, 1997), both of which are incorporated by reference herein in their entirety. Joerger shows that for ellipsometry, the quantities to be integrated are $|r_p|^2$, $|r_s|^2$, $\text{Re}(r_p r_s^*)$, and $\text{Im}(r_p r_s^*)$, which correspond to the intensities of p-polarized and s-polarized reflected light, and the real and imaginary parts of the product of $r_p$ and the complex conjugate of $r_s$. The appropriate convolution integrals to account for the light source bandwidth are written as:

$$\langle R_p \rangle = \int |r_p(\lambda')|^2 GE(\lambda'-\lambda) d\lambda'$$

$$\langle R_s \rangle = \int |r_s(\lambda')|^2 GE(\lambda'-\lambda) d\lambda'$$

$$Re\langle r_p r_s^* \rangle = \int Re(r_p(\lambda') \cdot r_s(\lambda')^*) GE(\lambda'-\lambda) d\lambda'$$

$$Im\langle r_p r_s^* \rangle = \int Im(r_p(\lambda') \cdot r_s(\lambda')^*) GE(\lambda'-\lambda) d\lambda'$$

The $r_p(\lambda)$ and $r_s(\lambda)$ functions are evaluated by the ideal optical model calculation, and the GE(λ) function may be the Gaussian+Exponential lineshape function, with the parameters previously determined from the spectral measurement of the light source. The < > brackets indicate the convolved or "averaged" values. The integrals may be numerically evaluated using Simpson's rule, and more complex numerical integration algorithms such as Gaussian Quadrature. The formulas to calculate the measured ellipsometric parameters from the averaged values are also found in the Joerger paper, but the formulas below have been simplified and switched to the N, C, S notation used throughout the rest of this disclosure.

$$N = \frac{\langle R_s \rangle - \langle R_p \rangle}{\langle R_s \rangle + \langle R_p \rangle}$$

$$C = \frac{2 \cdot Re\langle r_p r_s^* \rangle}{\langle R_s \rangle + \langle R_p \rangle}$$

$$S = \frac{2 \cdot Im\langle r_p r_s^* \rangle}{\langle R_s \rangle + \langle R_p \rangle}$$

$$P = \sqrt{N^2 + C^2 + S^2}$$

Figure 21:
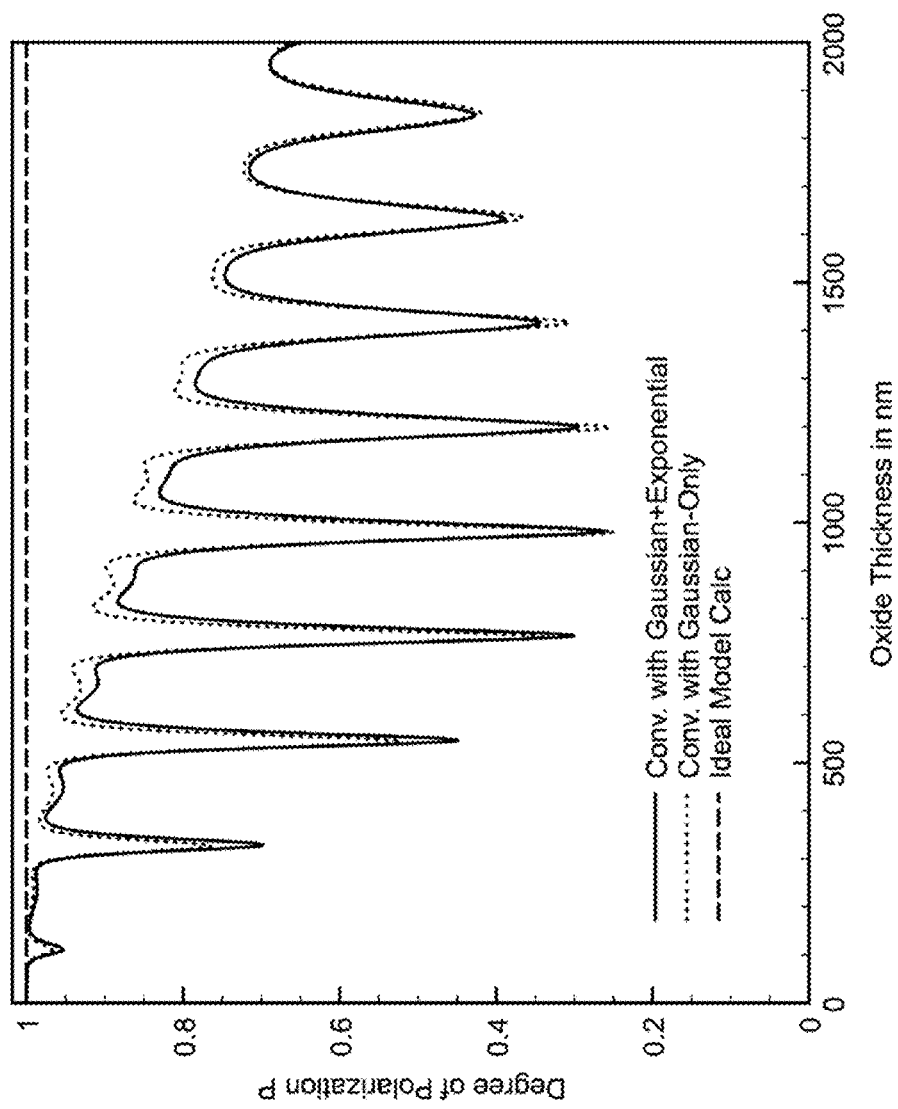
FIG. 21 is a graph of calculated Degree of Polarization data vs. oxide thickness, with different convolution lineshapes associated with one embodiment of the present invention.
Figure 22:
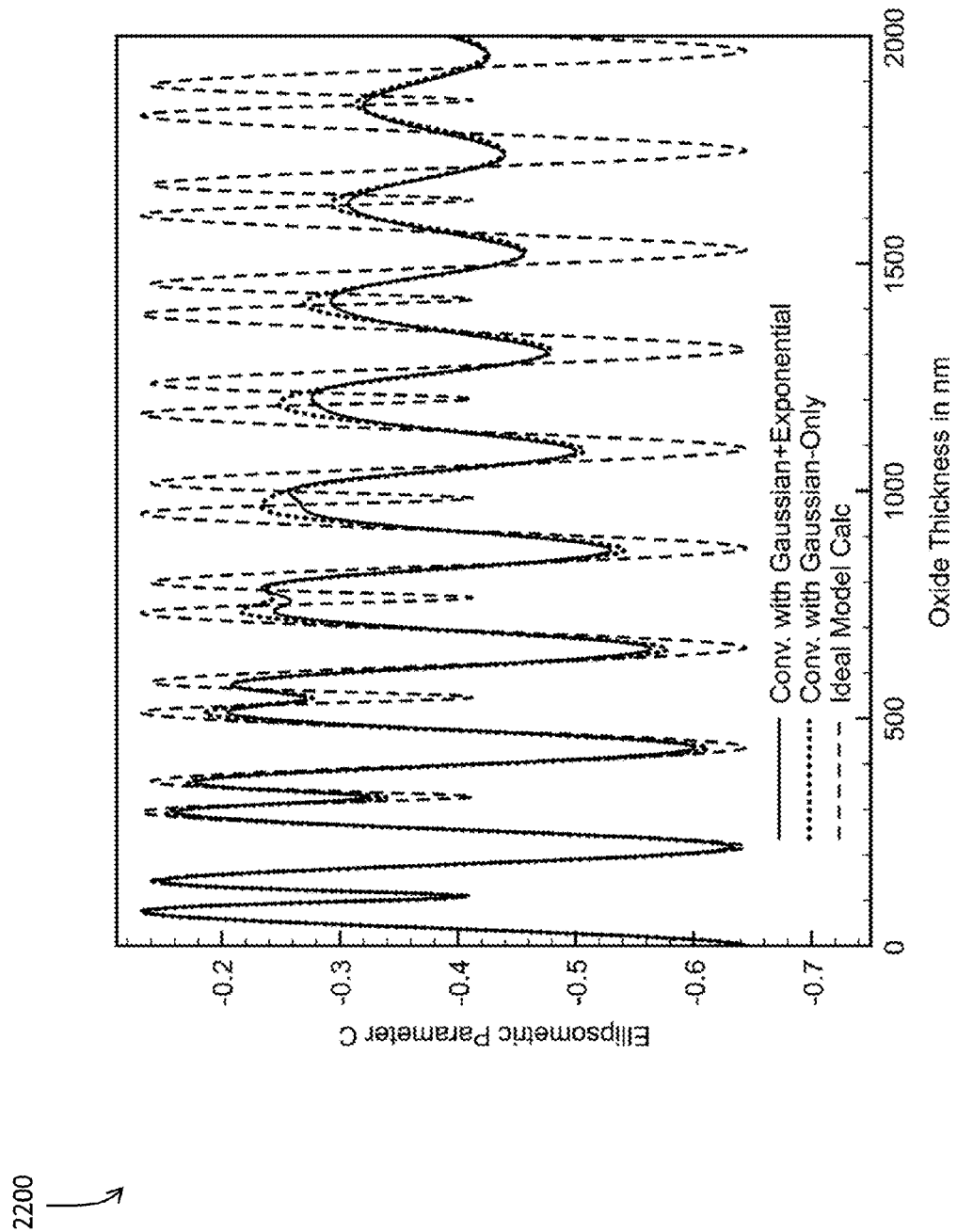
FIG. 22 is a graph of calculated Ellipsometric Parameter C vs. oxide thickness, with different convolution lineshapes associated with one embodiment of the present invention.

It should be noted that the degree of polarization P may in general be less than one, due to the depolarizing effects of the large bandwidth LED light source, but the value of P may be highly dependent on the thickness of the film on the sample 202. An example of the optical model calculation including the effects of the large LED bandwidth is shown in FIGS. 21 and 22. For this example, the optical model used a silicon substrate with a silicon dioxide film, an angle of incidence of 65°, and the lineshape characterizing parameters of the green LED shown in FIG. 23. The optical model was calculated over a range of film thicknesses, from 0 to 2000 nm. FIG. 21 plots the degree of polarization P vs. film thickness. The degree of polarization for the ideal model calculation (dashed line) is constant and equal to one. The degree of polarization curves for the model calculation using convolution with the Gaussian+Exponential lineshape (solid line) and Gaussian-Only lineshape (dotted line) exhibit significant structure vs. film thickness. While the structure may be similar, there are still noticeable differences between the curves calculated using convolution with the Gaussian+Exponential lineshape and the Gaussian-Only lineshape.

FIG. 22 shows a similar comparison plot, but for the ellipsometric parameter C. The ideal model calculation curve (dashed line) shows oscillations of essentially constant amplitude vs. thickness. The amplitude of the oscillations in the curves calculated with bandwidth convolution dampen out with increasing thickness. Again, noticeable differences are observed between the curves calculated with Gaussian+Exponential lineshape convolution (solid line) and Gaussian-Only lineshape convolution (dotted line). Especially at certain film thicknesses where the difference between the curves may be large, not using one embodiment Gaussian+Exponential lineshape in the light source bandwidth convolution integral may induce significant errors in the ellipsometric data analysis.

FIG. 23 shows a table of a table of lineshape characterizing parameters for the LED spectral intensity profiles associated with one embodiment of the present invention.

Figure 24A:
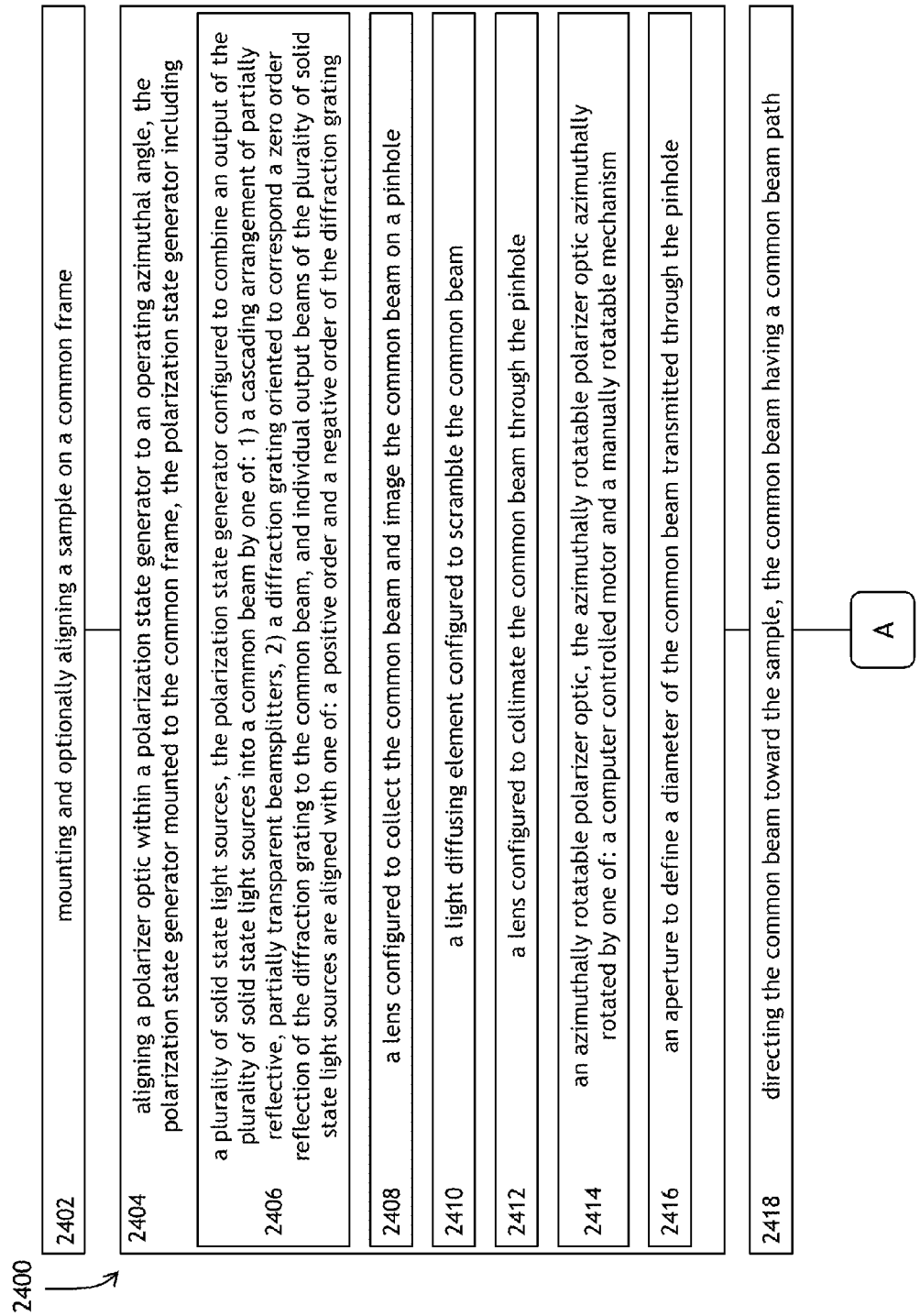

FIGS. 24A and 24B show a flow diagram of a method acquiring ellipsometric data exemplary of an embodiment of the present invention. Method 2400 may begin, at step 2402, with mounting and optionally aligning a sample on a common frame and, at step 2404, with aligning a polarizer optic within a polarization state generator to an operating azimuthal angle, the polarization state generator mounted to the common frame, the polarization state generator may include, at step 2406, a plurality of solid state light sources, the polarization state generator configured to combine an output of the plurality of solid state light sources into a common beam by one of: 1) a cascading arrangement of partially reflective, partially transparent beamsplitters, or 2) a diffraction grating oriented to correspond a zero order reflection of the diffraction grating to the common beam and individual output beams of the plurality of solid state light sources are aligned with one of: a positive order and a negative order of the diffraction grating and, at step 2408, with a lens configured to collect the common beam and image the common beam on a pinhole and, at step 2410, with a light diffusing element configured to scramble the common beam and, at step 2412, with a lens configured to collimate the common beam through the pinhole and, at step 2414, with an azimuthally rotatable polarizer optic, the azimuthally rotatable polarizer optic azimuthally rotated by one of: a computer controlled motor and a manually rotatable mechanism and, at step 2416, with an aperture to define a diameter of the common beam transmitted through the pinhole. Method 2400 may continue at step 2418 with directing the common beam toward the sample, the common beam having a common beam path and, at step 2420, with receiving an incident beam transmission from the sample within a no moving parts polarimeter, the no moving parts polarimeter mounted to the common frame, the no moving parts polarimeter including: and, at step 2422, with a plurality of detectors configured for receiving the incident beam and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal and a seventh detector D7 creating a seventh detector signal and, at step 2424, with receiving a plurality of detector signals for at least one wavelength from the plurality of detectors configured for receiving the incident beam and, at step 2426, with arranging the plurality of detector signals into a four by one signal vector for the at least one wavelength and, at step 2428, with multiplying the four by one signal vector for the at least one wavelength by an inverse of a four by four instrument matrix to form at least one four by one product vector, the four by four instrument matrix based on a calibration of the polarization state generator and the no moving parts polarimeter and, at step 2430, with determining at least one effective ellipsometric data parameter for the at least one wavelength based on the at least one four by one product vector and, at step 2432, with storing the determined at least one effective ellipsometric data parameter for a further processing and, method 2400 may conclude at step 2434, with displaying the at least one effective ellipsometric data parameter to a user on a display.

CONCLUSION

Specific blocks, sections, devices, functions, processes and modules may have been set forth. However, a skilled technologist will realize that there are many ways to partition the system, and that there are many parts, components, processes, modules and functions that may be substituted for those listed above.

While the above detailed description has shown, described and pointed out the fundamental novel features of the invention as applied to various embodiments, it will be understood that various omissions and substitutions and changes in the form and details of the system illustrated may be made by those skilled in the art, without departing from the intent of the invention. The foregoing description details certain embodiments of the invention. It will be appreciated, however, that no matter how detailed the foregoing appears, the invention may be embodied in other specific forms without departing from its spirit and essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that a preferred vehicle may vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, and predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device-detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware may be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is shown/described herein as a single illustrated figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be the of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art may understand the convention (e.g., "a system having at least one of A, B, and C" may include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art may understand the convention (e.g., "a system having at least one of A, B, or C" may include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A multiple wavelength ellipsometer device, comprising:
   a polarization state generator, including:
      a plurality of solid state light sources; and
   a no moving parts polarimeter, including:
      a first polarimeter section configured to receive an incident beam;
      a plurality of detectors configured for receiving the incident beam and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal, and a seventh detector D7 creating a seventh detector signal;
      a second polarimeter section including a first partially reflecting optic oriented to partially reflect the incident beam at a first (+A) angle with respect to the incident beam, the first partially reflecting optic configured to partially reflect the incident beam to the first detector (D1) and to transmit a first remaining incident beam;
      a third polarimeter section including a second partially reflecting optic oriented to partially reflect the first remaining incident beam at a second angle (−A) with respect to the first remaining incident beam, the second partially reflecting optic configured to partially reflect the first remaining incident beam to the second detector (D2) and transmit a second remaining incident beam;
      a fourth polarimeter section including a third partially reflecting optic oriented to partially reflect the second remaining incident beam at a third angle (+B) with respect to the second remaining incident beam, the third partially reflecting optic configured to partially reflect the second remaining incident beam to the third detector (D3) and transmit a third remaining incident beam;
      a fifth polarimeter section including a fourth partially reflecting optic oriented to partially reflect the third remaining incident beam at a fourth angle (−B) with respect to the third remaining incident beam, the fourth partially reflecting optic configured to partially reflect the third remaining incident beam to the fourth detector (D4) and transmit a fourth remaining incident beam;
      a sixth polarimeter section including a fifth partially reflecting optic oriented to partially reflect the fourth remaining incident beam at a fifth angle (+C) with respect to the fourth remaining incident beam, the fifth partially reflecting optic configured to partially reflect the fourth remaining incident beam to the fifth detector (D5) and transmit a fifth remaining incident beam; and
      a seventh polarimeter section including a sixth partially reflecting optic oriented to partially reflect the fifth remaining incident beam at a sixth angle (−C) with respect to the fifth remaining incident beam, the sixth partially reflecting optic configured to partially reflect the fifth remaining incident beam to the sixth detector (D6) and transmit a sixth remaining incident beam to the seventh detector (D7);
      at least one retarder element, said at least one retarder positioned in at least one of: between the first section and the second polarimeter section, between the third polarimeter section and the fourth polarimeter section, or between the fifth polarimeter section and the sixth polarimeter section.

2. The multiple wavelength ellipsometer device of claim 1, further comprising a sample housing configured to receive and support a sample and a common frame configured to receive and orient the polarization state generator, the sample housing, and the no moving parts polarimeter, and wherein the polarization state generator further includes:
   the plurality of solid state light sources configured to combine an output of the plurality of solid state light sources into a common beam by at least one of: 1) a cascading arrangement of partially reflective, partially transparent beamsplitters, or 2) a diffraction grating oriented to correspond a zero order reflection of the diffraction grating to the common beam with individual output beams of the plurality of solid state light sources being aligned with a positive order or a negative order of the diffraction grating;

a first lens configured to collect the common beam and image the common beam on a pinhole;

a second lens configured to collimate the common beam through the pinhole;

an azimuthally rotatable polarizer optic azimuthally rotated by a computer controlled motor or a manually rotatable mechanism; and an aperture to define a diameter of the common beam transmitted through the pinhole.

3. The multiple wavelength ellipsometer device of claim 2, further comprising:

a light diffusing element associated with the polarization state generator, configured to scramble the common beam, and positioned prior to the pinhole, wherein the plurality of solid state light sources is four light sources, and the cascading arrangement of partially reflective, partially transparent beamsplitters is implemented by three beamsplitters, a first beamsplitter is configured to combine the individual output beams of a first light source and a second light source into a first common beam, a second beamsplitter is configured to combine the individual output beams from a third light source and a fourth light source into a second common beam, and a third beamsplitter is configured to combine the first common beam and the second common beam.

4. The multiple wavelength ellipsometer device of claim 2, wherein the manually rotatable mechanism is an azimuthally rotatable polarizer plate configured to mount with the azimuthally rotatable polarizer optic, the azimuthally rotatable polarizer plate configured to rotatably couple between a front plate and a back plate, said azimuthally rotatable polarizer plate rotatably coupled to the front plate via a bushing, the front plate configured with a plurality of azimuthally spatial detents, the azimuthally rotatable polarized plate further configured with a plurality of azimuthally spatial ball plungers alignable with the azimuthally spatial detents, wherein the azimuthally rotatable polarized plate, the plurality of azimuthally spatial ball plungers, and the plurality of azimuthally spatial detents are positioned for at least one of: 1) selectably rotating the azimuthally rotatable polarized plate to cause extraction of at least one ball plunger from at least one detent, 2) selectably rotating the azimuthally rotatable polarizer plate around the bushing to align at least one ball plunger with at least one detent, and 3) selectably rotating the azimuthally rotatable polarized plate to cause insertion of at least one ball plunger into at least one detent to secure the azimuthally rotatable polarizer plate in azimuth with the front plate.

5. The multiple wavelength ellipsometer device of claim 1, wherein the partially reflecting optics are uncoated transparent glass plates, and each of the first angle, the third angle, and the fifth angle is 90 degrees positive to each incident beam and each of the second angle, the fourth angle, and the sixth angle is 90 degrees negative from each incident beam.

6. The multiple wavelength ellipsometer device of claim 1, wherein the seventh detector D7 is a position sensitive detector and the first polarimeter section includes a focusing lens.

7. The multiple wavelength ellipsometer device of claim 2, further comprising:

a plurality of analog circuits configured to combine the detector signal from each of the detectors, wherein a first analog circuit of the plurality of analog circuits is configured to combine the first detector signal D1 and second detector signal D2 to create a first combined signal S1, a second analog circuit of the plurality of analog circuits is configured to combine the third detector signal D3 and the fourth detector signal D4 to create a second combined signal S2, and a third analog circuit of the plurality of analog circuits is configured to combine the fifth detector D5 signal and the sixth detector D6 signal to create a third combined signal S3; and a processor configured to:

receive the seventh detector signal D7 and the first S1, second S2, and third S3 combined signals;

digitize and store each of the received signals; and configure each of the received signals for a further processing.

8. The multiple wavelength ellipsometer device of claim 7, wherein the processor is further configured for control of the plurality of solid state light sources, the control including:

sequentially cycling the plurality of solid state light sources through a series of states, each of the series of states including at least one of: at least one solid state light source illuminated or none of the solid state light source illuminated;

receiving the seventh detector signal D7 and the first, second, and third combined signals;

digitizing and storing each of the received signals; and configuring each of the received signals for further processing.

9. The multiple wavelength ellipsometer device of claim 1, wherein each partially reflecting optic is configured to mount within a common base, the common base including a plurality of mounting slots in the common base, each of the plurality of mounting slots configured to receive one partially reflecting optic, each of the plurality mounting slots having a mounting surface configured to adhesively couple with a portion of one surface of the one partially reflecting optic, each of the mounting slots sized greater than the one partially reflecting optic allowing all surfaces of the one partially reflecting optic other than the portion of one surface to remain free from contact with the common base.

10. The multiple wavelength ellipsometer device of claim 2, wherein the sample is adjustably mounted to the common frame, and wherein the common frame is further configured for orientation of the multiple wavelength ellipsometer device for a plurality of ellipsometer operations including at least one of:

a straight through mode of ellipsometer operation wherein the common beam is directly pointed into the polarimeter;

an off sample mode of ellipsometer operation wherein the common beam is:
directed toward a sample and
at least one of:
reflected from the sample into the polarimeter or
transmitted through the sample into the polarimeter; and an in situ mode of ellipsometer operation wherein the common frame includes a chamber and the sample is adjustably mounted within the chamber, the chamber having a first window for 1) receiving the common beam and 2) transmitting the received common beam to the sample and a second window for 1) receiving a reflected beam from the sample and 2) transmitting the reflected beam to the no moving parts polarimeter.

11. The multiple wavelength ellipsometer device of claim 10, wherein the multiple wavelength ellipsometer device is configured for calibration to determine a four by four instrument matrix for a wavelength, the calibration comprising the steps of:

configuring the multiple wavelength ellipsometer device in the straight through mode;

inserting a rotatable calibration waveplate into a common beam path between the polarization state generator and the no moving parts polarimeter;

rotating the calibration waveplate to at least two azimuthal orientations;

rotating the azimuthally rotatable polarizer optic to at least two azimuthal orientations at each of the at least two azimuthal orientations of the calibration waveplate;

storing first output signals from the detectors at each of the at least two azimuthal orientations of the calibration waveplate and at each of the at least two azimuthal orientations of the azimuthally rotatable polarizer optic;

removing the rotatable calibration waveplate from the common beam path;

rotating the azimuthally rotatable polarizer optic in the polarization state generator to at least two azimuthal orientations;

storing second output signals from the detectors, at each of the at least two azimuthal orientations of the polarizer optic;

determining, via a non-linear regression analysis and a Mueller matrix model of the device optical components, the four by four instrument matrix for the wavelength based on: the first and second stored output signals from the detectors, the at least two azimuthal orientations of the polarizer optic, the at least two azimuthal orientations of the calibration waveplate, a retardation of the calibration waveplate at the wavelength, and a non-ideality factor for the polarization state generator.

12. A method for acquiring ellipsometric data, comprising:

mounting and aligning a sample on a frame;

aligning a polarizer optic within a polarization state generator to an operating azimuthal angle;

combining an output of a plurality of solid state light sources of the polarization state generator into a common beam;

directing the common beam toward the sample, the common beam having a common beam path;

receiving an incident beam transmission from the sample within a no moving parts polarimeter, the no moving parts polarimeter mounted to the frame;

receiving the incident beam with a plurality of detectors and converting the incident beam to a detector signal, the plurality of detectors configured for automated compensation for an angular misalignment of the incident beam, the plurality of detectors including at least a first detector D1 creating a first detector signal, a second detector D2 creating a second detector signal, a third detector D3 creating a third detector signal, a fourth detector D4 creating a fourth detector signal, a fifth detector D5 creating a fifth detector signal, a sixth detector D6 creating a sixth detector signal, and a seventh detector D7 creating a seventh detector signal;

receiving a plurality of detector signals for at least one wavelength from the plurality of detectors configured for receiving the incident beam;

arranging the plurality of detector signals into a four by one signal vector for the at least one wavelength;

multiplying the four by one signal vector for the at least one wavelength by an inverse of a four by four instrument matrix to form a four by one product vector, the four by four instrument matrix based on a calibration of the polarization state generator and the no moving parts polarimeter;

determining at least one ellipsometric data parameter for the wavelength based on the four by one product vector;

storing the determined at least one ellipsometric data parameter for further processing; and displaying the at least one ellipsometric data parameter to a user on a display.

13. The method for acquiring ellipsometric data of claim 12, wherein combining the output of the plurality of solid state light sources into the common beam occurs by at least one of: 1) combining through a cascading arrangement of partially reflective, partially transparent beamsplitters, and 2) combining through a diffraction grating oriented to correspond a zero order reflection of the diffraction grating to the common beam with individual output beams of the plurality of solid state light sources being aligned with a positive order or a negative order of the diffraction grating, wherein prior to the directing the common beam toward the sample, the polarizer state generator is further configured for:

collecting the common beam with a first lens and imaging the common beam on a pinhole;

scrambling the common beam with a light diffusing element;

collimating the common beam through the pinhole with a second lens;

rotating an azimuthally rotatable polarizer optic by at least one of: a computer controlled motor or a manually rotatable mechanism; and defining a diameter of the common beam transmitted through the pinhole with an aperture, and wherein the calibration of the polarization state generator and the no moving parts polarimeter further includes:

determining a first at least one four by four instrument matrix over a range of operating conditions, the range of operating conditions including at least one of:

one or more drive currents of the plurality of solid state light sources;

one or more temperatures;

one or more alignments of the common beam with respect to the no moving parts polarimeter;

fitting an element of the first at least one four by four instrument matrix to a polynomial function at a current operating condition of the range of operating conditions;

determining at least one variable associated with the current operating condition;

determining a second at least one four by four instrument matrix for the current operating condition based on the polynomial function of the element of the first at least one four by four instrument matrix and the at least one variable associated with the current operating condition; and storing at least the second at least one four by four instrument matrix for the current operating condition for use in acquiring ellipsometric data.

14. The method for acquiring ellipsometric data of claim 12, wherein the calibration of the polarization state generator and the no moving parts polarimeter further includes a window accuracy calibration of an in situ mode of ellipsometer operation with at least one window in the common beam path, comprising:

determining an optical model for a reference sample by acquiring ellipsometric data on the reference sample without the at least one window in the common beam path;

positioning the reference sample on the frame and the at least one window in the common beam path;

determining a window calibration data set by acquiring ellipsometric data on the reference sample at multiple orientations of the azimuthally rotatable polarizer optic;

determining an ellipsometric N parameter and a window-related Mueller matrix element for at least one wavelength based on the window calibration data set;

determining an angle of incidence of the common beam with respect to the reference sample based on the ellipsometric N parameter;

determining an ellipsometric C parameter and an ellipsometric S parameter for the reference sample based on the optical model of the reference sample and the angle of incidence of the common beam;

determining at least one window characterizing parameter based on the window-related Mueller matrix element, the ellipsometric N parameter, the ellipsometric C parameter, and the ellipsometric S parameter for the reference sample;

storing the at least one window characterizing parameter for use in acquiring ellipsometric data on a subsequent sample to increase an accuracy of the ellipsometric data.

15. The method for acquiring ellipsometric data of claim 12, further comprising:

measuring an intensity versus wavelength for each light source of the plurality of solid state light sources;

determining an intensity versus wavelength curve for each light source of the plurality of solid state light sources;

determining a plurality of lineshape characterizing parameters for each light source of the plurality of solid state light sources by fitting a piece-wise continuous function to the intensity versus wavelength curve for each light source of the plurality of solid state light sources, the piece-wise continuous function having a central Gaussian lineshape component and an adjacent exponential lineshape component;

building an optical model for the sample representative of a nominal structure of the sample, the optical model including a convolution with the fitted piece-wise continuous function with the central Gaussian lineshape component and the adjacent exponential lineshape component;

analyzing the ellipsometric data via a non-linear regression analysis from the optical model for the sample to determine at least one sample characterizing parameter;

storing the determined at least one sample characterizing parameter for further processing; and displaying the at least one sample characterizing parameter to a user on a display.

16. A multiple wavelength ellipsometer system, comprising:

a polarization state generator including a plurality of solid state light sources; and a no moving parts polarimeter, the no moving part polarimeter comprising:

an aperture to receive an incident beam;

at least three polarimeter sections arranged in series, a polarimeter section comprising a pair of beam splitters and a pair of detectors, each beam splitter configured to receive the incident beam, partially reflect the incident beam to a detector at an angle measured from the incident beam, and transmit a remaining incident beam, the polarimeter section configured for automated compensation of an angular misalignment of the incident beam by operatively arranging the pair of beam splitters and the pair of detectors to result a detector opposite another detector of the pair, a beam splitter opposite another beam splitter of the pair with respect to the angle measured from the incident beam, and the detector positioned to receive the partially reflected incident beam from the beam splitter; and a first retarder element, said first retarder element positioned in front of at least one of: the first polarimeter section, the second polarimeter section and the third polarimeter section.

17. The multiple wavelength ellipsometer system of claim 16, further comprising a second retarder element, wherein said first retarder element and said second retarder element is positioned in front of at least two of: the first polarimeter section, the second polarimeter section and the third polarimeter section, and wherein the polarization state generator further includes:

the plurality of solid state light sources configured to combine an output of the plurality of solid state light sources into a common beam;

a lens configured to collect the common beam and image the common beam on a pinhole;

a light diffusing element configured to scramble the common beam;

a lens configured to collimate the common beam through the pinhole;

an azimuthally rotatable polarizer optic, the azimuthally rotatable polarizer optic azimuthally rotated by one of: a computer controlled motor and a manually rotatable mechanism; and an aperture to define a diameter of the common beam transmitted through the pinhole.

18. The multiple wavelength ellipsometer system of claim 17, further comprising a third retarder element, wherein said first retarder element is positioned in front of the first polarimeter section, said second retarder element is positioned in front of the second polarimeter section, and said third retarder element is positioned in front of the third polarimeter section, and wherein the polarization state generator is configured to combine the output of the plurality of solid state light sources into the common beam using a cascading arrangement of partially reflective, partially transparent beamsplitters.

19. The multiple wavelength ellipsometer system of claim 17, wherein the polarization state generator is configured to combine the output of the plurality of solid state light sources into the common beam using a diffraction grating oriented to correspond a zero order reflection of the diffraction grating to the common beam, and wherein individual output beams of the plurality of solid state light sources are aligned with at least one of: a positive order or a negative order of the diffraction grating.

20. A multiple wavelength ellipsometer system configured to acquire ellipsometric data, comprising:

means for generating a common beam from a plurality of solid state light sources within a polarization state generator;

means for mounting and aligning a sample;

means for receiving an incident beam, the incident beam received from the common beam reflected from the sample;

means for automatic compensation for a misalignment of the incident beam;

means for measuring, within a polarization state detector, at least one ellipsometric data parameter of the sample, the measuring requiring no moving parts within the polarization state detector;

means for analysis of the at least one ellipsometric data parameter;

means for determining at least one ellipsometric parameter and at least one sample characterizing parameter based on the analysis means; and means for displaying the at least one ellipsometric parameter and the at least one sample characterizing parameter.

\* \* \* \* \*